United States Patent
Ruppersberg

(10) Patent No.: US 10,888,236 B2
(45) Date of Patent: *Jan. 12, 2021

(54) SYSTEM FOR ANALYZING ELECTROPHYSIOLOGICAL DATA AND METHOD FOR ANALYZING ELECTROPHYSIOLOGICAL DATA

(71) Applicant: Ablacon Inc., Wheat Ridge, CO (US)

(72) Inventor: Peter Ruppersberg, Blonay (CH)

(73) Assignee: Ablacon Inc., Wheat Ridge, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/756,865

(22) PCT Filed: Sep. 7, 2016

(86) PCT No.: PCT/EP2016/001515
§ 371 (c)(1),
(2) Date: Mar. 1, 2018

(87) PCT Pub. No.: WO2017/041892
PCT Pub. Date: Mar. 16, 2017

(65) Prior Publication Data
US 2018/0279896 A1    Oct. 4, 2018

(30) Foreign Application Priority Data
Sep. 7, 2015    (EP) .................. PCT/EP2015/001803

(51) Int. Cl.
*A61B 5/04*    (2006.01)
*A61B 5/00*    (2006.01)
(Continued)

(52) U.S. Cl.
CPC ........ *A61B 5/04011* (2013.01); *A61B 5/0006* (2013.01); *A61B 5/044* (2013.01);
(Continued)

(58) Field of Classification Search
CPC ........... A61B 5/04; A61B 5/044; A61B 18/14; A61B 5/0402; A61B 5/00; A61B 5/042;
(Continued)

(56) References Cited

U.S. PATENT DOCUMENTS 6,725,085 B2    4/2004    Schwartzman et al.
8,647,284 B2    2/2014    Afonso
(Continued)

FOREIGN PATENT DOCUMENTS

EP    2638852    9/2013
EP    3192445    7/2017
(Continued)

OTHER PUBLICATIONS

Mark Potse, Scalable and Accurate ECG Simulation for Reaction-Diffusion Models of the Human Heart, Apr. 20, 2018, 1-14, vol. 9, Art. 370, Frontiers in Physiology, Switzerland.
(Continued)

*Primary Examiner* — Jon Eric C Morales
(74) *Attorney, Agent, or Firm* — Woods Patent Law, P.C.

(57) ABSTRACT

The present invention concerns a system (100) for analyzing electrophysiological data, especially intracardial electrogram data, the system (100) comprising a data processing and control unit (15) for processing the electrophysiological data, a data output unit comprising a data output screen (324) for displaying results of electrophysiological data analysis, wherein the data processing and control unit (15) being configured to receive electrophysiological data obtained from a mapping catheter assembly (110, 111) that comprises an electrode assembly (120, 80) with a plurality of n electrodes (82), each electrode (82) configured for measuring electrophysiological data in the form of electrogram signals. The data processing and control unit (15) comprises an engine for performing an optical flow analysis
(Continued)

of the electrophysiological data to generate series of vector data (40) representing the average speed and direction of movement of clusters of the electrophysiological data, the data output unit being configured to display the vector data on a data output screen (324) of the data output unit.

21 Claims, 26 Drawing Sheets

(51) Int. Cl.
*A61B 18/14* (2006.01)
*A61B 5/042* (2006.01)
*A61B 5/0402* (2006.01)
*A61B 5/044* (2006.01)
*A61B 5/0452* (2006.01)
*A61B 18/00* (2006.01)

(52) U.S. Cl.
CPC ........ *A61B 5/04017* (2013.01); *A61B 5/0422* (2013.01); *A61B 5/04028* (2013.01); *A61B 5/0452* (2013.01); *A61B 5/6857* (2013.01); *A61B 5/6858* (2013.01); *A61B 5/6859* (2013.01); *A61B 18/1492* (2013.01); *A61B 2018/00351* (2013.01); *A61B 2018/00357* (2013.01); *A61B 2018/00577* (2013.01); *A61B 2018/00839* (2013.01); *A61B 2018/1437* (2013.01)

(58) Field of Classification Search
CPC .............. A61B 5/04017; A61B 5/6858; A61B 18/1492; A61B 5/6852; A61B 5/742; A61B 5/0006; A61B 5/04011; A61B 5/04012; A61B 5/04028; A61B 5/0422; A61B 2090/065; A61B 2018/00577; A61B 2018/00351; A61B 2018/1467; A61B 2018/00267

See application file for complete search history.

(56) References Cited

U.S. PATENT DOCUMENTS

| | | | |
|---|---|---|---|
| 9,642,674 | B2 | 5/2017 | Chmiel et al. |
| 10,143,374 | B2* | 12/2018 | Ruppersberg ...... A61B 5/04017 |
| 10,201,277 | B2* | 2/2019 | Ruppersberg ...... A61B 5/04017 |
| 2007/0219454 | A1 | 9/2007 | Guzzetta et al. |
| 2015/0164349 | A1 | 6/2015 | Gopalakrishnan |
| 2015/0216438 | A1 | 8/2015 | Bokan |
| 2016/0000357 | A1 | 1/2016 | Harlev et al. |
| 2017/0065198 | A1 | 3/2017 | Ruppersberg |

FOREIGN PATENT DOCUMENTS

| | | |
|---|---|---|
| EP | 3346914 | 7/2018 |
| EP | 3375365 | 9/2018 |
| EP | 16843733.3 | 9/2018 |
| EP | 18162169.8 | 11/2018 |
| EP | EESR 3556284/19170337 | 11/2019 |
| EP | ESR 19219296.1 | 7/2020 |
| WO | WO 2012/092016 A1 | 7/2012 |
| WO | WO 2016/077786 | 5/2016 |

OTHER PUBLICATIONS

Bellmann, B. et al, "Electrographic flow mapping—A new technology for identification of atrial drivers," Europace, vol. 198, No. suppl_3, Jun. 2017, pp. iii54-iii55.

* cited by examiner

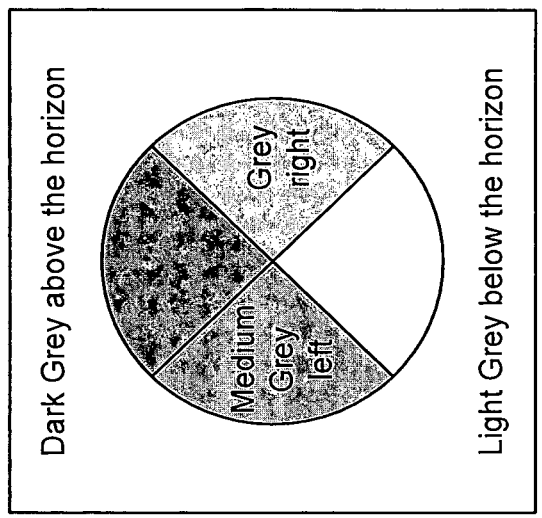
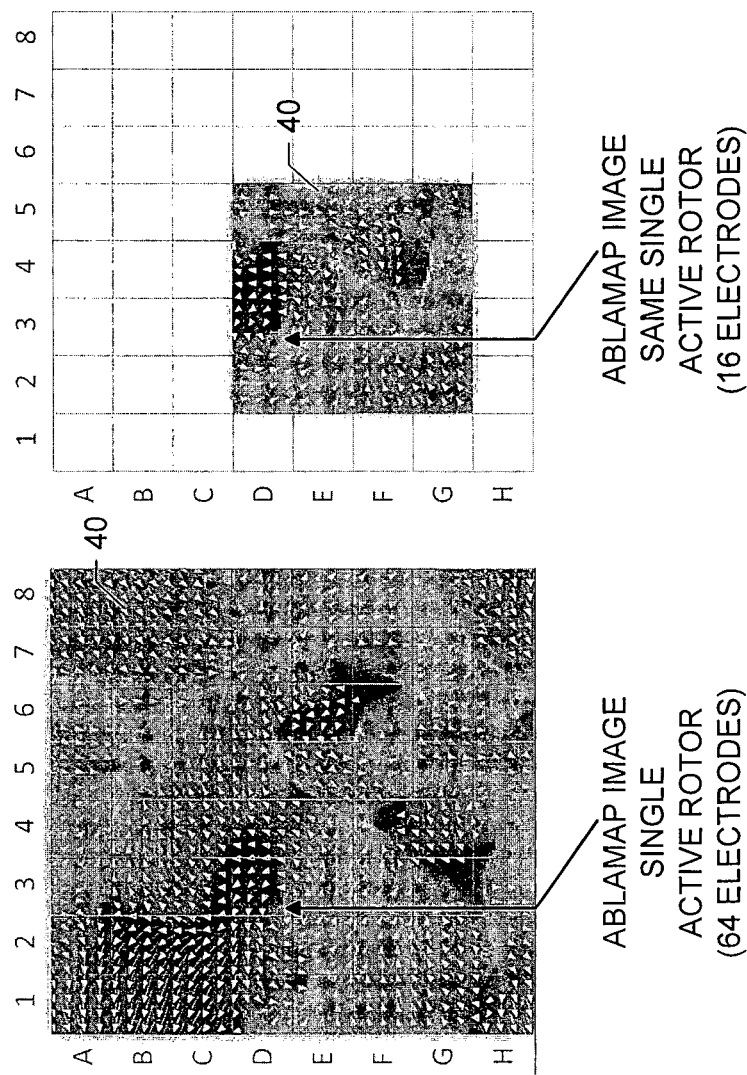
FIG. 10(a)    FIG. 10(b)    FIG. 10(c)

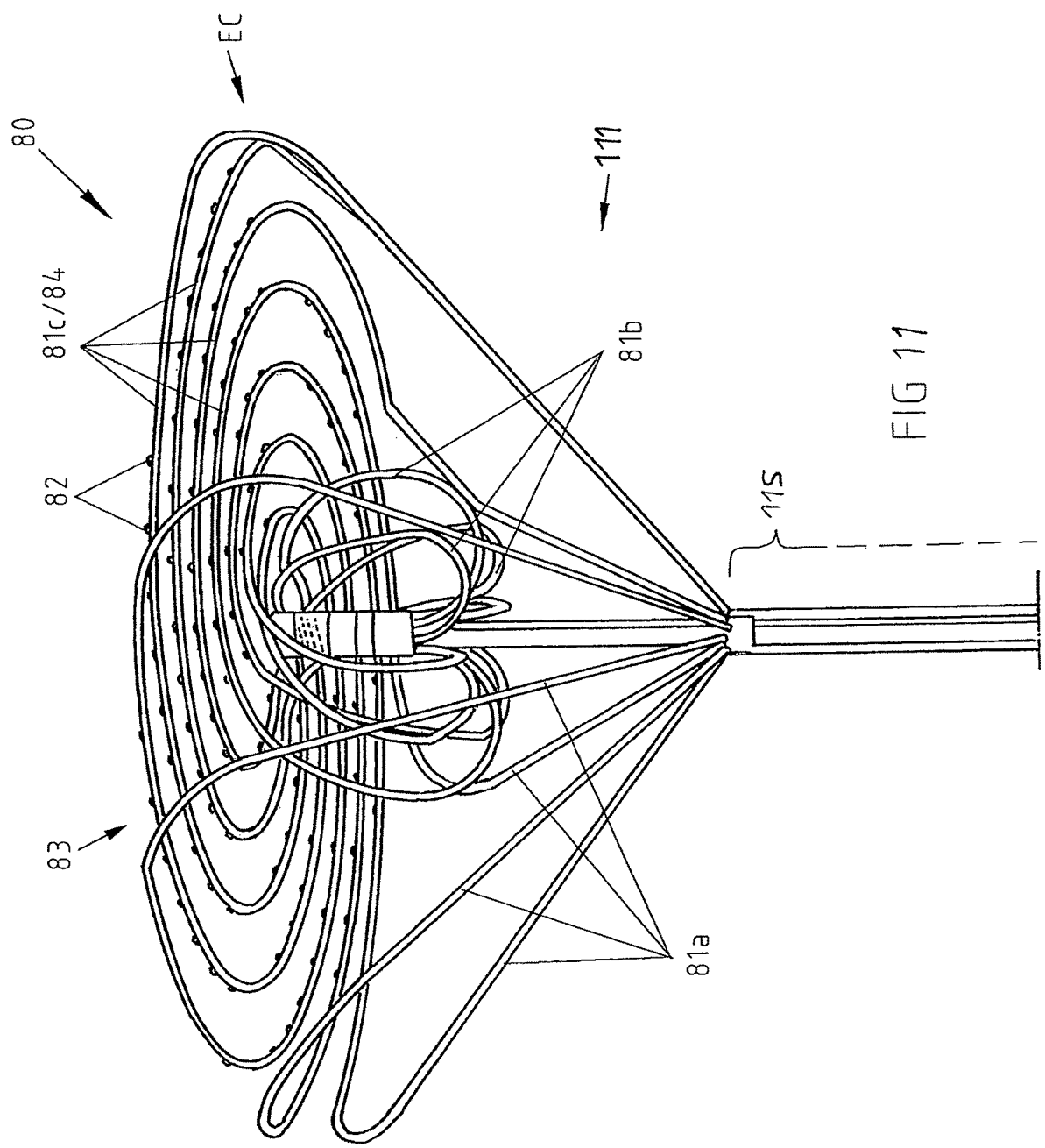

SYSTEM FOR ANALYZING ELECTROPHYSIOLOGICAL DATA AND METHOD FOR ANALYZING ELECTROPHYSIOLOGICAL DATA

This application is a national stage entry of, and claims priority and other benefits from, International Patent Application PCT/EP2016/001515 to Ruppersberg filed on Sep. 7, 2016, which is entitled "System for Analyzing Electrophysiological Data and Method for Analyzing Electrophysiological Data "(hereafter "the '001515 patent application"). This application also claims priority and other benefits from International Patent Application PCT/EP2015/001801 to Ruppersberg filed Sep. 7, 2015, which is entitled "Elongated Medical Device Suitable for Intravascular Insertion and Method of Making an Elongated Medical Device Suitable for Intravascular Insertion "(hereafter "the '001801 patent application"), and from which the '001515 patent application also claims priority. This application further claims priority and other benefits from International Patent Application PCT/EP2015/001803 to Ruppersberg filed on Sep. 7, 2015, which is entitled "Elongated Medical Device Suitable for Intravascular Insertion and Method of Making an Elongated Medical Device Suitable for Intravascular Insertion" (hereafter the '001803 patent application"), and from which the '001515 patent application further claims priority. The respective entireties of the '001801, '001803 and '001515 patent applications are hereby incorporated by reference herein.

The present invention relates generally to a system for analyzing electrophysiological data, especially intracardial electrogram data, the system comprising a data processing and control unit, such as a computer system, for processing the electrophysiological data, a data output unit comprising a data output screen for displaying results of electrophysiological data analysis, wherein the data processing and control unit is configured to receive electrophysiological data obtained from a mapping catheter assembly that comprises an electrode assembly with a plurality of n electrodes, each electrode configured for measuring electrophysiological data in the form of electrogram signals. Such mapping catheters suitable for intravascular insertion may be manually or robotically steerable catheters for the exploration or treatment of vessels or organs or other body cavities or guide wires for guiding catheters or the like medical apparatuses.

Further, the present invention relates to a method of analyzing electrophysiological data, especially action potential data, The expression action potential data is seen and used in the following as a synonym for intracardial electrogram data and vice versa.

The present invention especially relates to a system for analyzing electrophysiological data, especially intracardial electrogram data, with individual features of claim 1, and a method of analyzing electrophysiological data, especially action potential data, with individual features of the respective independent method claim.

Elongated medical devices suitable for intravascular insertion, such as catheters, especially ablation catheters, and guide wires for guiding catheters through vessels, organs or other body cavities are e.g. used in the treatment of atrial fibrillation (Afib).

Atrial fibrillation is the most frequent arrhythmic disorder of the heart. Blood clotting occurring in the fibrillating atria is one main cause of stroke. In so far, Afib is one of the most important disorders associated with a high fatal risk. The cause for Afib has been subject to intensive scientific investigations and is meanwhile largely understood. In most patients, the pulmonary veins draining into the left atrium are the sources of rapid arrhythmic action potentials which trigger circular excitation patterns (rotors), in the left atrium that induce a high frequency fibrillation through their re-entry mechanism. Those rotors have the character of small action potential cyclones of 2 to 3 $cm^2$ in size. The likelihood of occurrence of those rotors and the frequency of pathological action potential generation in the pulmonary veins increases with fibrotic structural changes and certain modifications of ion channel expression patterns in atrial cells with age.

The only potentially curative treatments for Afib are open heart surgery or catheter ablation of those parts of the atrial wall tissue which originate, transmit or maintain the pathologic excitation circles.

Today the use of catheter ablation like open heart surgery is still limited by the potentially fatal risk of some severe side effects associated with the procedure: When the integrity of the atrial wall is destroyed by too intense ablation, perforations of the atrial wall into the pericardium or fistulas into the esophagus can have severe to deadly outcomes. The alteration of the endocardial cells on a larger surface can initiate clotting in the treated atrium which may lead to deadly strokes. That is why the procedure requires full anticoagulation. Last but not least, if the intensity of the ablation is kept too low to avoid those side effects in many cases the therapeutic effect is insufficient and patients face a success rate of the treatment of only 50-70% on average.

To improve the situation, mapping catheters are used to first identify circular excitation patterns (rotors) in the left atrium. After identification of rotors, force sensing catheters are used that allow to better control the catheter positioning pressure which has an influence on the intensity of ablation. Further, water irrigation tries to keep the endothelial tissue free of lesions and micro-calorimetric sensors try to measure and control the heat in the tissue.

U.S. Pat. No. 8,364,234 discloses a system for sensing multiple local electric voltages from endocardial surface of a heart. The system includes a first elongate tubular member; a basket assembly having a plurality of flexible splines for guiding a plurality of exposed electrodes, the splines having proximal portions, distal portions and medial portions therein between; a proximal anchor for securely affixing the proximal portions of the splines; the proximal anchor being secured at the distal end of the first elongate tubular member; a distal tip consisting essentially of means for only securely affixing the distal portions of the splines wherein at least some of the splines in the radially expanded non-spherical shape contain a distal excurvate outward bend disposed at the distal portion of the spline at a location near to the distal tip of the basket assembly to bend the splines back towards the proximal anchor. A disadvantage of this type of mapping system is the low resolution provided by the mapping electrode array, especially in the area of the equator of the system in its radially expanded shape.

One system and method currently employed to localize Afib drivers (i.e.active rotors) is the TOPERA® RhythmView® system, which employs a basket catheter having 64 electrodes arranged in an 8×8 pattern from which the system records unipolar electrograms or electrogram signals (EGMs). The RhythmView® algorithm creates a propagation map of the 64 electrodes through a phase analysis of EGM peaks after improving the signal to noise ratio through filtering and subtraction of a simulated compound ECG artefact. The RhythmView® algorithm detects where peak sequences between electrodes show a circular pattern suspect for a re-entry cycle and indicates those locations in a Focal Impulse and Rotor Map (FIRM) using A1 to H8 chess field coordinates for the electrodes. The resolution of the TOPERA system is limited by the spacing of the electrodes and consequently does not show the details of the Afib drivers. In particular, the TOPERA system does not show if a circular EGM wavefront is actively generated by a re-entry mechanism and is therefore is a driver of Afib (i.e., an active rotor), or whether a circular EGM wavefront simply represents turbulence passively generated by an EGM wavefront hitting a barrier (i.e., a passive rotor). In addition, the TOPERA system does not show the direction of Afib wavefront propagation, and does not provide the spatial or temporal resolution required to detect singularities associated with the generation of an active rotor.

A recent independent multicenter study ("OASIS, Impact of Rotor Ablation in NonParoxysmal AF Patients: Results from a Randomized Trial," Sanghamitra Mohanty, et al. and Andrea Natale, J Am Coll Cardiol. 2016) reported that the results obtained using TOPERA FIRM technology were inferior to those provided by non-specific ablation of the posterior wall of the left atrium. Moreover, the results suggested that FIRM based ablation is not sufficient for therapeutic success without pulmonary vein isolation being performed in parallel. Although here are some questions about the methodology of this trial, many experts are convinced that the resolution and interpretability of the TOPERA system need to be improved.

WO2015130824 A1 discloses a system for determining electrophysiological data comprising an electronic control unit configured to acquire electrophysiology signals from a plurality of electrodes of one or more catheters, select at least one clique of electrodes from the plurality of electrodes to determine a plurality of local E field data points, determine the location and orientation of the plurality of electrodes, process the electrophysiology signals from the at least one clique from a full set of bipole subcliques to derive the local E field data points associated with the at least one clique of electrodes, derive at least one orientation independent signal from the at least one clique of electrodes from the information content corresponding to weighted parts of electrogram signals, and display or output catheter orientation independent electrophysiologic information to a user or process. This system defines the electric field by means of a mathematical derivation (or better time derivative?) of the potential according to the electrode distance. This derivation constitutes a high pass filter that causes spatial noise. The aim is to identify circular structures. Anyhow, with the use of such high pass filter the noise increases significantly such that rotors can't be clearly identified.

The approach of WO2015130824 was recently thematized by Toronto scientists as a strategy to analyze EGM wave propagation using "Omnipolar Mapping," which seeks to measure beat by beat conduction velocity and direction (see, e.g., "Novel Strategy for Improved Substrate Mapping of the Atria: Omnipolar Catheter and Signal Processing Technology Assesses Electrogram Signals Along Physiologic and Anatomic Directions," D. Curtis Deno et al. and Kumaraswamy Nanthakumar; Circulation. 2015; 132: A19778). This approach starts with the time derivative of a unipolar EGM as measured by a set of electrodes having known distances to one other. Assuming constant velocity, the velocity and direction representing the best fit for a spatial derivative of the measured EGM are calculated and used to represent an estimate of the E field. According to a communication by Dr. Nanthakumar at the 2016 CardioStim Convention in Nice, France, this method remains incapable of dealing successfully with complex data sets, such as those obtained during an episode of Afib.

U.S. Pat. No. 7,081,114 B2 discloses a remotely deflectable electrophysiology/ablation catheter of the type intended for placing into an interior passage of the heart is disclosed. The distal end of this elongated tubular catheter has a pair of tension/compression members each with a flattened end portion connected to the distal electrode and extending through the catheter casing and attached to a user moveable actuator for effecting the tension/compression thereon for remotely curling the distal end of the catheter. Spaced ring electrodes are provided adjacent the distal electrode. A permanent bend is pre-formed in the casing and tension/compression members adjacent the ring electrodes about an axis perpendicular to the elongated tension/compression members. Movement of the remote actuator causes the distal portion of the catheter to curl into a lariat in a plane perpendicular to the axis along the elongated catheter casing, thus permitting electrical mapping or ablation with the distal and/or ring electrodes about the inner surface of the heart passage into which the lariat is formed and situated. The lariat can achieve a curvature greater than 360 degrees and at a significantly reduced radius to allow insertion of the catheter distal end into passages of reduced dimension. A disadvantage of this catheter is the low resolution of the electrode array when used for mapping due to the limited number of electrodes and due to the relative large distances from electrode to electrode in the radial direction.

WO 2012/092016 discloses a medical device having a distal end that is arranged in a spiral configuration having a single spiral arm extending between an elongated part of the device and its distal end, which is formed on the end of the spiral arm. The spiral configuration is generally planar and contains a number of electrodes for taking unipolar or bipolar measurements from a tissue. In one exemplary embodiment, the diameter of the outermost loop of the spiral configuration is twenty millimeters. The spiral configuration may contain multiple spiral loops. Anyhow, a first disadvantage of this device is that the maximum diameter of the spiral configuration loops is restricted by the diameter of the vessel, organ or other body cavity the device is to be introduced in. Further, the number of electrodes of this spiral configuration, even with more than one loop, is restricted due to the size limitations and hence maximum resolution is restricted too and there is a relative large "blind" area in the center of the spiral configuration.

US 2008/0275367 A1 discloses robotic instrument systems and methods for generating a geometric map of an area of body tissue which is correlated with a tissue characteristic such as tissue compliance or related property. The system comprises a robotically controlled catheter which is controlled by a robotic instrument driver. A force sensor system is provided that generates force signals responsive to a force applied to the distal end of the catheter. A position determination system is also provided which generates position signals responsive to the location of the distal end of the catheter. A computer is configured to receive and process the force signals and position signals to generate a geometric map of an area of body tissue correlated to the tissue compliance of different regions of the body tissue or a tissue characteristic determinable from the tissue compliance.

It is hence a task of the present invention to provide an improved system for and methods of analyzing or processing electrophysiological data, especially in the form of electrogram signals that reliably and accurately yield the precise locations and sources of rhythm disorders in a patient's body, e.g. cardiac rhythm disorders in a patient's heart.

These and other objects of the present invention are accomplished by providing the data processing and control unit with an engine for performing an optical flow analysis of the electrophysiological data to generate series of vector data representing the average speed and direction of movement of clusters of the electrophysiological data, the data output unit being configured to display the vector data on a data output screen of the data output unit. The optical flow engine (or alternatively the optical flow detector) is a part of the data processing and control unit that processes the electrophysiological data by means of an optical flow analysis. With the optical flow engine the motion of electrophysiological data points in a sequence are computed and accordingly the system is enabled to identify the direction and/or velocity of rotation of rotors and to localize them in the examined part of the body, e.g. in the atrium of the heart, and to display this information on the data output unit in form of a velocity vector map.

Advantageously, the data processing and control unit is configured to average n electrogram signals received from the n electrodes at a determined time slice in order to generate an average signal for the determined time slice and to subtract the averaged signal from each of the n electrogram signals to generate n adjusted electrogram signals. The advantage of this is, that common electrogram artefacts are removed such that the adjusted electrogram signals are artefact free. Such artefacts may be caused by an overall depolarization of the surface to be examined, measured by all electrodes. E.g. ventricular depolarization may be superimposed to all local potentials of the individual electrodes.

Preferably, the data processing and control unit comprises a high pass filter between 5 and 20 Hz for filtering the n adjusted electrogram signals. With this high pass filter following the artefact removal, the DC offset of the signal is removed such that each signal is symmetrically swinging around zero.

Advantageously, the data processing and control unit is configured to determine the amplitude value of each of the n adjusted electrogram signals in the determined time interval and to store these n amplitude values associated to the determined time slice in a memory. The Memory is preferably comprised in the data processing and control unit/ computer system. The advantage of storing the amplitude values of each of the n adjusted electrogram signals is that they may be used when the electrophysiologic data are output on the data output unit to form an image background that may indicate loose electrode contact or indicate conditions of the examined body area, such as fibrotic areas or valve artefacts. Storing the amplitude values of each of the n adjusted electrogram signals preferably occurs subsequently to the high pass filtering.

Preferably, the data processing and control unit is configured to define the standard deviation for the set of n amplitude values for each determined time slice and to normalize each of the n amplitude values in the determined time slice by the standard deviation in order to generate a set of n normalized amplitude values. The resulting normalized amplitude values advantageously yield a first spatial information about the action potential wave pattern for each sampled point.

In an advantageous embodiment of the invention, n is defined by a grid of $n_y$ electrodes length by $n_x$ electrodes width, wherein the data processing and control unit is configured to define virtual amplitude values of virtual electrogram signals located in between electrogram signals of neighboring electrodes in the $n_y$, $n_x$ electrode grid for each determined time slice, and wherein the total number $n_v$ of virtual electrogram signals is at least 10 times, preferably 10-100 times, more preferably 20-40 times the total number n of measured electrogram signals and wherein the virtual amplitude value of a virtual electrogram signal located in between two neighboring electrogram signals is defined to be the average of the amplitude values of the neighboring electrogram signals, wherein the neighboring electrogram signals may be either one of measured or virtual electrogram signals. With the determination of virtual electrogram signals the set of electrophysiological data resulting from the electrogram signals may be significantly enhanced, such that the optical flow analysis by means of the optical flow engine will result in a much smoother vector image or map with an enhanced resolution.

Further advantageously, the optical flow engine of the data processing and control unit is configured to process sets of electrophysiological data associated to determined time slices comprising virtual and measured electrogram signals including their respective amplitude values to generate series of vector data representing the average speed and direction of movement of the clusters of electrophysiological data. Accordingly the recognizability of rotors/rotor structures is improved by introducing the virtual electrogram signals and by performing optical flow analysis on the virtual and measured electrogram signals including their respective amplitude values.

Preferably, the definition of virtual amplitude values of virtual electrogram signals is performed using a 2D biharmonic spline interpolation engine of the data processing and control unit. The 2D biharmonic spline interpolation engine may e.g. use Green's function to generate smoothed electrogram surfaces.

In a further advantageous embodiment of the invention, the data output unit is configured to display passive and active rotors by means of the vector that are displayed on the data output screen of the data output unit. The operator of the system is hence enabled to easily identify the type rotor visible on the data output screen.

Advantageously, the data output screen is configured to display vector data in form of data arrows, the total of the data arrows displayed representing action potential wave maps. In these action potential wave maps, rotors may easily be identified so that ablation may immediately be initiated so that rotors may be ablated on the spot.

Preferably, the optical flow engine of the data processing and control unit is configured to process electrophysiological data using a data analysis method chosen from the group consisting of phase correlation method, block-based method, discrete optimization methods and differential methods of estimating optical flow including the Lucas-Kanade method, the Horn-Schunck method, the Buxton-Buxton method and the Black-Jepson method or any variations thereof. Such optical flow analysis allows for a data integration time in the range between 100 ms and 10 seconds.

A favourable method of analyzing electrophysiological data, especially action potential data, comprises the steps of:
  measuring electrophysiological data, especially in the form of electrogram signals, with a plurality of mapping electrodes (82) disposed at a distal end of an elongated medical device,
  transmitting the electrophysiological data/action potential data from the plurality of mapping electrodes to a data processing and control unit, performing an optical flow analysis of the electrophysiological data/action potential data and generate series of vector data representing the average speed of movement of clusters of the action potentials, displaying the vector data on a data output screen of the data output unit.

By means of this inventive method it is possible for the first time to visualize the direction of rotation of rotors and to localize them in the atrium of the heart.

Advantageously, the action potential data is analyzed with an algorithm called optical flow analysis which estimates the average speed and direction of action potential propagation at a certain electrode. This yields vector data which are displayed on the data output screen, e.g. on a display, in form of data arrows, the total of the data arrows displayed represent action potential wave maps. In these action potential wave maps, rotors may easily be identified so that ablation may immediately be initiated so that rotors may be ablated on the spot.

Optical flow analysis may be performed using a data analysis method chosen from the group consisting of phase correlation method, block-based method, discrete optimization methods and differential methods of estimating optical flow including the Lucas-Kanade method, the Horn-Schunck method, the Buxton-Buxton method and the Black-Jepson method or any variations thereof. Preferably, the Horn-Schunck method is used. Such optical flow analysis allows for a data integration time in the range between 100 ms and 10 seconds.

In an advantageous step of the method, the electrophysiological data are acquired by the mapping electrodes in the form of electrogram signals, wherein n electrogram signals received from n mapping electrodes at a determined time slice are averaged in order to generate an average signal for the determined time slice and wherein the averaged signal is subtracted from each of the n electrogram signals to generate n adjusted electrogram signals. The advantage of this averaging step is that common electrogram artefacts are removed such that the adjusted electrogram signals are artefact free.

Preferably, the n adjusted electrogram signals are high pass filtered between 5 and 20 Hz in a filtering step. The filtering step may follow or precede the averaging step. With the filtering step, DC components and other noise is advantageously removed.

Advantageously, in an amplitude value determination step, the amplitude value of each of the n adjusted electrogram signals in the determined time slice is determined and the n amplitude values associated to the determined time slice are stored in a memory. The Memory is preferably comprised in the data processing and control unit/computer system. The advantage of storing the amplitude values of each of the n adjusted electrogram signals is that they may be used when the electrophysiologic data are output on the data output unit to form an image background that may indicate loose electrode contact or indicate conditions of the examined body area, such as fibrotic areas or valve artefacts. Storing the amplitude values of each of the n adjusted electrogram signals preferably occurs subsequently to the filtering step.

Preferably, in a normalization step, a standard deviation of the set of n amplitude values for each determined time slice is determined and each of the n amplitude values in the determined time slice are normalized by the standard deviation in order to generate a set of n normalized amplitude values. The resulting normalized amplitude values advantageously yield a first spatial information about the action potential wave pattern for each sampled point.

Advantageously, n is defined by a grid of $n_y$ electrodes length by $n_x$ electrodes width, wherein, in a step of generating virtual amplitude values, virtual amplitude values of virtual electrogram signals are defined by the data processing and control unit that are located in between electrogram signals of neighboring electrodes in the $n_y$, $n_x$ (or alternatively referred to as x, y) electrode grid for each determined time slice, and wherein the total number $n_v$ of virtual electrogram signals is at least 10 times, preferably 10-100 times, more preferably 20-40 times the total number n of measured electrogram signals and wherein the virtual amplitude value of a virtual electrogram signal located in between two neighboring electrogram signals is defined to be the average of the amplitude values of the neighboring electrogram signals, wherein the neighboring electrogram signals may be either one of measured or virtual electrogram signals. With the generation and inclusion of virtual electrogram signals the set of electrophysiological data resulting from the electrogram signals may be significantly enhanced.

In a preferred embodiment, the definition of virtual amplitude values of virtual electrogram signals is performed using a 2D biharmonic spline interpolation engine of the data processing and control unit. The 2D biharmonic spline interpolation engine may be used in combination with Green's function to generate smoothed electrogram surfaces.

Preferably, the optical flow analysis is performed on sets of electrophysiological data associated to determined time slices comprising virtual and measured electrogram signals including their respective amplitude values to generate series of vector data representing the average speed and direction of movement of the clusters of electrophysiological data such that the optical flow analysis will result in a much smoother vector image or map with an enhanced resolution.

Further features of the invention, its nature and various advantages will become more apparent from the accompanying drawings and the following detailed description of the preferred embodiments, in which.

Figure 2:
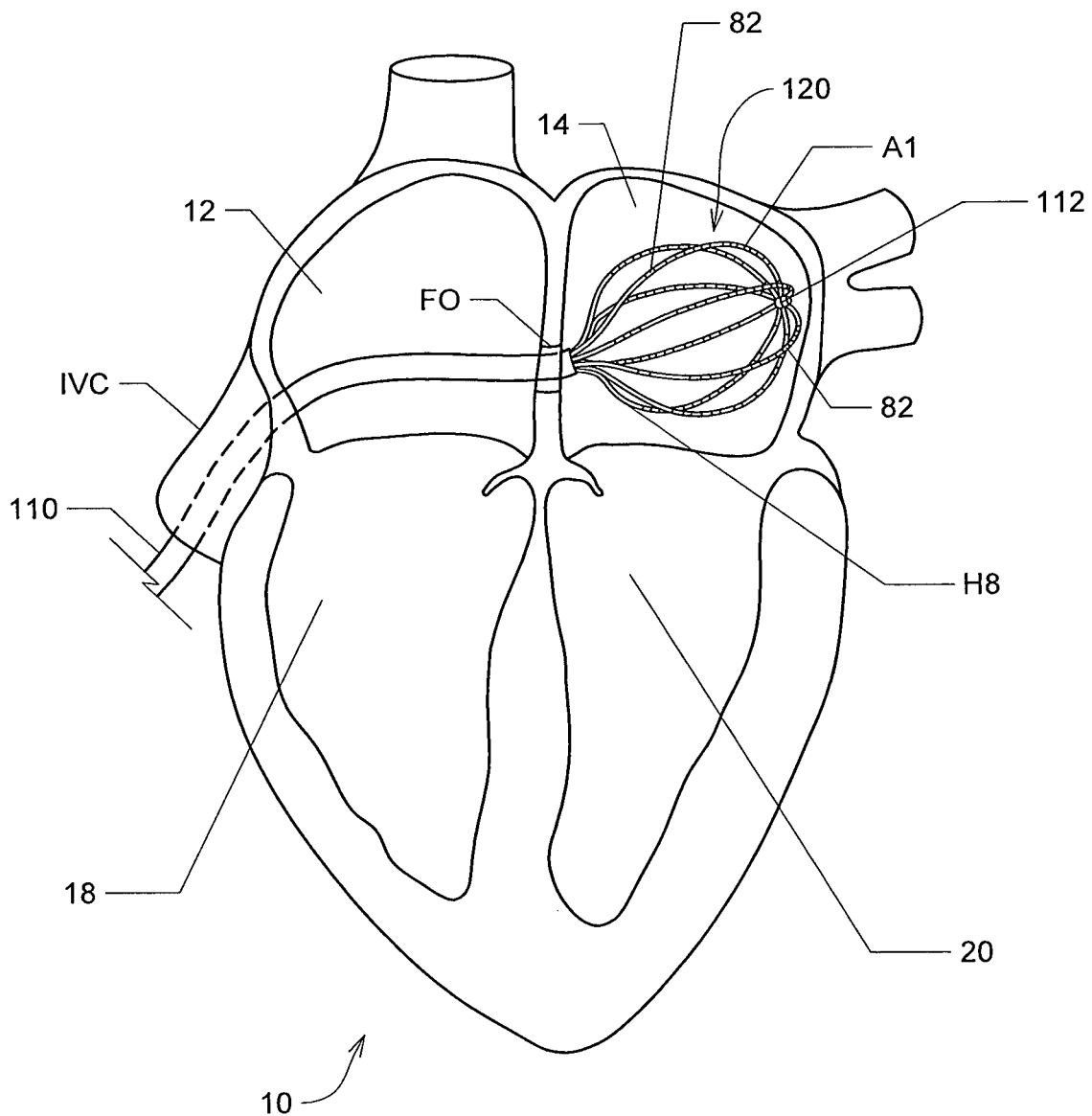
FIG. 2 shows an illustrative view of one embodiment of a distal portion of catheter 110 inside a patient's left atrium 14.
Figure 4:
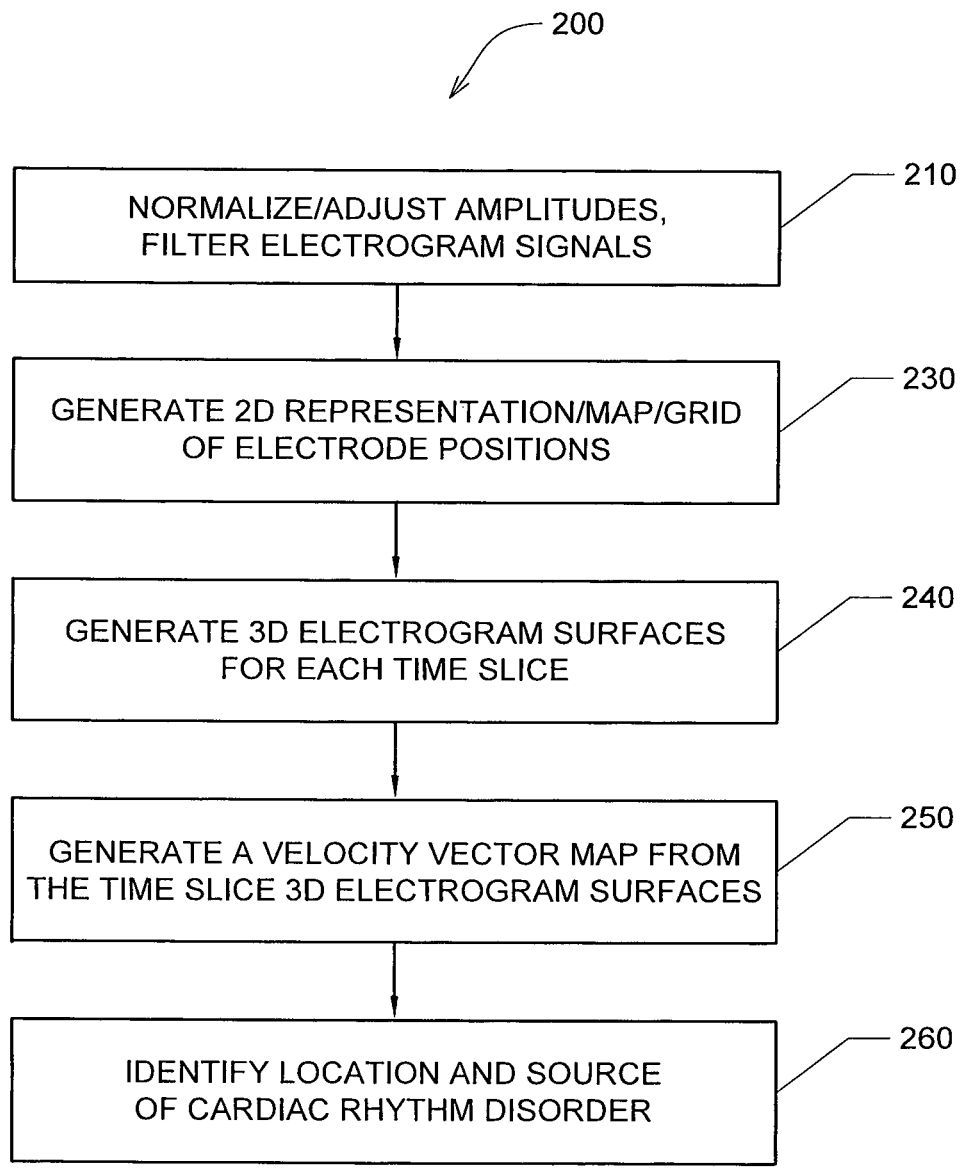
FIG. 4 shows one embodiment of an algorithm or method 200 of detecting a location of a source of at least one cardiac rhythm disorder in a patient's heart.
Figure 6A:
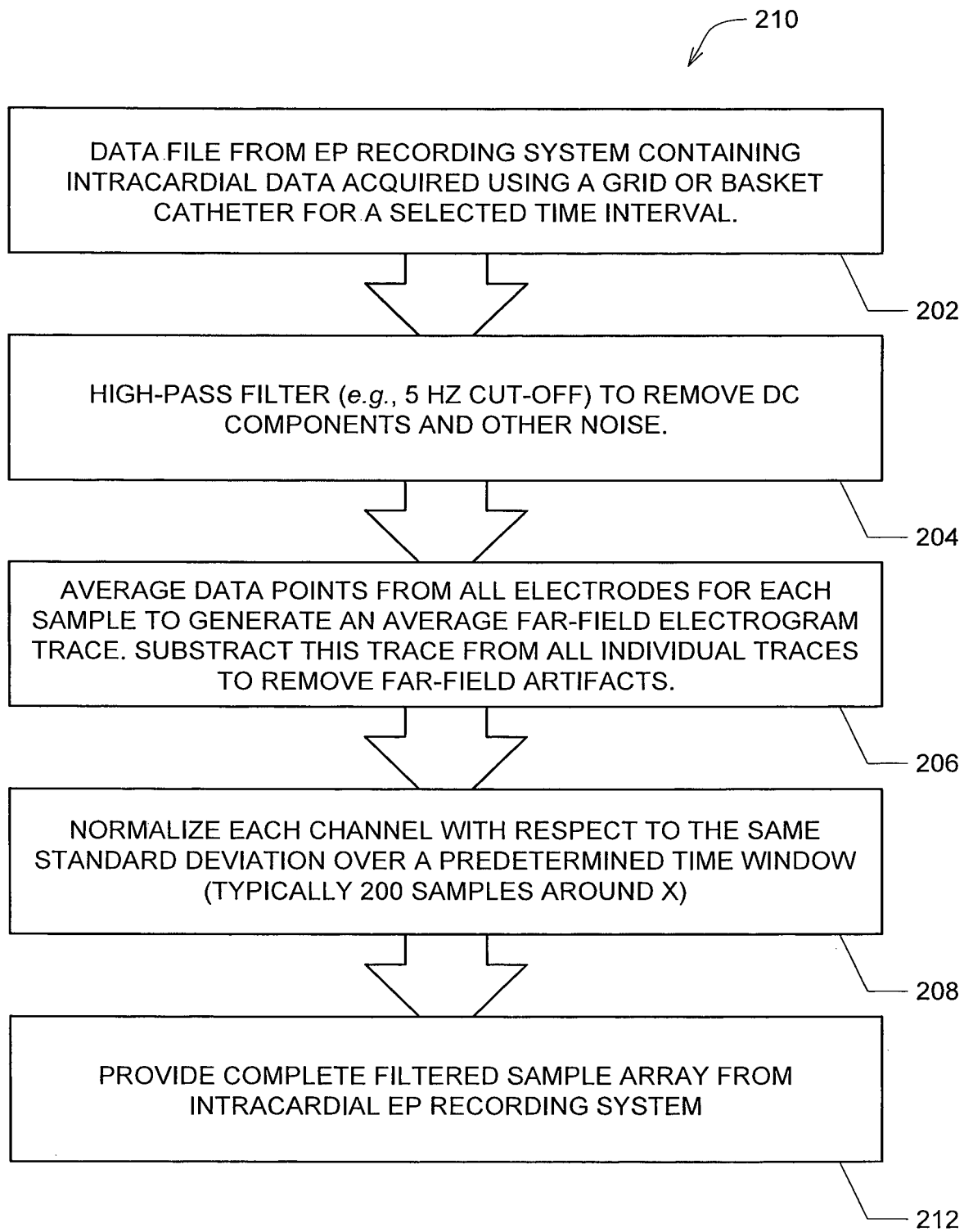
Figure 6B:
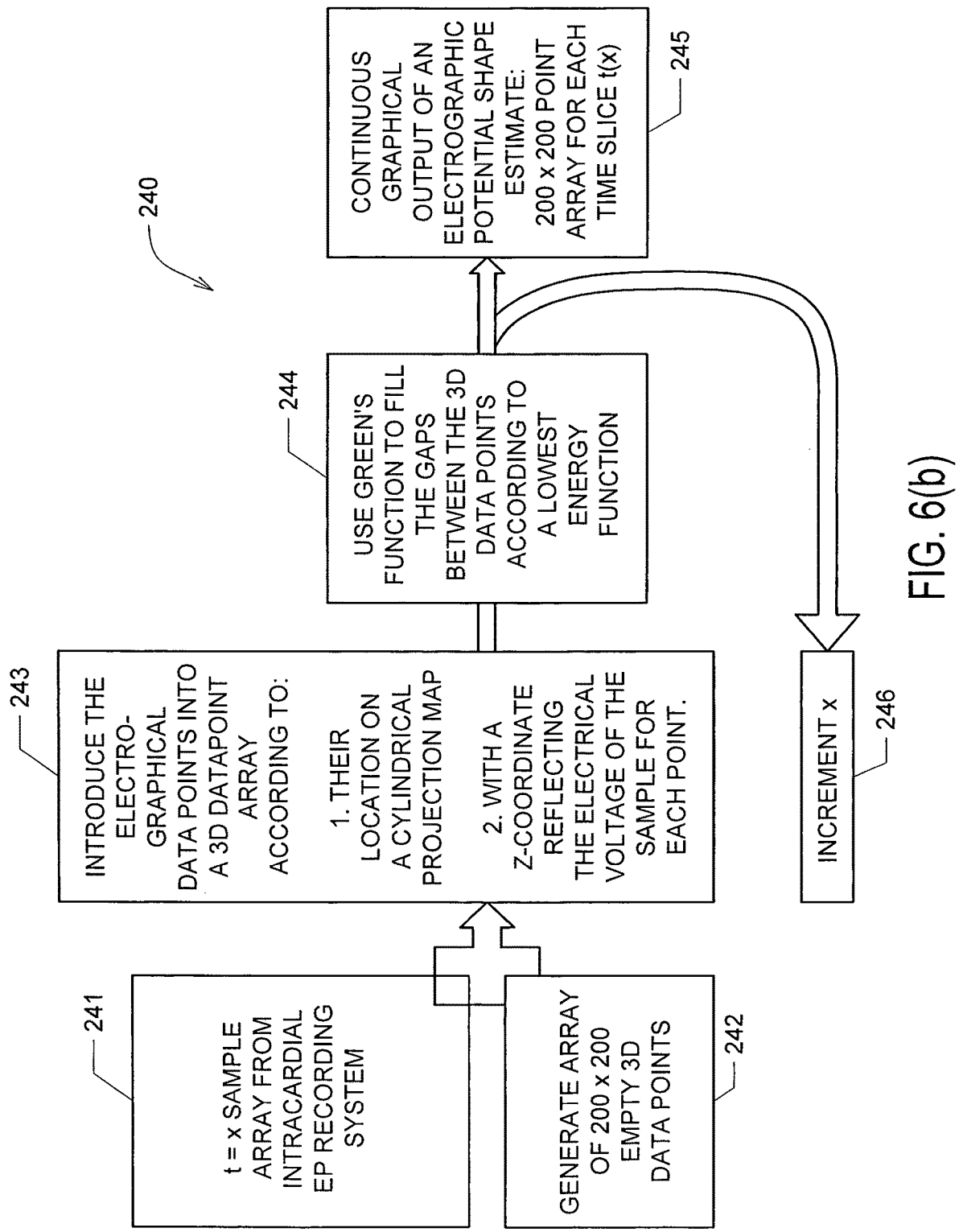
Figure 6C:
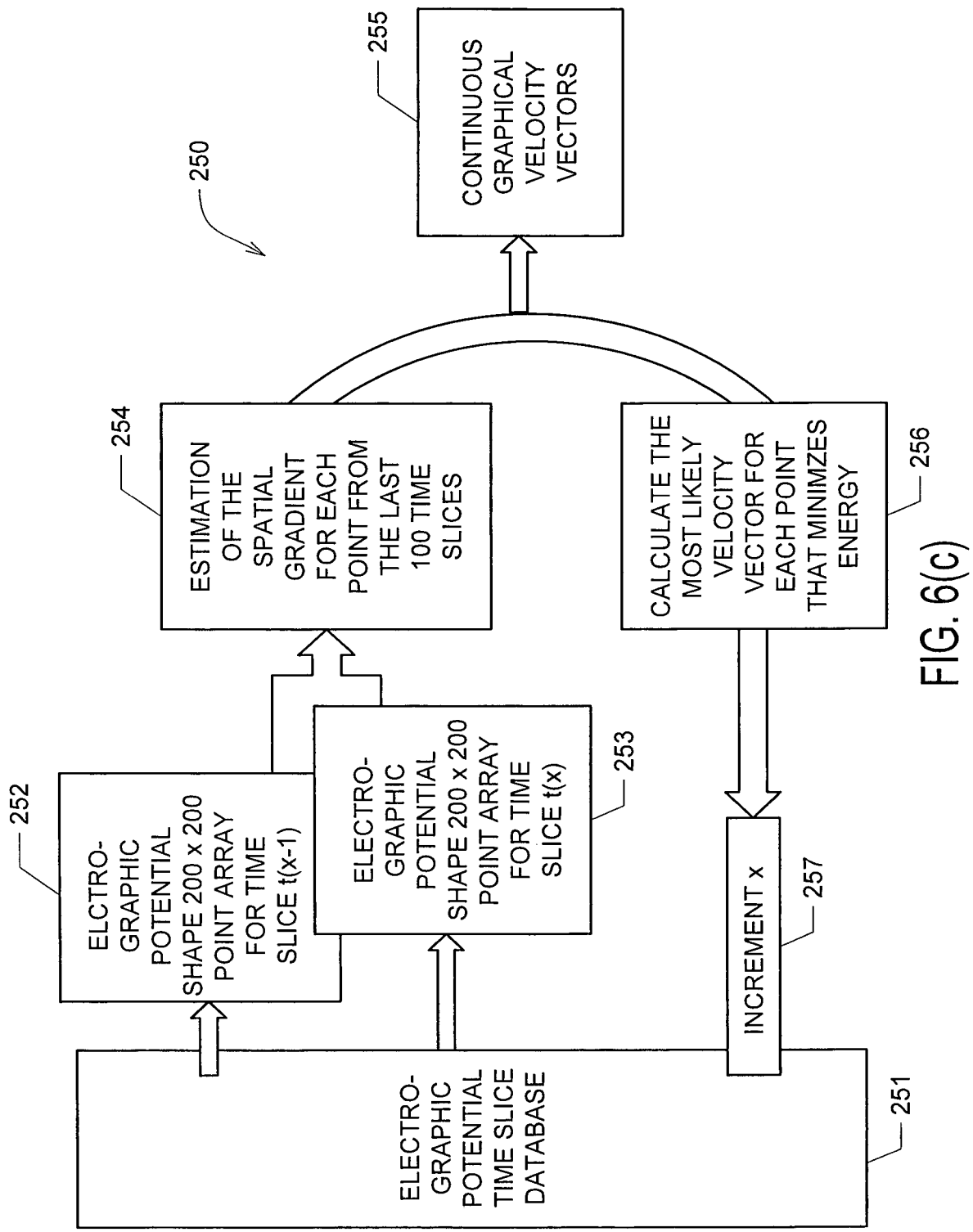
Figure 8A:
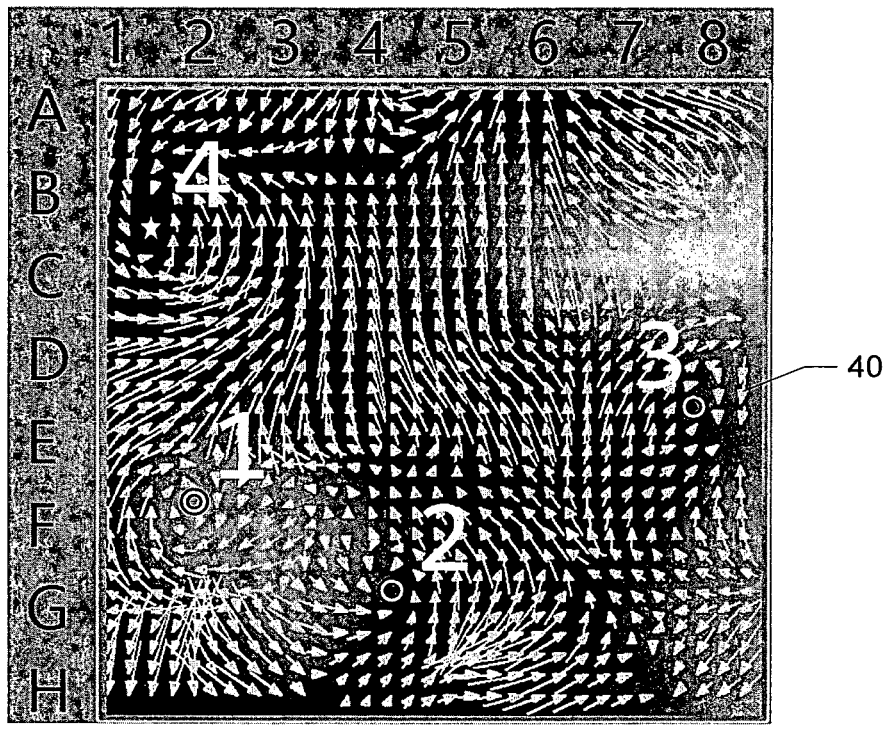
Figure 8B:
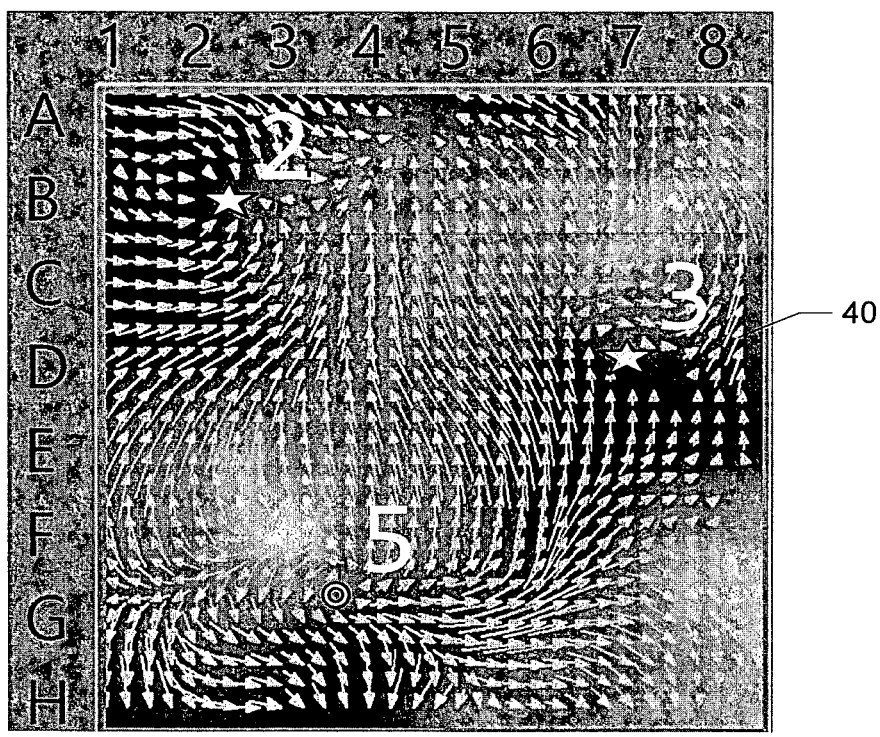
Figure 9:
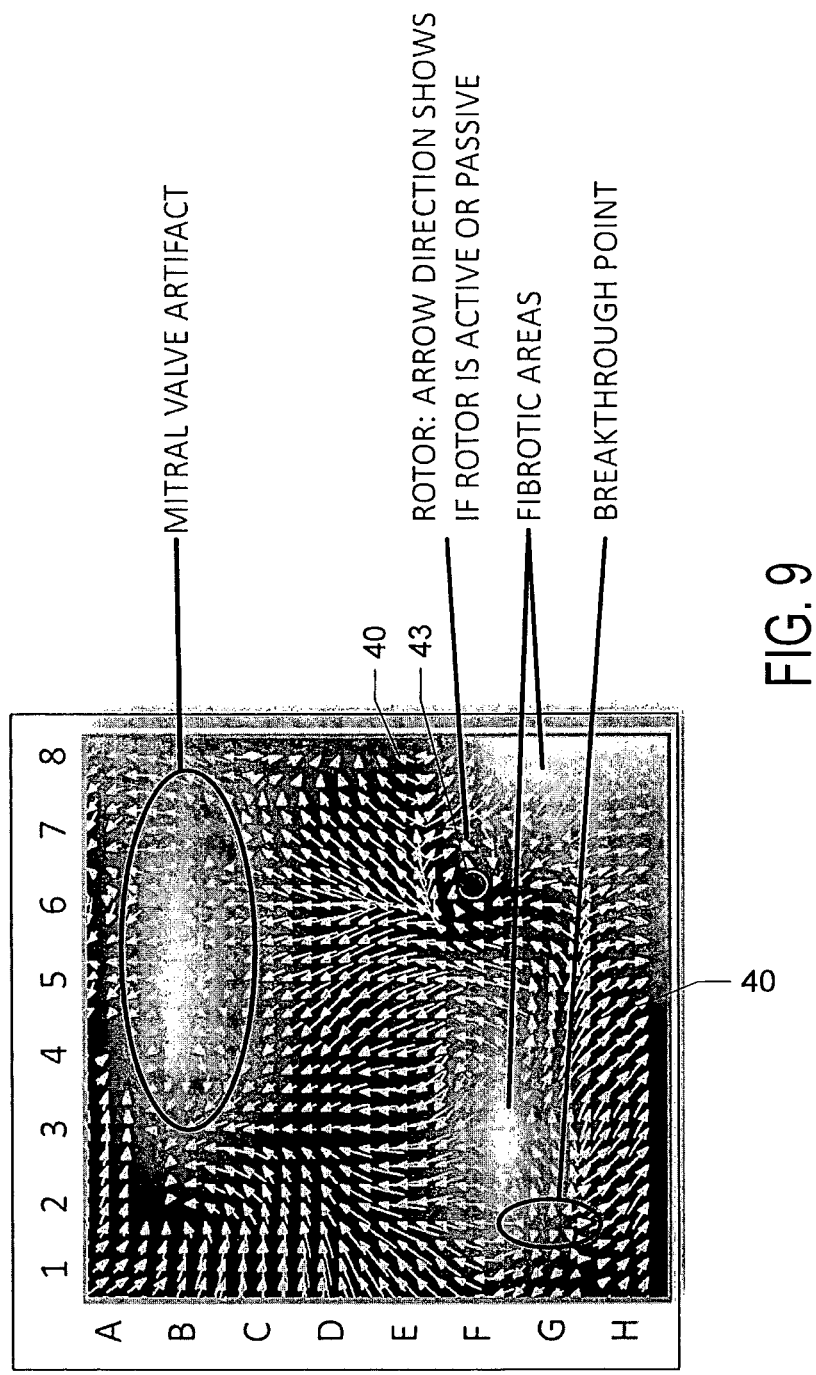
Figure 10D:
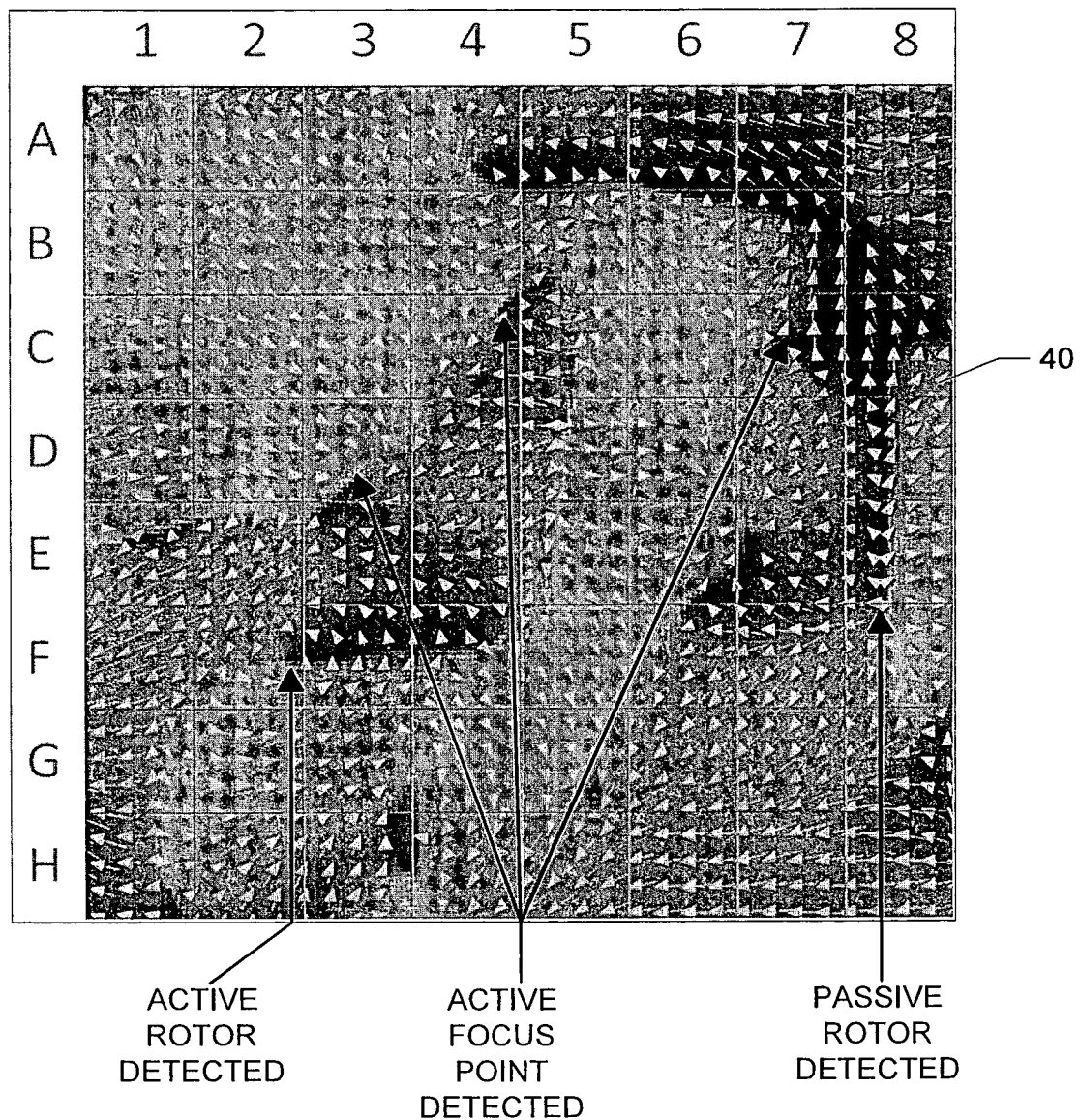
Figure 12A:
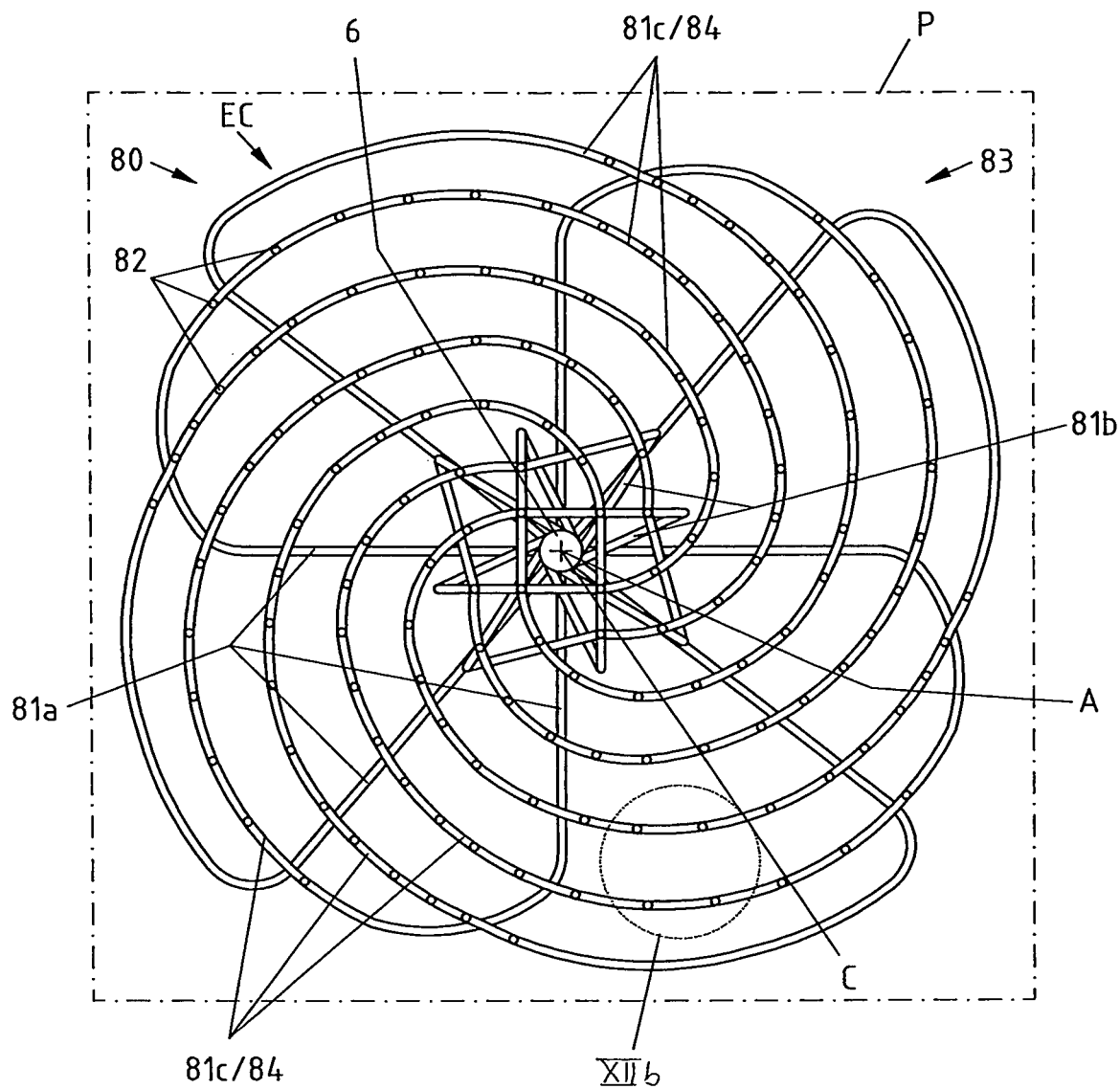
Figure 12B:
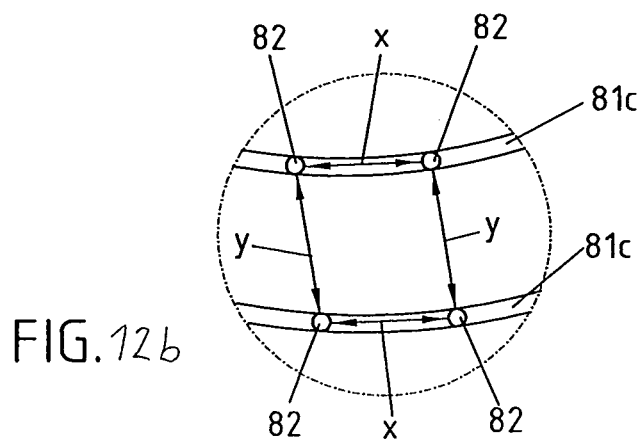
Figure 13:
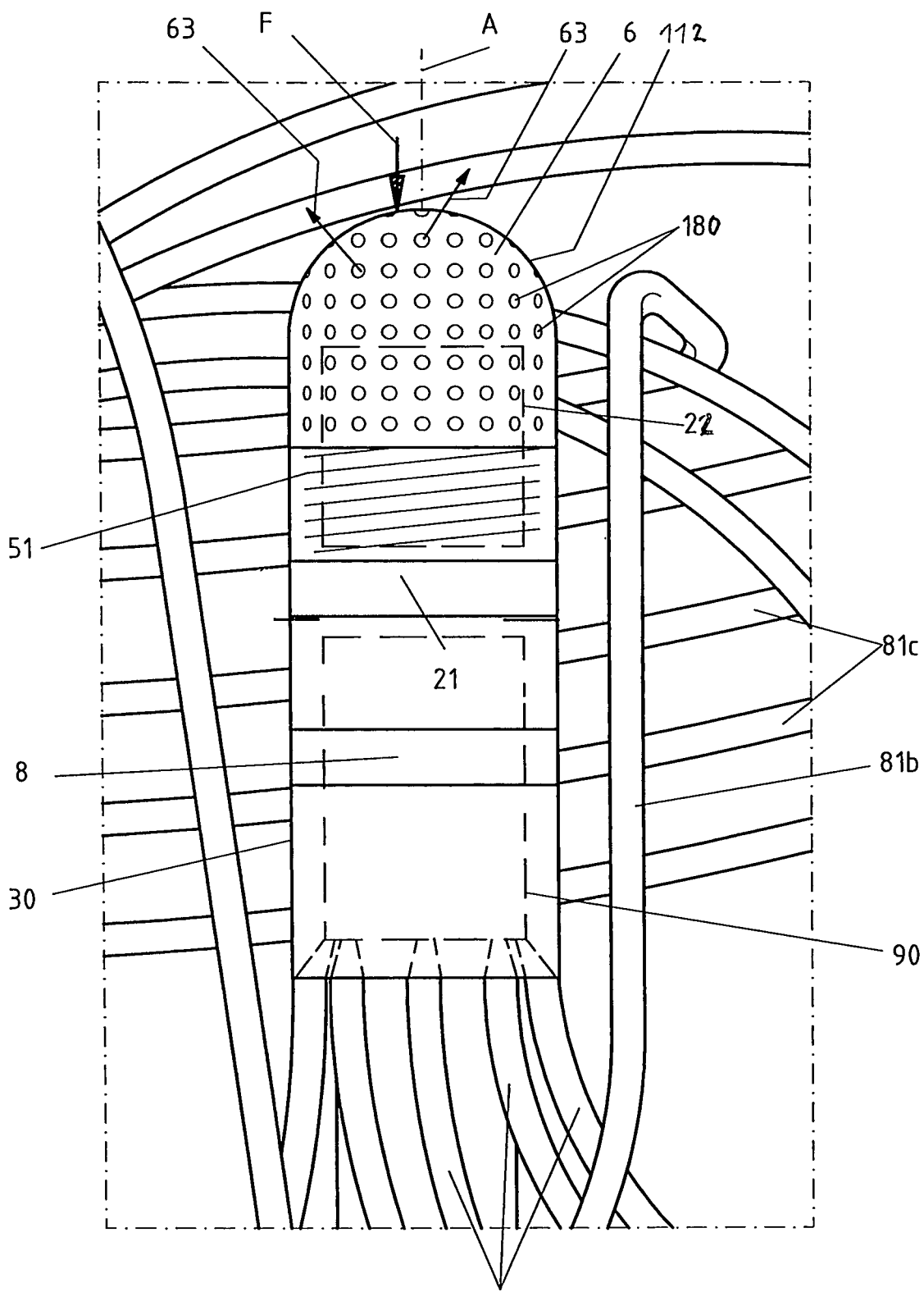
Figure 14A:
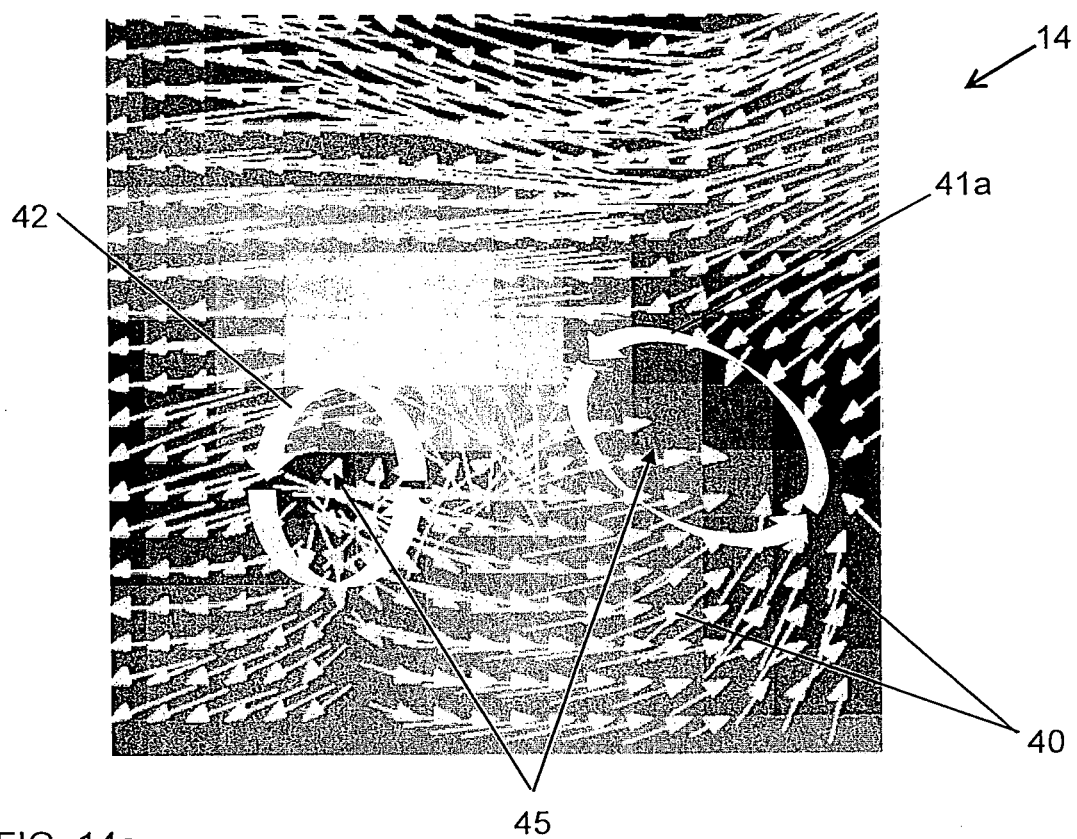
Figure 14B:
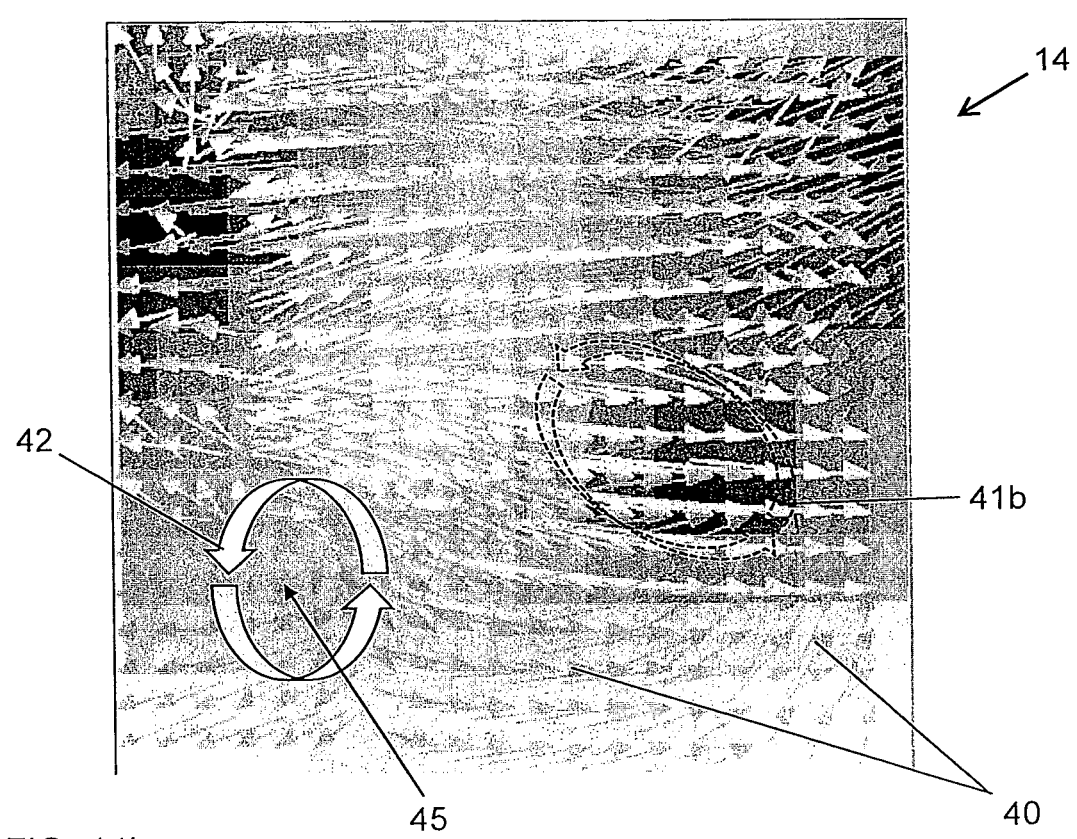

FIGS. 6(a) through 6(c) show details regarding one embodiment of method or algorithm 200 shown in FIG. 4;

FIGS. 7(a) through 7(j) show the results of processing simulated atrial cardiac rhythm disorder data in accordance with one embodiment of method or algorithm 200;

FIGS. 8(a) and 8(b) show velocity vector maps generated from actual patient data using different time windows and method or algorithm 200;

FIG. 9 shows another vector velocity map generated from actual patient data using method or algorithm 200;

FIGS. 10(a) through 10(d) show further results obtained using actual patient data;

FIG. 11 is a perspective view on the distal portion of the elongated medical device according to FIG. 2;

FIG. 12a is a top view of the elongated medical device according to FIG. 2 in the second, expanded condition of the electrode assembly;

FIG. 12b is an enlarged view of an area of the electrode assembly of the elongated medical device of FIG. 12a according to the marking XIIb in FIG. 12a;

FIG. 13 is an enlarged perspective view of the distal end area of the elongated medical device of FIG. 11 in the second, expanded condition of the electrode assembly;

FIG. 14a is a representation of an exemplary visual output on the screen of the data output unit;

FIG. 14b is a representation of a further exemplary visual output on the screen of the data output unit.

The drawings are not necessarily to scale. Like numbers refer to like parts or steps throughout the drawings.

The present invention is directed to systems for analyzing or processing electrophysiological data, especially electrophysiological data in the form of electrogram signals generated or measured by an elongated medical device suitable for intravascular insertion, such as a catheter for exploration or treatment of a vessel, organ or other body cavity or the like medical apparatus. The present invention is also directed to methods for analyzing or processing electrophysiological data, especially electrophysiological data in the form of electrogram signals generated or measured by an elongated medical device suitable for intravascular insertion, such as a catheter (110, 111) for exploration or treatment of a vessel, organ or other body cavity or the like medical apparatus. The catheter (110, 111) includes an electrode assembly (80, 120) for electro-anatomic mapping of cardiac or vessel areas. Various embodiments described and disclosed herein also relate to systems, devices, components and methods for analyzing electrophysiological data to support discovering with enhanced precision the location(s) of the source(s) of different types of cardiac rhythm disorders and irregularities. Such cardiac rhythm disorders and irregularities, include, but are not limited to, arrhythmias, atrial fibrillation (AF or Afib), atrial tachycardia, atrial flutter, paroxysmal fibrillation, paroxysmal flutter, persistent fibrillation, ventricular fibrillation (V-fib), ventricular tachycardia, atrial tachycardia (A-tach), ventricular tachycardia (V-tach), supraventricular tachycardia (SVT), paroxysmal supraventricular tachycardia (PSVT), Wolff-Parkinson-White syndrome, bradycardia, sinus bradycardia, ectopic atrial bradycardia, junctional bradycardia, heart blocks, atrioventricular block, idioventricular rhythm, areas of fibrosis, breakthrough points, focus points, re-entry points, premature atrial contractions (PACs), premature ventricular contractions (PVCs), and other types of cardiac rhythm disorders and irregularities.

Figure 1A:
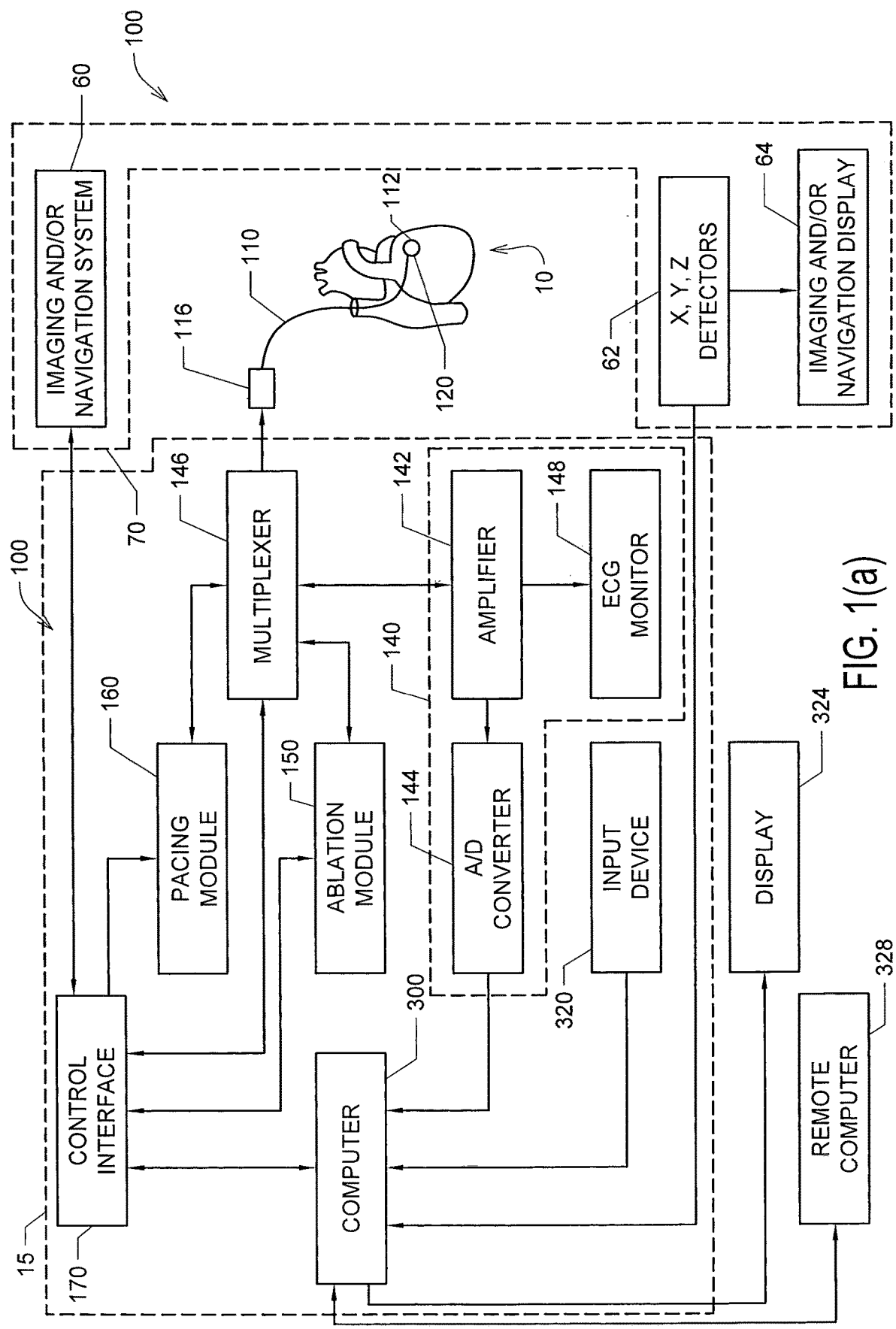
FIG. 1(a) shows one embodiment of a combined cardiac electrophysiological mapping (EP), pacing and ablation system 100.

Referring now to FIG. 1(a), there is illustrated one embodiment of a combined cardiac electrophysiological (EP) mapping, pacing and ablation system 100 including a data processing and control unit 15 which may also be referred to as data acquisition, control and processing system 15. Note that in some embodiments system 100 and data processing and control unit 15 may not include ablation module 150 and/or pacing module 160. Among other things, the embodiment of system 100 shown in FIG. 1(a) is configured to analyze electrophysiological data acquired from a patient's body, e.g. from a patient's heart relating to cardiac rhythm disorders and/or irregularities, and is further configured to detect and discover the location of the source of such cardiac rhythm disorders and/or irregularities with enhanced precision relative to prior art techniques. In some embodiments, system 100 comprises an ablation module 150 which in combination with an ablation catheter or combined mapping and ablation catheter 111 (FIGS. 11-13) may be used to treat the location of the source of the cardiac rhythm disorder or irregularity, for example by ablating the patient's heart at the detected location.

The embodiment of system 100 shown in FIG. 1(a) comprises five main functional units: electrophysiological mapping (EP mapping) unit 140 (which is also referred to herein as data acquisition device 140), ablation module 150, pacing module 160, imaging and/or navigation system 70, and computer or computing device 300.

The data processing and control unit 15 as a main subsystem of the system 100 includes the electrophysiological mapping (EP mapping) unit 140, the pacing module 160, and computer or computing device 300.

In one embodiment, at least one computer or computing device or system 300 is employed to control the operation of one or more of systems, modules and devices 140, 150, 160, 170 and 70. Alternatively, the respective operations of systems, modules or devices 140, 150, 160, 170 and 70 may be controlled separately by each of such systems, modules and devices, or by some combination of such systems, modules and devices.

Computer or computing device 300 may be configured to receive operator inputs from an input device 320 such as a keyboard, mouse and/or control panel. Outputs from computer 300 may be displayed on display or monitor 324 or other output devices (not shown in FIG. 1(a)). Computer 300 may also be operably connected to a remote computer or analytic database or server 328. At least each of components, devices, modules and systems 60, 110, 140, 146, 148, 150, 170, 300, 324 and 328 may be operably connected to other components or devices by wireless (e.g., Bluetooth) or wired means. Data may be transferred between components, devices, modules or systems through hardwiring, by wireless means, or by using portable memory devices such as USB memory sticks.

During electrophysiological (EP) mapping procedures, multi-electrode catheter 110 is typically introduced percutaneously into the patient's heart 10. Catheter 110 is passed through a blood vessel (not shown), such as a femoral vein or the aorta, and thence into an endocardial site such as the atrium or ventricle of the heart 10.

It is contemplated that other catheters (e.g. the catheter of FIGS. 11-13), including other types of mapping or EP catheters, lasso catheters, pulmonary vein isolation (PVI) ablation catheters (which can operate in conjunction with sensing lasso catheters), ablation catheters, navigation catheters, and other types of EP mapping catheters such as EP monitoring catheters and spiral catheters may also be introduced into the heart, and that additional surface electrodes may be attached to the skin of the patient to record electrocardiograms (ECGs).

When system 100 and data processing and control unit 15 is operating in an EP mapping mode, multi-electrode catheter 110 functions as a detector of intra-electrocardiac signals, while optional surface electrodes may serve as detectors of surface ECGs. In one embodiment, the analog signals obtained from the intracardiac and/or surface electrodes 82 are routed by multiplexer 146 to data acquisition device 140, which comprises an amplifier 142 and an A/D converter (ADC) 144. The amplified or conditioned electrogram signals may be displayed by electrocardiogram (ECG) monitor 148. The analog signals are also digitized via ADC 144 and input into computer 300 for data processing, analysis and graphical display.

In one embodiment, catheter 110 is configured to detect cardiac activation information in the patient's heart 10, and to transmit the detected cardiac activation information to data acquisition device 140, either via a wireless or wired connection. In one embodiment that is not intended to be limiting with respect to the number, arrangement, configuration, or types of electrodes, catheter 110 includes a plurality of 64 electrodes 82 (having n=64 electrodes), probes and/or sensors A1 through H8 arranged in an 8×8 grid (an $n_x \times n_y = 8 \times 8$ grid) that are included in electrode mapping assembly 120, which is configured for insertion into the patient's heart through the patient's blood vessels and/or veins. Other numbers, arrangements, configurations and types of electrodes 82 in catheter 110 are, however, also contemplated. In most of the various embodiments, at least some electrodes, probes and/or sensors included in catheter 110 are configured to detect cardiac activation or electrical signals, and to generate electrocardiograms or electrogram signals, which are then relayed by electrical conductors from or near the distal end 112 of catheter 110 to proximal end 116 of catheter 110 to data acquisition device 140 of the data processing and control unit 15/the system 100.

Note that in some embodiments of system 100, multiplexer 146 is not employed for various reasons, such as sufficient electrical conductors being provided in catheter 110 for all electrode channels, or other hardware design considerations. In other embodiments, multiplexer 146 is incorporated into catheter 110 or into data acquisition device 140.

In one embodiment, a medical practitioner or health care professional employs catheter 110 as a roving catheter to locate the site of the location of the source of a cardiac rhythm disorder or irregularity in the endocardium quickly and accurately, without the need for open-chest and open-heart surgery. In one embodiment, this is accomplished by using multi-electrode catheter 110 in combination with real-time or near-real-time data processing and interactive display by computer 300, and optionally in combination with imaging and/or navigation system 70. In one embodiment, multi-electrode catheter 110 deploys at least a two-dimensional array of electrodes 82 against a site of the endocardium at a location that is to be mapped, such as through the use of a Biosense Webster® PENTARAY® EP mapping catheter. The intracardiac or electrogram signals detected by the catheter's electrodes 82 provide data sampling of the electrical activity in the local site spanned by the array of electrodes 82.

In one embodiment, the electrogram signal data are processed by computer 300 to produce a display showing the locations(s) of the source(s) of cardiac rhythm disorders such as rotors and/or irregularities in the patient's heart 10 in real-time or near-real-time, further details of which are provided below. That is, at and between the sampled locations of the patient's endocardium, computer 300 may be configured to compute and display in real-time or near-real-time an estimated, detected and/or determined location(s) of the site(s), source(s) or origin)s) of the cardiac rhythm disorder(s) and/or irregularity(s) within the patient's heart 10. This permits a medical practitioner to move interactively and quickly the electrodes 82 of catheter 110 towards the location of the source of the cardiac rhythm disorder or irregularity. The electrogram signals or electrogram signal data may be stored in a memory for later processing with the system 100/the data processing and control unit 15. This means, that the data analysis of the electrogram signals is not restricted to a direct/simultaneous processing when the data are acquired but also to a subsequent processing by the system 100/the data processing and control unit 15.

In some embodiments of system 100, one or more electrodes, sensors or probes detect cardiac activation from the surface of the patient's body as surface ECGs, or remotely without contacting the patient's body (e.g., using magneto-cardiograms). In another example, some electrodes, sensors or probes may derive cardiac activation information from echocardiograms. In various embodiments of system 100, external or surface electrodes, sensors and/or probes can be used separately or in different combinations, and further may also be used in combination with intracardiac electrodes, sensors and/or probes inserted within the patient's heart 10. Many different permutations and combinations of the various components of system 100 are contemplated having, for example, reduced, additional or different numbers of electrical sensing and other types of electrodes, sensors and/or transducers.

Continuing to refer to FIG. 1(*a*), EP mapping system or data acquisition device 140 is configured to condition the analog electrogram signals delivered by catheter 110 from electrodes 82—A1 through H8 in amplifier 142. Conditioning of the analog electrogram signals received by amplifier 142 may include, but is not limited to, low-pass filtering, high-pass filtering, bandpass filtering, and notch filtering. The conditioned analog signals are then digitized in analog-to-digital converter (ADC) 144. ADC 144 may further include a digital signal processor (DSP) or other type of processor which is configure to further process the digitized electrogram signals (e.g., low-pass filter, high-pass filter, bandpass filter, notch filter, automatic gain control, amplitude adjustment or normalization, artifact removal, etc.) before they are transferred to computer or computing device 300 for further processing and analysis.

As discussed above, in some embodiments, multiplexer 146 is separate from catheter 110 and data acquisition device 140, and in other embodiments multiplexer 146 is combined in catheter 110 (or catheter 111 described below with reference to FIGS. 11-13) or data acquisition device 140.

In some embodiments, the rate at which individual electrogram and/or ECG signals are sampled and acquired by system 100 can range between about 0.25 milliseconds and about 8 milliseconds, and may be about 0.5 milliseconds, about 1 millisecond, about 2 milliseconds or about 4 milliseconds. Other sample rates are also contemplated. While in some embodiments system 100 is configured to provide unipolar signals, in other embodiments system 100 is configured to provide bipolar signals.

In one embodiment, system 100 can include a BARD® LABSYSTEM™ PRO EP Recording System, which is a computer and software driven data acquisition and analysis tool designed to facilitate the gathering, display, analysis, pacing, mapping, and storage of intracardiac EP data. Also in one embodiment, data acquisition device 140 can include a BARD® CLEARSIGN™ amplifier, which is configured to amplify and condition electrocardiographic signals of biologic origin and pressure transducer input, and transmit such information to a host computer (e.g., computer 300 or another computer).

As shown in FIG. 1(*a*), and as described above, in some embodiments system 100 includes ablation module 150, which may be configured to deliver RF ablation energy through catheter 110 and corresponding ablation electrodes disposed near distal end 112 thereof, and/or to deliver RF ablation energy through a different catheter (not shown in FIG. 1(*a*)). Suitable ablation systems and devices include, but are not limited to, cryogenic ablation devices and/or systems, radiofrequency ablation devices and/or systems, ultrasound ablation devices and/or systems, high-intensity focused ultrasound (HIFU) devices and/or systems, chemical ablation devices and/or systems, and laser ablation devices and/or systems.

When system 100 is operating in an optional ablation mode, multi-electrode catheter 110 fitted with ablation electrodes, or a separate ablation catheter, is energized by ablation module 150 under the control of computer 300, control interface 170, and/or another control device or module. For example, an operator may issue a command to ablation module 150 through input device 320 to computer 300. In one embodiment, computer 300 or another device controls ablation module 150 through control interface 170. Control of ablation module 150 can initiate the delivery of a programmed series of electrical energy pulses to the endocardium via catheter 110 (or a separate ablation catheter, not shown in FIG. 1(*a*)). One embodiment of an ablation method and device is disclosed in U.S. Pat. No. 5,383,917 to Desai et al., the entirety of which is hereby incorporated by reference herein.

In an alternative embodiment, ablation module 150 is not controlled by computer 300, and is operated manually directly under operator control. Similarly, pacing module 160 may also be operated manually directly under operator control. The connections of the various components of system 100 to catheter 110, to auxiliary catheters, or to surface electrodes may also be switched manually or using multiplexer 146 or another device or module.

When system 100 is operating in an optional pacing mode, multi-electrode catheter 110 is energized by pacing module 160 operating under the control of computer 300 or another control device or module. For example, an operator may issue a command through input device 320 such that computer 300 controls pacing module 160 through control interface 170, and multiplexer 146 initiates the delivery of a programmed series of electrical simulating pulses to the endocardium via the catheter 110 or another auxiliary catheter (not shown in FIG. 1(*a*)). One embodiment of a pacing module is disclosed in M. E. Josephson et al., in "VENTRICULAR ENDOCARDIAL PACING II, The Role of Pace Mapping to Localize Origin of Ventricular Tachycardia," The American Journal of Cardiology, vol. 50, November 1982.

Computing device or computer 300 of the data processing and control unit 15 is appropriately configured and programmed to receive or access the electrogram signals provided by data acquisition device 140. Computer 300 is further configured to analyze or process such electrogram signals in accordance with the methods, functions and logic disclosed and described herein so as to permit reconstruction of cardiac activation information from the electrogram signals. This, in turn, makes it possible to locate with at least some reasonable degree of precision the location of the source of a heart rhythm disorder or irregularity. Once such a location has been discovered, the source may be eliminated or treated by means that include, but are not limited to, cardiac ablation.

In one embodiment, and as shown in FIG. 1(*a*), system 100 also comprises a physical imaging and/or navigation system 70. Physical imaging and/or navigation device 60 included in system 70 may be, by way of example, a 2- or 3-axis fluoroscope system, an ultrasonic system, a magnetic resonance imaging (MRI) system, a computed tomography (CT) imaging system, and/or an electrical impedance tomography EIT) system. Operation of system 70 be controlled by computer 300 via control interface 170, or by other control means incorporated into or operably connected to imaging or navigation system 70. In one embodiment, computer 300 or another computer triggers physical imaging or navigation system 60 to take "snap-shot" pictures of the heart 10 of a patient (body not shown). A picture image is detected by a detector 62 along each axis of imaging, and can include a silhouette of the heart as well as a display of the inserted catheter 110 and its electrodes 82 A1-H8 (more about which is said below), which is displayed on imaging or navigation display 64. Digitized image or navigation data may be provided to computer 300 for processing and integration into computer graphics that are subsequently displayed on a data output device such as monitor or display 64 and/or 324.

In one embodiment, system 100 further comprises or operates in conjunction with catheter or electrode position transmitting and/or receiving coils or antennas located at or near the distal end of an EP mapping catheter 110, or that of an ablation or navigation catheter 110, which are configured to transmit electromagnetic signals for intra-body navigational and positional purposes.

In one embodiment, imaging or navigation system 70 is used to help identify and determine the precise two- or three-dimensional positions of the various electrodes included in catheter 110 within patient's heart 10, and is configured to provide electrode position data to computer 300. Electrodes, position markers, and/or radio-opaque markers can be located on various portions of catheter 110, mapping electrode assembly 120 and/or distal end 112, or can be configured to act as fiducial markers for imaging or navigation system 70.

Medical navigation systems suitable for use in the various embodiments described and disclosed herein include, but are not limited to, image-based navigation systems, model-based navigation systems, optical navigation systems, electromagnetic navigation systems (e.g., BIOSENSE® WEBSTER® CARTO® system), and impedance-based navigation systems (e.g., the St. Jude® ENSITE™ VELOCITY™ cardiac mapping system), and systems that combine attributes from different types of imaging AND navigation systems and devices to provide navigation within the human body (e.g., the MEDTRONIC® STEALTHSTATION® system).

In view of the structural and functional descriptions provided herein, those skilled in the art will appreciate that portions of the described devices and methods may be configured as methods, data processing systems, or computer algorithms. Accordingly, these portions of the devices and methods described herein may take the form of a hardware embodiment, a software embodiment, or an embodiment combining software and hardware, such as shown and described with respect to computer system 300 illustrated in FIG. 1(*b*). Furthermore, portions of the devices and methods described herein may be a computer algorithm stored in a computer-usable storage medium having computer readable program code on the medium. Any suitable computer-readable medium may be utilized including, but not limited to, static and dynamic storage devices, hard disks, optical storage devices, and magnetic storage devices.

Certain embodiments of portions of the devices and methods described herein are also described with reference to block diagrams of methods, systems, and computer algorithm products. It will be understood that such block diagrams, and combinations of blocks diagrams in the Figures, can be implemented using computer-executable instructions. These computer-executable instructions may be provided to one or more processors of a general purpose computer, a special purpose computer, or any other suitable programmable data processing apparatus (or a combination of devices and circuits) to produce a machine, such that the instructions, which executed via the processor(s), implement the functions specified in the block or blocks of the block diagrams.

These computer-executable instructions may also be stored in a computer-readable memory that can direct computer 300 or other programmable data processing apparatus to function in a particular manner, such that the instructions stored in the computer-readable memory result in an article of manufacture including instructions which implement the function specified in an individual block, plurality of blocks, or block diagram. The computer program instructions may also be loaded onto computer 300 or other programmable data processing apparatus to cause a series of operational steps to be performed on the computer or other programmable apparatus to produce a computer implemented process such that the instructions which execute on computer 300 or other programmable apparatus provide steps for implementing the functions specified in an individual block, plurality of blocks, or block diagram.

Figure 1B:
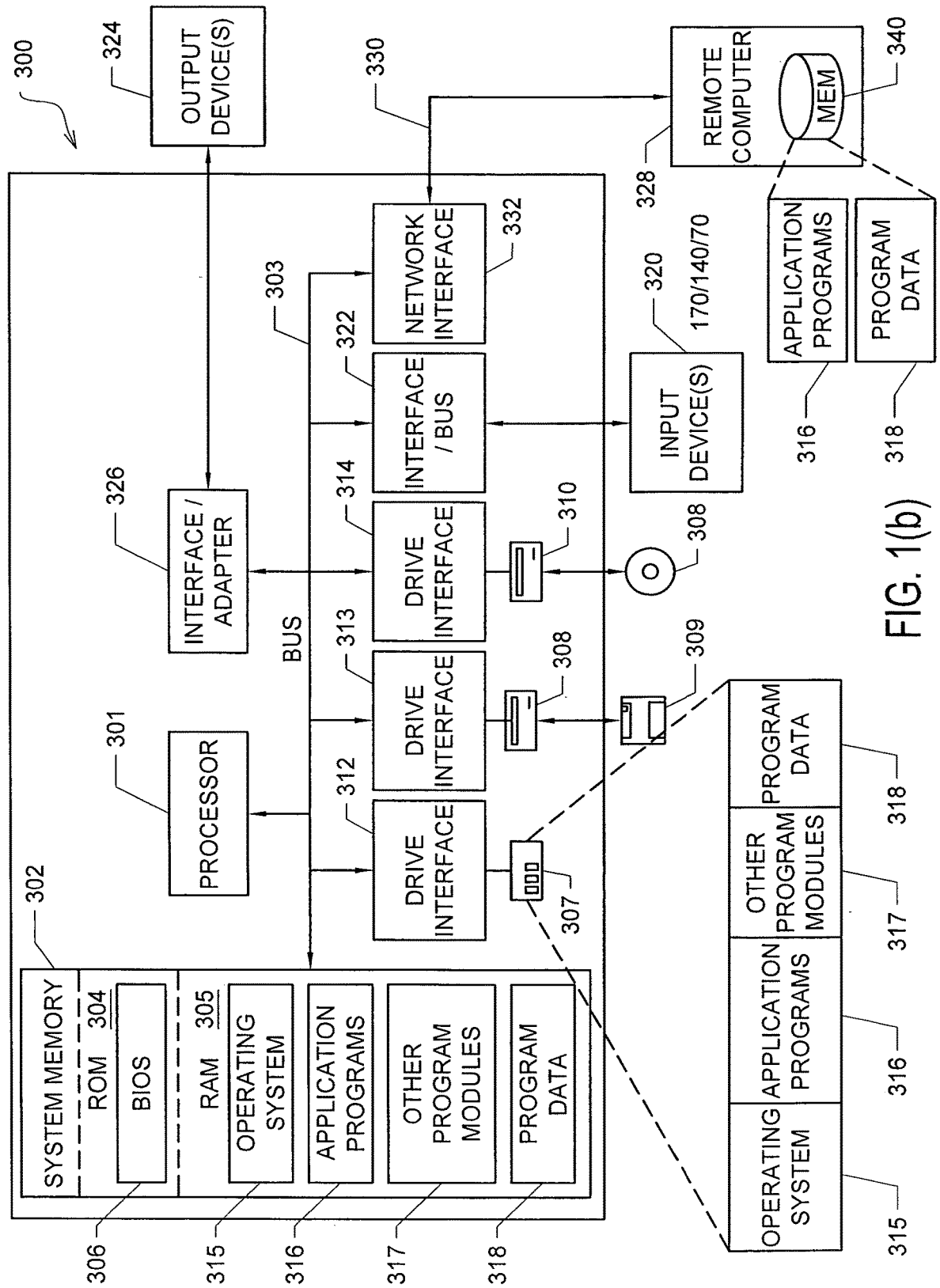
FIG. 1(b) shows one embodiment of a computer system 300.

In this regard, FIG. 1(b) illustrates only one example of a computer system 300 (which, by way of example, can include multiple computers or computer workstations) that can be employed to execute one or more embodiments of the devices and methods described and disclosed herein, such as devices and methods configured to acquire and process sensor or electrode data, to process image data, and/or transform sensor or electrode data and image data associated with the analysis of cardiac electrical activity and the carrying out of the combined electrophysiological mapping and analysis of the patient's heart 10 and ablation therapy delivered thereto.

Computer system 300 can be implemented on one or more general purpose computer systems or networked computer systems, embedded computer systems, routers, switches, server devices, client devices, various intermediate devices/nodes or standalone computer systems. Additionally, computer system 300 or portions thereof may be implemented on various mobile devices such as, for example, a personal digital assistant (PDA), a laptop computer and the like, provided the mobile device includes sufficient processing capabilities to perform the required functionality.

In one embodiment, computer system 300 includes processing unit 301 (which may comprise a CPU, controller, microcontroller, processor, microprocessor or any other suitable processing device), system memory 302, and system bus 303 that operably connects various system components, including the system memory, to processing unit 301. Multiple processors and other multi-processor architectures also can be used to form processing unit 301. System bus 303 can comprise any of several types of suitable bus architectures, including a memory bus or memory controller, a peripheral bus, or a local bus. System memory 302 can include read only memory (ROM) 304 and random access memory (RAM) 305. A basic input/output system (BIOS) 306 can be stored in ROM 304 and contain basic routines configured to transfer information and/or data among the various elements within computer system 300.

Computer system 300 can include a hard disk drive 303, a magnetic disk drive 308 (e.g., to read from or write to removable disk 309), or an optical disk drive 310 (e.g., for reading CD-ROM disk 311 or to read from or write to other optical media). Hard disk drive 303, magnetic disk drive 308, and optical disk drive 310 are connected to system bus 303 by a hard disk drive interface 312, a magnetic disk drive interface 313, and an optical drive interface 314, respectively. The drives and their associated computer-readable media are configured to provide nonvolatile storage of data, data structures, and computer-executable instructions for computer system 300. Although the description of computer-readable media above refers to a hard disk, a removable magnetic disk and a CD, other types of media that are readable by a computer, such as magnetic cassettes, flash memory cards, digital video disks and the like, in a variety of forms, may also be used in the operating environment; further, any such media may contain computer-executable instructions for implementing one or more parts of the devices and methods described and disclosed herein.

A number of program modules may be stored in drives and RAM 303, including operating system 315, one or more application programs 316, other program modules 313, and program data 318. The application programs and program data can include functions and methods programmed to acquire, process and display electrical data from one or more sensors, such as shown and described herein. The application programs and program data can include functions and methods programmed and configured to process data acquired from a patient, e.g. for assessing heart function, such as shown and described herein with respect to FIGS. 1-10(f).

A health care provider or other user may enter commands and information into computer system 300 through one or more input devices 320, such as a pointing device (e.g., a mouse, a touch screen, etc.), a keyboard, a microphone, a joystick, a game pad, a scanner, and the like. For example, the user can employ input device 320 to edit or modify the data being input into a data processing algorithm (e.g., only data corresponding to certain time slices or intervals). These and other input devices 320 may be connected to processing unit 301 through a corresponding input device interface or port 322 that is operably coupled to the system bus, but may be connected by other interfaces or ports, such as a parallel port, a serial port, or a universal serial bus (USB). One or more output devices 324 (e.g., display, a monitor, a printer, a projector, or other type of display device) may also be operably connected to system bus 303 via interface 326, such as through a video adapter.

Computer system 300 may operate in a networked environment employing logical connections to one or more remote computers, such as remote computer 328. Remote computer 328 may be a workstation, a computer system, a router, or a network node, and may include connections to many or all the elements described relative to computer system 300. The logical connections, schematically indicated at 330, can include a local area network (LAN) and/or a wide area network (WAN).

When used in a LAN networking environment, computer system 300 can be connected to a local network through a network interface or adapter 332. When used in a WAN networking environment, computer system 300 may include a modem, or may be connected to a communications server on the LAN. The modem, which may be internal or external, can be connected to system bus 303 via an appropriate port interface. In a networked environment, application programs 316 or program data 318 depicted relative to computer system 300, or portions thereof, may be stored in a remote memory storage device 340.

Referring now to FIG. 2, there is shown an illustrative view of one embodiment of a distal portion of catheter 110 inside a patient's left atrium 14. As shown in FIG. 2, heart 10 includes right atrium 12, left atrium 14, right ventricle 18, and left ventricle 20. Mapping electrode assembly 120 is shown in an expanded or open state inside left atrium 13 after it has been inserted through the patient's inferior vena cava and foramen ovalen ("IVC" and "FO" in FIG. 2), and is configured to obtain electrogram signals from left atrium 12 via an 8×8 array of electrodes 82 A1 through H8 (with n=64 electrodes in a $n_y \times n_x$ 8×8 electrode grid). Mapping electrode assembly 120 and catheter 110 may also be positioned with the patient's right atrium 12, left ventricle 18 and right ventricle 20.

Figure 3:
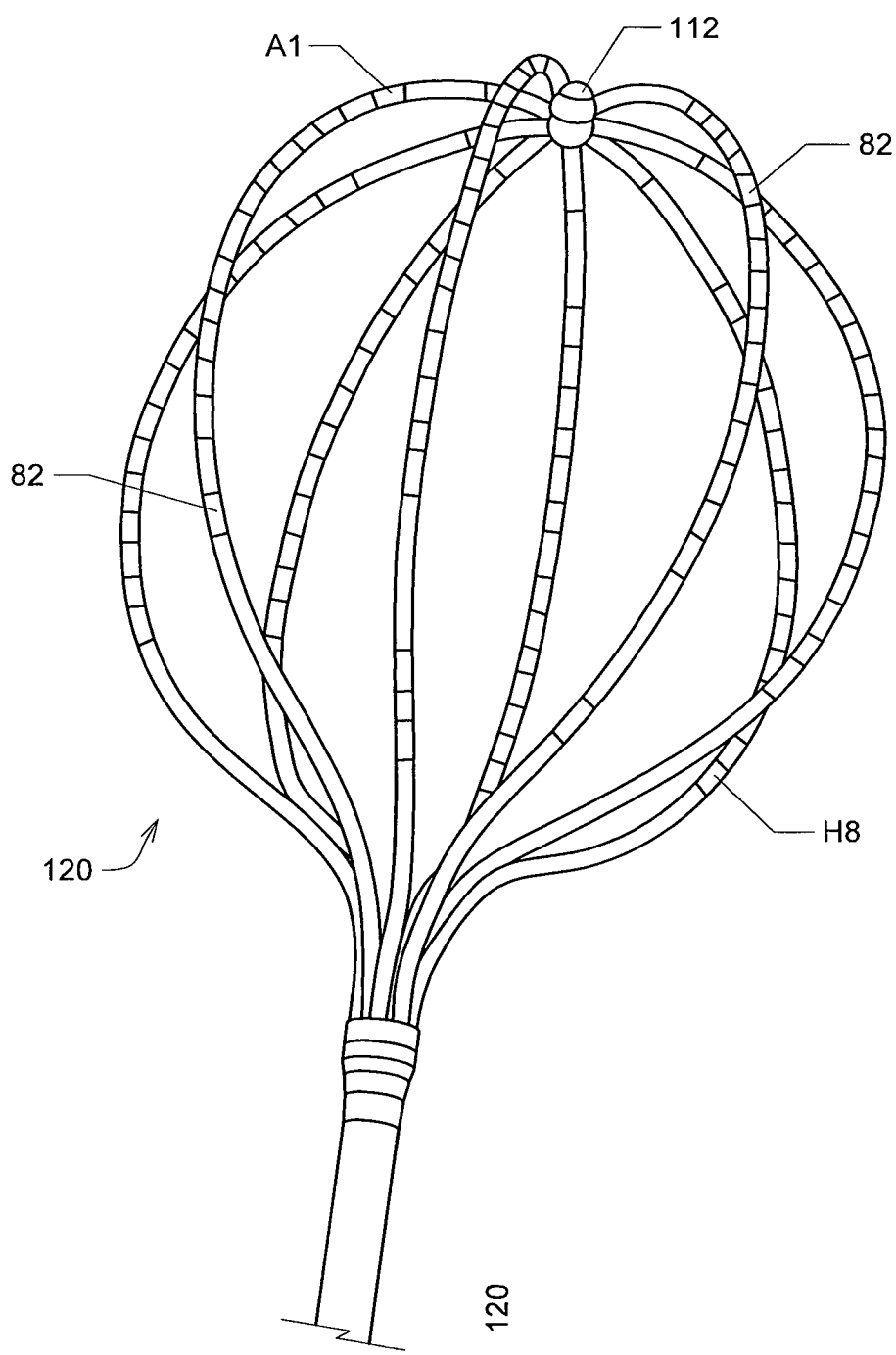
FIG. 3 shows an illustrative embodiment of a mapping electrode assembly 120 of catheter 110 of FIG. 2.

FIG. 3 shows an illustrative embodiment of a mapping electrode assembly 120, which in FIG. 3 forms a distal portion of a Boston Scientific® CONSTELLATION® full contact mapping catheter. The CONSTELLATION EP catheter permits full-contact mapping of a patient's heart chamber, and may also be employed to facilitate the assessment of entrainment, conduction velocity studies, and refractory period in a patient's heart 10. Mapping electrode assembly 120 shown in FIG. 3 permits the simultaneous acquisition of longitudinal and circumferential signals for more accurate 3-D mapping, and features a flexible basket design that conforms to atrial anatomy and aids aid in accurate placement. Sixty-four electrodes A1 through H8 can provide comprehensive, real-time 3-D information over a single heartbeat.

FIG. 4 shows one embodiment of a method 200 of detecting a location of a source of at least one cardiac rhythm disorder in a patient's heart. At step 210, the amplitudes of electrogram signals acquired from electrodes 82 located inside a patient's heart, e.g., electrodes 82 included in a mapping electrode assembly 120, are normalized and/or adjusted. At step 230, positions A1 through H8 corresponding to each of the electrodes 82 of mapping electrode assembly 120 are assigned to the individual electrogram signals that have been acquired. At step 230, a two-dimensional (2D) spatial map of electrode positions A1 through H8 is generated or provided. In some embodiments, a three-dimensional (3D) spatial map of electrode positions A1 through H8 is generated or provided. (As discussed above, fewer or more than 64 electrodes 82 may be used to measure electrogram signals and/or surface ECGs, and electrode arrays other than 8×8 or rectangular grids are contemplated in the various embodiments.)

For discrete or selected times over which the electrogram signals are being analyzed and processed, at step 240 the amplitude-adjusted electrogram signals are processed across the 2D (or 3D) map to generate a plurality of three-dimensional electrogram surfaces (which according to one embodiment may be smoothed electrogram surfaces), one surface being generated for each such discrete time. At step 250, the plurality of three-dimensional electrogram surfaces that have been generated across the 2D (or 3D) map through time are processed to generate a velocity vector map. The velocity vector map is configured to reveal the location of the source of the at least one cardiac rhythm disorder. In a subsequent optional step (not shown in FIG. 4), method 200 further comprises ablating patient's heart 10 at the location of the source of the cardiac rhythm disorder indicated by the velocity vector map.

Algorithm 200 outlined in FIG. 4 presents one embodiment of a method of processing electrogram signals provided by one or more mapping catheters so as to transform time domain waveform information into space domain information, and then calculate velocity vector maps that correspond to normalized space potential profile movements for each point in space. For reasons that are explained below, algorithm 200 has the advantages that it is robust against artifacts and provides a virtual resolution that is higher than the actual electrode density employed to acquire the EP mapping data through the use of a fitting algorithm that determines the most likely mean spatial velocity map derived from hundreds of individual samples of amplitude patterns recorded by the mapping electrodes.

As described above, in step 210 of FIG. 4 the amplitudes of electrogram signals acquired from electrodes located inside the patient's heart are normalized or otherwise adjusted. In step 240, the amplitude-adjusted electrogram signals are processed across a 2D or 3D map to generate a plurality of three-dimensional electrogram surfaces, one surface being generated for each such discrete time. In one embodiment, the resulting individual time-slice surfaces can be strung together sequentially to provide a time-varying depiction of electrical activation occurring over the portion of the patient's heart that has been monitored. According to embodiments that have been discovered to be particularly efficacious in the field of intracardiac EP monitoring and data processing and analysis, at least portions of the electrogram surfaces are found to correspond to estimated wave shapes, and are generated using Green's function, which in some embodiments, and by way of non-limiting example, may be combined with two- or three-dimensional bi-harmonic spline interpolation functions to generate such surfaces.

In one embodiment, electrogram signal data acquired from the patient's heart 10 are not equidistantly sampled. For example, in one such embodiment, electrogram signal data acquired from the patient's heart 10 are not equidistantly sampled by mapping electrode assembly 120, and instead are assigned their respective chessboard locations A1 through H8 as approximations of electrode locations in a cylindrical 2D projection of a grid representative of the interior surface of the patient's heart that is being mapped. In many applications, it has been discovered that such approximations of electrode locations yield perfectly useable and accurate results when steps 230 through 250 are carried out after steps 210 and 230.

In another embodiment, when superimposing the acquired electrogram signal data onto a 2D or 3D map or grid in step 230, the electrogram signal data may be associated with their actual or more accurately estimated positions in the 2D projection of the grid using positional data provided by, for example, imaging or navigation system 70. Resampling of electrogram signals on the grid may also be carried out. Gridding may also be carried out such as by convolution-type filtering, Kriging, and using splines. Most gridding techniques operate on an equidistant grid and solve the equations governing the gridding process with either finite difference or finite element implementations.

One approach that has been discovered to work particularly well with electrogram signal data is to determine the Green's function associated with each electrogram value assigned to a given chessboard location, and then construct the solution as a sum of contributions from each data point, weighted by the Green's function evaluated for each point of separation. Biharmonic spline interpolation, which is based on Green's function, has also been discovered to work especially well in the context of processing and analyzing electrogram signal data. In some embodiments, undesirable oscillations between data points are removed by interpolation with splines in tension based on Green's function. By doing so, virtual amplitudes of virtual electrogram signals are generated in between the electrogram signals of neighboring electrodes 82 in the $n_x$, $n_y$ grid of electrodes 82 for each determined time interval or time slice. The total number $n_y$ of virtual electrogram signals is at least 10 times, preferably 10-100 times, more preferably 20-40 times the total number n of measured electrogram signals and wherein the virtual amplitude value of a virtual electrogram signal located in between two neighboring electrogram signals is defined to be the average of the amplitude values of the neighboring electrogram signals. The neighboring electrogram signals may be either one of measured or virtual electrogram signals.

A Green's function technique for interpolation and surface fitting and generation of electrogram signal data has been found to be superior to conventional finite-difference methods because, among other things, the model can be evaluated at arbitrary x,y locations rather than only on a rectangular grid. This is a very important advantage of using Green's function in step 240, because precise evenly-spaced-apart grid locations, resampling of electrogram signals, and finite-difference gridding calculations are not required to generate accurate representations of electrogram surfaces in step 244.

In one embodiment, Green's function G(x; x') is employed in step 240 for a chosen spline and geometry to interpolate data at regular or arbitrary output locations. Mathematically, the solution is w(x)=sum {c(i) G(x'; x(i))}, for i=1, n, and a number of data points {x(i), w(i)}. Once the n coefficients c(i) have been calculated, the sum may be evaluated at any output point x. A selection is made between minimum curvature, regularized, or continuous curvature splines in tension for either 1-D, 2-D, or 3-D Cartesian coordinates or spherical surface coordinates. After removing a linear or planar trend (i.e., in Cartesian geometries) or mean values (i.e., spherical surfaces) and normalizing residuals, a least-squares matrix solution for spline coefficients c(i) may be determined by solving the n by n linear system w(j)=sum-over-i {c(i) G(x(j); x(i))}, for j=1, n; this solution yields an exact interpolation of the supplied data points. For further details regarding the algorithms and mathematics underlying Green's function, see: (1) "Moving Surface Spline Interpolation Based on Green's Function," Xingsheng Deng and Zhong-an Tang, Math. Geosci (2011), 43:663-680 ("the Deng paper"), and (2) "Interpolation with Splines in Tension: A Green's Function Approach," Paul Wessel and David Bercovici, Mathematical Geology, 77-93, Vol. 30, No. 1, 1998 ("the Wessel paper"). The respective entireties of the Deng and Wessel papers are hereby incorporated by reference herein.

Still further details regarding the use of Green's function in interpolating and generating surfaces may be found in: Interpolation by regularized spline with tension: I. Theory and implementation, Mitasova, H., and L. Mitas, 1993, Math. Geol., 25, 641-655; Parker, R. L., 1994, Geophysical Inverse Theory, 386 pp., Princeton Univ. Press, Princeton, N.J.; Sandwell, D. T., 1987, Biharmonic spline interpolation of Geos-3 and Seasat altimeter data, Geophys. Res. Lett., 14, 139-142; Wessel, P., and J. M. Becker, 2008, Interpolation using a generalized Green's function for a spherical surface spline in tension, Geophys. J. Int, 174, 21-28, and Wessel, P., 2009, A general-purpose Green's function interpolator, Computers & Geosciences, 35, 1247-1254. Moving Surface Spline Interpolation Based on Green's Function, Xingsheng Deng, Zhong-an Tang, Mathematical Geosciences, August 2011, Volume 43, Issue 6, pp 663-680.

Note, however, that a number of different surface smoothing, surface fitting, surface estimation and/or surface/data interpolation processing techniques may be employed in step 240 of FIG. 4, which are not limited to Green's function, and which include, but are not limited to, inverse distance weighted methods of interpolation, triangulation with linear interpolation, bilinear surface interpolation methods, bivariate surface interpolation methods, cubic convolution interpolation methods, Kriging interpolation methods, Natural Neighbor or "area-stealing" interpolation methods, spline interpolation techniques (including bi-harmonic spline fitting techniques and "spline with barriers" surface interpolation methods), global polynomial interpolation methods, moving least squares interpolation methods, polynomial least square fitting interpolation methods, simple weighted-average operator interpolation methods, multi-quadric biharmonic function interpolation methods, and artificial neural network interpolation methods. See, for example: "A brief description of natural neighbor interpolation (Chapter 2)," in V. Barnett. Interpreting Multivariate Data. Chichester: John Wiley. pp. 21-36.), and "Surfaces generated by Moving Least Squares Methods," P. Lancaster et al., Mathematics of Computation, Vol. 37, No. 155 (July 1981), 141-158).

As described above, in step 250 of FIG. 4, the plurality of three-dimensional electrogram surfaces may be processed across the 2D or 3D map through time to generate a velocity vector map, the velocity vector map being configured to reveal the location of the source of the at least one cardiac rhythm disorder. According to embodiments that have been discovered to be particularly efficacious in the field of intracardiac EP monitoring and subsequent data processing and analysis, at least portions of the velocity vector map are generated using one or more optical flow analysis and estimation techniques and methods. Optical flow analysis is advantageously performed by an optical flow engine (also referred to as an optical flow detector) in the data processing and control unit 15 of System 100. Such optical flow analysis techniques may include one or more of Horn-Schunck, Buxton-Buston, Black-Jepson, phase correlation, block-based, discrete optimization, Lucas-Kanade, and differential methods of estimating optical flow. From among these various optical flow estimation and analysis techniques and methods, however, the Horn-Schunck method has so far been discovered to provide superior results in the context of processing and analyzing cardiac electrogram signals, for reasons that are discussed in further detail below.

Two papers describe the Horn-Schunck method particularly well: (1) "SimpleFlow: A Non-Iterative, Sublinear Optical Flow Algorithm," Michael Tao et al., Eurographics 2012, Vol. 31 (2012), No. 2 ("the Tao paper"), and (2) "Horn-Schunck Optical Flow with a Multi-Scale Strategy," Enric Meinhardt-Llopis et al., Image Processing On Line, 3 (2013), pp. 151-172 ("the Meinhardt-Llopis paper"). The respective entireties of the Tao and Meinhardt-Llopis papers are hereby incorporated by reference herein.

In "Determining Optical Flow," by B. K. P. Horn and B. G. Schunck, Artificial Intelligence, Vol. 17, pp. 185-204, 1981, the entirety of which is also hereby incorporated by reference herein, a method for finding an optical flow pattern is described which assumes that the apparent velocity of a brightness pattern varies smoothly throughout most of an image. The Horn-Schunck algorithm assumes smoothness in flow over most or all of an image. Thus, the Horn-Schunck algorithm attempts to minimize distortions in flow and prefers solutions which exhibit smoothness. The Horn-Schunck method of estimating optical flow is a global method which introduces a global constraint of smoothness to solve the aperture problem of optical flow.

A description of some aspects of conventional application of the Horn-Schunck method is set forth in U.S. Pat. No. 6,480,615 to Sun et al. entitled "Motion estimation within a sequence of data frames using optical flow with adaptive gradients," the entirety of which is also hereby incorporated by reference herein. As described by Sun et al., the Horn-Schunck computation is based on the observation that flow velocity has two components, and that a rate of change of image brightness requires only one constraint. Smoothness of flow is introduced as a second constraint to solve for optical flow. The smoothness constraint presumes there are no spatial discontinuities. As a result, Horn and Schunck excluded situations where objects in an image occlude or block one another. This is because at object boundaries of an occlusion in an image, discontinuities in reflectance appear.

In conventional optical flow analysis, image brightness is considered at pixel (x,y) in an image plane at time t to be represented as a function I(x,y,t). Based on initial assumptions that the intensity structures of local time-varying image regions are approximately constant under motion for at least a short duration, the brightness of a particular point in the image is constant, so that $dI/dt=0$. Based on the chain rule of differentiation, an optical flow constraint equation (I) can be represented as follows:

$$Ix(x,y,t) \cdot u + Iy(x,y,t) \cdot v + It(x,y,t) = 0,$$

where $Ix = \partial I(x,y,t)/\partial x$ = horizontal spatial gradient of the image intensity;

$Iy = \partial I(x,y,t)/\partial y$ = vertical spatial gradient of the image intensity;

$It = \partial I(x,y,t)/\partial t$ = temporal image gradient of the image intensity;

$u = dx/dt$ = horizontal image velocity (or displacement); and $v = dy/dt$ = vertical image velocity (or displacement).

The above optical flow equation is a linear equation having two unknowns, u and v). The component of motion in the direction of the brightness gradient is known to be $It/(Ix^2+Iy^2)^{1/2}$. However, one cannot determine the component of movement in the direction of the iso-brightness contours at right angles to the brightness gradient. As a consequence, the optical flow velocity (u,v) cannot be computed locally without introducing additional constraints. Horn and Schunck therefore introduce a smoothness constraint. They argue that if every point of the brightness pattern can move independently, then there is little hope of recovering the velocities. However, if opaque objects of finite size are undergoing rigid motion or deformation, neighboring points on the objects should have similar velocities. Correspondingly, the velocity field of the brightness patterns in the image will vary smoothly almost everywhere.

Advantages of the Horn-Schunck algorithm include that it yields a high density of flow vectors, i.e., the flow information missing in inner parts of homogeneous objects is filled in from the motion boundaries. On the negative side, the Horn-Schunck algorithm can be sensitive to noise.

The foregoing discussion regarding how the Horn-Schunck optical flow technique typically focuses on conventional applications, where the brightness or intensity of an object changes over time (which is where the term "optical flow" is derived from). Here, the brightness or intensity of an object is not the issue at hand. Instead, the amplitudes of electrogram signals, and how they change shape and propagate in time and space over a patient's heart, are sought to be determined. One underlying objective of method or algorithm 200 is to produce a vector velocity map, which is a representation of electrographical flow (and not optical flow) within e.g. a patient's heart. Instead of looking for differences or changes in optical brightness or intensity, changes in the velocity, direction and shape of electrical signals (i.e., changes in electrographical flow) across a patient's heart are determined. That is, algorithm 200 does not process optical measurement data corresponding to intensity or brightness, but processes electrical measurement data corresponding to amplitude, potential shape, and/or voltage.

One of the reasons why algorithm 200 works so well in detecting the locations of the sources of cardiac rhythm disorders and irregularities is that ion channels in a patient's heart produce action potential voltages that are relatively constant (except in areas of fibrosis). As described above, the Horn-Schunck method assumes "brightness constancy" as one of its key constraints. The normalized/amplitude-adjusted electrogram signals provided by step 210 help satisfy this key constraint of the Horn-Schunck method so that this method may be applied successfully in step 250.

In addition, because of the stability imparted to electrographical flow solutions determined using the Horn-Schunck method, artifacts and noise are generally low in velocity vector maps generated in step 250. In fact, it is believed that the Horn-Schunck method may generally be applied with greater success to electrographical flow data than to optical data because of the unique nature of action potential signals in the human heart, and the manner in which electrogram signals are processed and conditioned before an optical flow analysis is performed on them as described and disclosed herein.

Algorithm 200 described and disclosed herein also does not employ spatial derivatives of electrical potentials (as is done by Deno et al. and Kumaraswamy Nanthakumar using "omnipolar" signals) or time derivatives of electrogram signals (as is done in the TOPERA system). Time derivatives of signals are known to increase noise. Algorithm 200 has as its key inputs the potentials of electrogram signals (not their derivatives). As a result, algorithm 200 is notably free from the effects of spurious noise and artifacts introduced by time-derivative data processing techniques, including in step 250.

In another embodiment, the velocity vector map of step 250 is generated using the Lucas-Kanade optical flow algorithm, which is a differential method for optical flow estimation developed by Bruce D. Lucas and Takeo Kanade. It assumes that the flow is essentially constant in a local neighbourhood of a pixel under consideration, and solves the basic optical flow equations for all the pixels in that neighborhood using least squares criteria. By combining information from several nearby pixels, the Lucas-Kanade method can often resolve the inherent ambiguity of the optical flow equation. It is also less sensitive to image noise than point-wise methods. On the other hand, since it is a purely local method, it cannot provide flow information in the interior of uniform regions of the image. See "An Iterative Image Registration Technique with an Application to Stereo Vision," Bruce D. Lucase, Takeo Kanade, Proceedings of Imaging Understanding Workshop, pp. 121-130 (1981), the entirety of which is hereby incorporated by reference herein.

In yet another embodiment, various aspects of the Horn-Schunck and Lucas-Kanade algorithms are combined to yield an optical flow algorithm that exhibits the local methods inherent in Lucas-Kanade techniques and the global methods inherent in the Horn-Schunck approach and its extensions. Often local methods are more robust under noise, while global techniques yield dense flow fields. See, for example, "Lucas/Kanade Meets Horn/Schunck: Combining Local and Global Optic Flow Methods," Andres Bruhn, Joachim Weickert, Christoph Schnörr, International Journal of Computer Vision, February 2005, Volume 61, Issue 3, pp 211-231, the entirety of which is hereby incorporated by reference herein.

Various embodiments of algorithm 200 feature several advantages with respect to prior art systems and methods that generate intracardiac images and attempt to detect the locations of cardiac rhythm disorders or irregularities. A key underlying assumption of signal processing techniques that employ Hilbert Transform, Discrete Fourier Transforms (DFTs) or Fast Fourier Transforms (FFTs) is that the signal to be transformed is periodic. As is well known in the field of digital signal processing, this underlying basic assumption is frequently incorrect, and can lead to problems such as spectral leakage. Contrariwise, in some embodiments of algorithm 200, an underlying assumption is that the electrical activity in a patient's heart is based upon ion channel activation, which is a stochastic and non-periodic process, and so strictly periodic behaviour is not assumed or required in subsequent data processing and manipulation steps.

Indeed, none of steps 210, 230, 240, or 250 of method or algorithm 200 absolutely requires the use of Hilbert or Fourier transforms to process data. Instead, in some embodiments each of these steps can be carried out in the time domain without the need for frequency domain or quadrature conversion. For example, in step 210 the amplitudes of the various traces or electrograms can be normalized or adjusted in the time domain according to a selected standard deviation. In another example, rotors detected by algorithm 200 are not assumed to be singularities in a phase map (as is assumed in techniques based upon frequency domain or Hilbert transform signal processing). This key difference also explains why the rotational direction of a rotor can be revealed or detected accurately by algorithm 200 (and not at all, or very unsatisfactorily, using the frequency domain or Hilbert transforms of other methods employed to detect rotors). Note that in some embodiments, however, Hilbert, DFT and/or FFT signal processing components may be or are included in the data processing flow of algorithm 200 (e.g., DSP filtering, deconvolution, etc.).

Figure 5A:
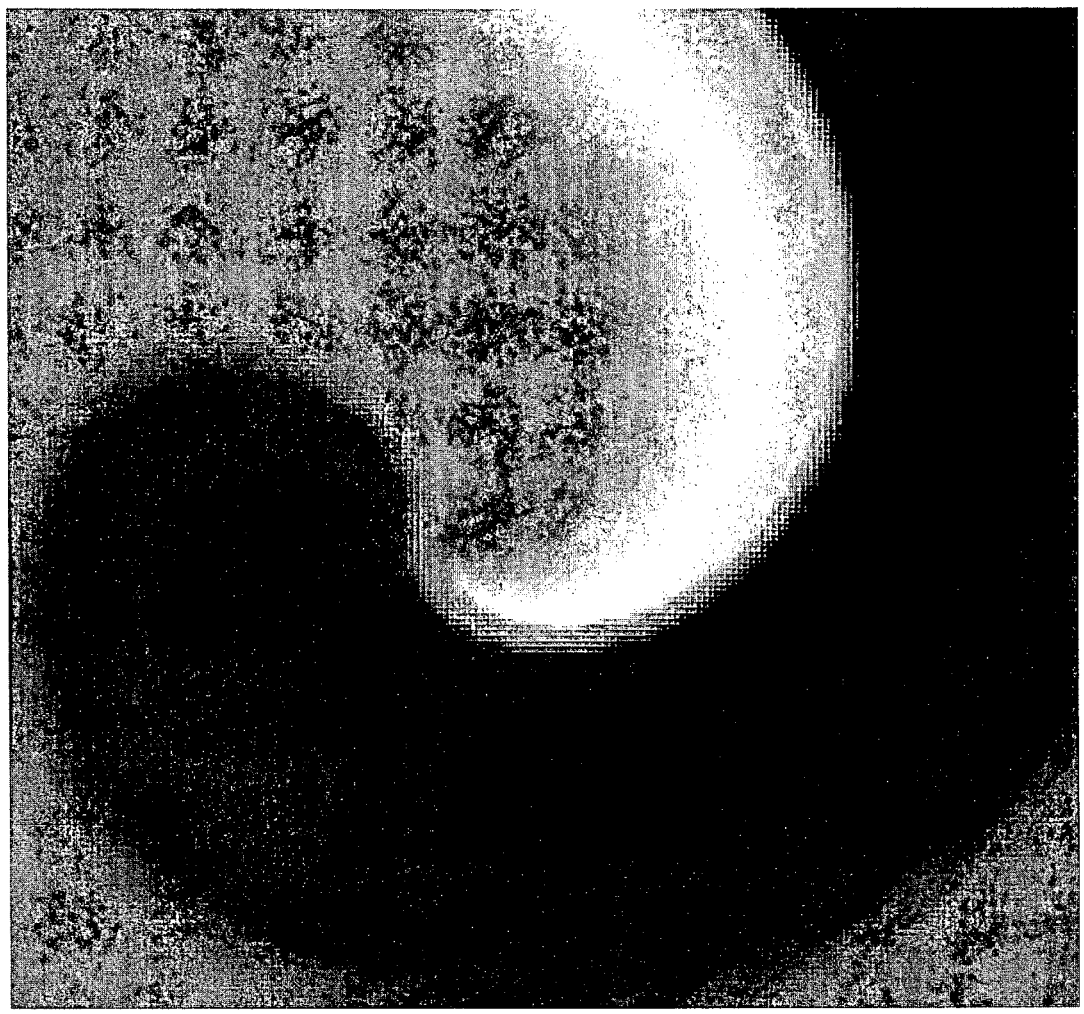
FIG. 5(a) shows a simple rotor model.

Referring now to FIG. 5(a), there is shown a simple rotor model. This model was used to generate simulated ECG signals sensed by an 8×8 array of virtual electrodes. The simple rotor model shown in FIG. 5(a) is from "Chaste: An Open Source C++ Library for Computational Physiology and Biology," Gary R. Mirams, et al. PLOS Computational Biology, Mar. 14, 2013-Vol. 9, Issue 3, e1002970, the entirety of which is hereby incorporated by reference herein.

Figure 5B:
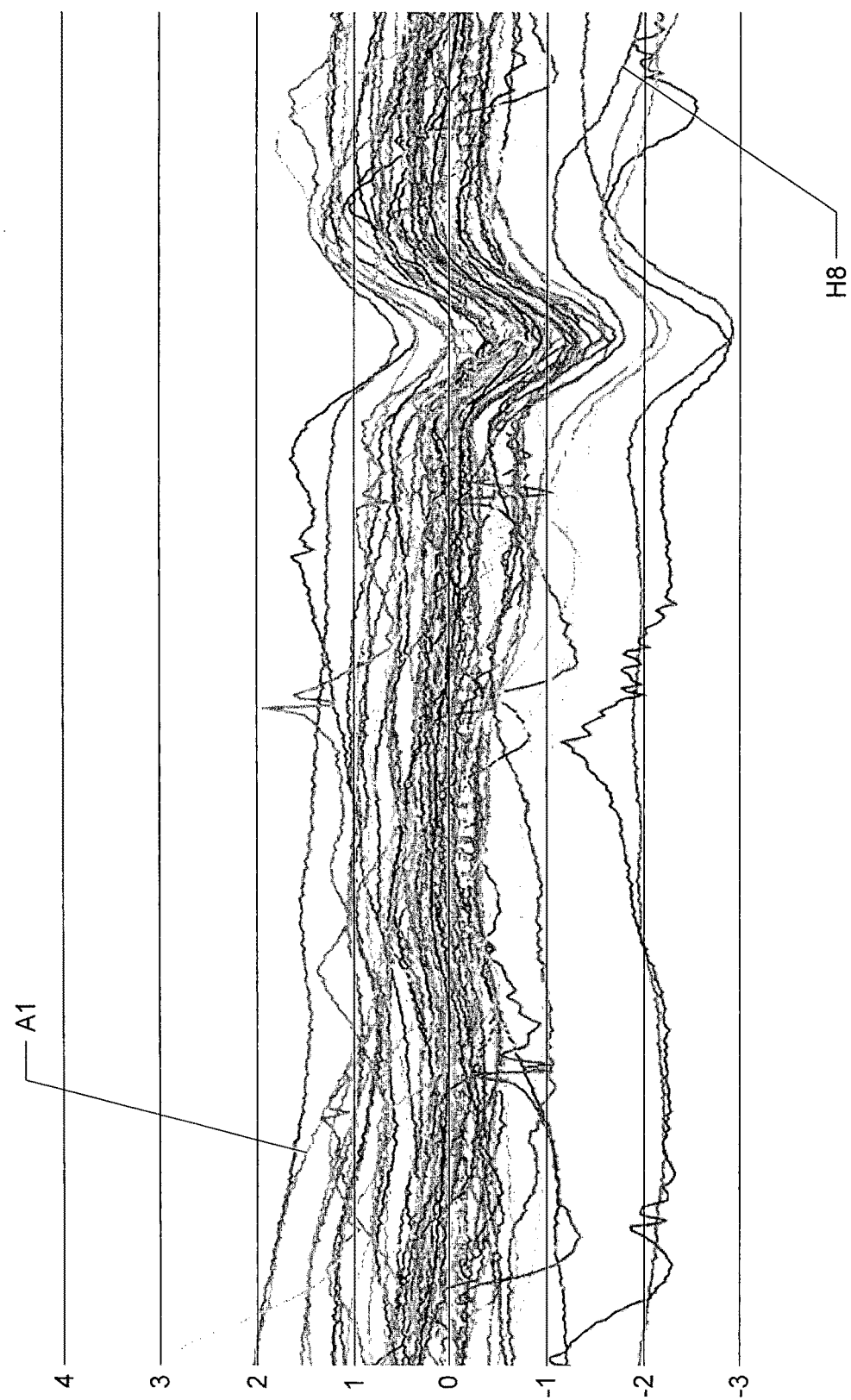
FIG. 5(b) shows sensed artifacts in electrogram signals.

FIG. 5(b) shows artifacts in electrogram signals derived from actual patient data, where 400 msec. traces were recorded using a 64-electrode basket catheter located in the left atrium of a patient suffering from atrial fibrillation. As shown in FIG. 5(b), the sensed artifacts in the electrogram signals include DC offsets of several millivolts that shift with time, a common far-field ventricular depolarization superimposed on the local potentials sensed by individual electrodes, and noise. Moreover, the amplitudes of the various sensed electrogram signals shown in FIG. 5(b) will be seen to vary considerably. These amplitude variations result at least in part on from varying degrees to which individual electrodes touch, or are physically coupled to, the patient's endocardial surface. Electrogram signals corresponding to electrodes in loose, poor or no contact with a patient's endocardium may be an order of magnitude smaller than those where electrodes are well coupled to the endocardial surface.

Figure 5C:
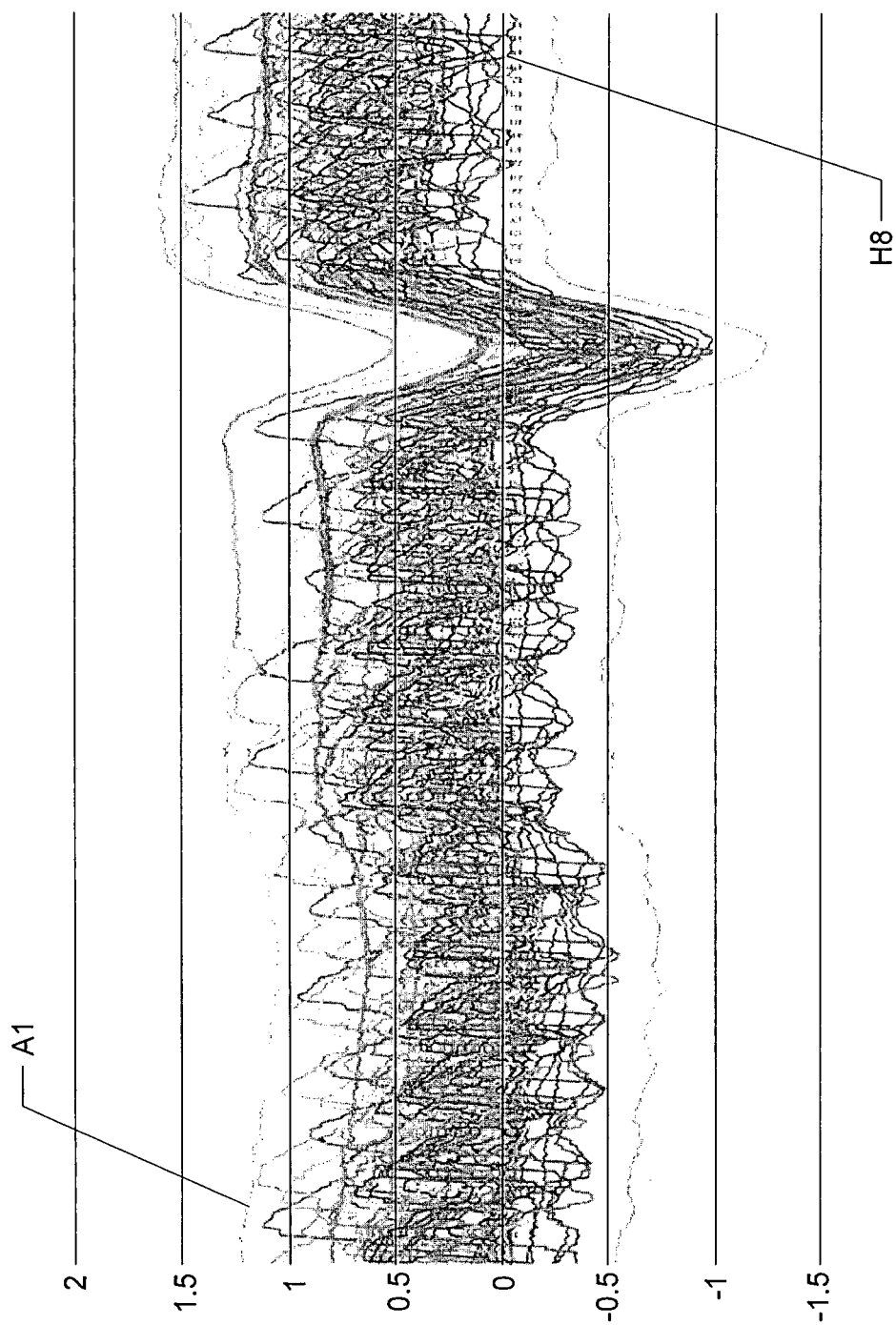
FIG. 5(c) shows the artifacts of FIG. 5(b) superimposed on simulated ECG signals.
Figure 5D:
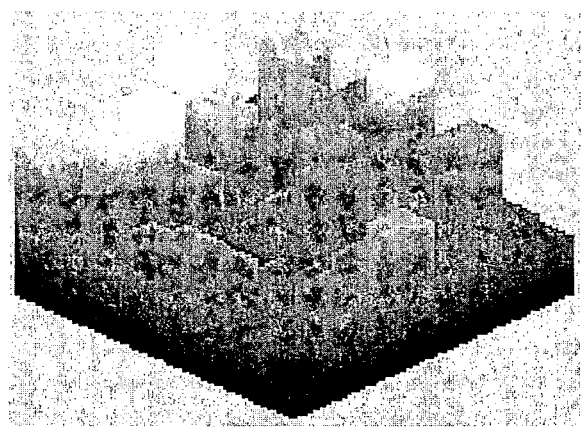
FIG. 5(d) shows a box plot corresponding to an 8×8 array of 64 electrode signals.

FIG. 5(c) shows the artifacts of FIG. 5(b) superimposed on the simulated ECG signals generated from the rotor model of FIG. 5(a). FIG. 5(d) shows a box plot corresponding to the 8×8 array of 64 electrode signals shown in FIG. 5(a) at a selected common time for all traces. Because of the artifacts from FIG. 5(b) introduced into the electrogram signals of FIG. 5(c), the box plot of FIG. 5(d) appears quite irregular and chaotic, and the original spiral shape of the underlying rotor of FIG. 5(a) is not discernable to the eye.

The data shown in FIG. 5(c) were used to perform an analysis in accordance with algorithm 200, which was carried out in three main steps: (1) normalization/adjustment/filtering of electrogram signals (step 210); (2) generating three-dimensional smoothed electrogram surfaces for discrete times or time slices from the normalized/adjusted/filtered electrogram signals (step 240) generated in the first main step 210, and (3) generating a velocity vector map based on the smoothed electrogram surfaces (step 250) generated in the second main step 240.

Figure 5E:
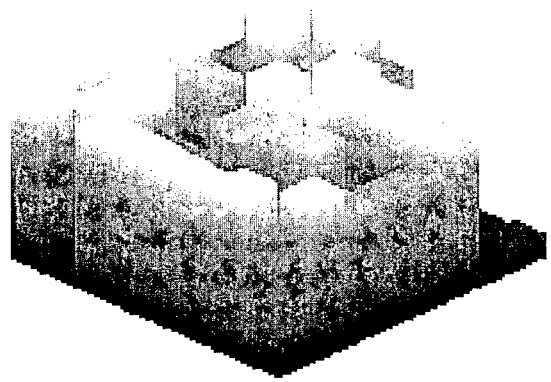
FIG. 5(e) shows the data of FIG. 5(d) after they have been subjected to an electrode signal normalization, adjustment and filtering process.

Described now is one embodiment and illustrative example of the first main step of the algorithm 200 (normalization/adjustment/filtering of electrogram signals). Referring now to FIG. 5(e), there are shown the data of FIG. 5(d) after they have been subjected to one embodiment of an electrode signal normalization, adjustment and filtering process. After normalization and filtering, the simple rotor structure shown in FIG. 5(a) becomes visible in FIG. 5(e). Uniform electrode signal amplitude minima and maxima were first calculated and then applied to individual electrogram signals to generate individual amplitude equalized electrogram signals. Unwanted artifacts such as ventricular depolarization signals were removed from the individual equalized electrogram signals by first averaging all electrogram signals to generate a common electrogram artifact signal, which was then subtracted from each of the equalized individual electrogram signals. The resulting equalized artifact-compensated electrogram signals were then high-pass filtered between 5 and 20 Hz to remove DC offsets from the electrogram signals such that the resulting filtered electrogram signals were approximately zeroed around the X (time) axis. These results are shown in FIG. 5(e).

Next, a sliding time window ranging between about 0.1 seconds and about to 1 second in length was applied to each filtered electrogram signal to generate individual amplitude-adjusted electrogram signals. (In some embodiments, the length of the sliding time window corresponds to, or is less than, the slowest repetition frequency expected to be present.) The resulting sliding-window amplitude-adjusted electrogram signals were then stored for later use to generate image backgrounds in velocity vector maps, where they could be used to show low amplitude areas indicative of valve defects/artifacts, loose electrode contact, and/or areas of fibrosis in the patient's myocardium. In the sliding-window amplitude-adjusted electrogram signals, the respective minima and maxima of each position of the sliding time window were used to normalize the amplitude values of all signals between zero and one (or 0 and 255 on an 8-bit integer numeric scale). Because the maximum and minimum values occurred at different time points for electrodes placed in different locations, this process yielded spatial information regarding action potential wave patterns for each sampled time point (more about which is said below).

Now I describe one embodiment and illustrative example of the second main step of the algorithm 200 (generating three-dimensional electrogram surfaces for discrete times or time slices, or estimation of spatial wave shapes). The second step of algorithm 200 takes the spatial distributions of all electrodes and their normalized voltage values at discrete times (e.g., the data represented by the box plots corresponding to selected discrete times within the selected time window over which electrogram signals were acquired and measured), and estimates or generates from such data or box plots corresponding to given discrete times respective continuous voltage surfaces (or action potential waveform estimates) in space. Because the electrode pattern density is limited, and depending on the method that is used to generate the estimated voltage surfaces, the estimated surfaces typically deviate to some extent from "true" surfaces. Such deviations are usually relatively small in magnitude, however, since the spatial size of the action potential wave given by its velocity (e.g., 0.5 to 1 m/sec.) times the action potential duration (e.g., 0.1 to 0.2 sec.) is much larger (e.g., 0.05 m) than the electrode spacing (e.g., about 1 mm to about 10 mm), and thus spatial aliasing generally does not occur. The electrode grid provided by catheter 110 thus permits relatively good estimates of action potential wave shapes or wavefronts. Wave shaped clusters of the electrophysiological data) in the form of smoothed electrogram surfaces to be obtained as they propagate across the myocardium. On the other hand, because of the fast sampling rate (which can, for example, range between about 0.25 milliseconds and about 8 milliseconds, and which in some embodiments is nominally about 1 millisecond), changes in the spatial shape or expression of the action potential wavefront from one sample to the next are typically relatively small (e.g., about 1 mm) compared to the electrode distances (which in some embodiments nominally range between about 2 mm and about 7 mm). Thus, algorithm 200 is capable of detecting spatial changes in action potential wavefronts or wave shapes using time domain information (i.e., small amplitude changes between time samples) to estimate changes in the spatial domain (where relatively small shifts in action potentials occur at given electrode measurement locations).

Figure 5F:
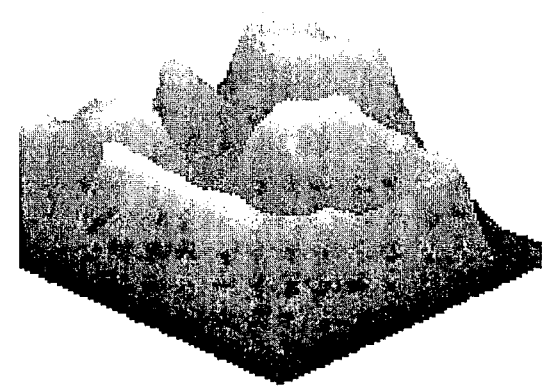
FIG. 5(f) shows a surface generated from the data shown in FIG. 5(e)

One embodiment of a method for estimating action potential wavefronts or wave shapes employs an 8×8 rectangular electrode grid (e.g., TOPERA®-like) model, which operates in two principal steps. First, each electrode/electrogram signal value at a discrete moment in time defines the height of its respective box in the "chess field" box plots shown in FIGS. 5(d) and 5(e). Second, a smoothed electrogram surface is generated for each box plot (or discrete slice of time) by calculating for each horizontal x-y point (typically on a 300×300 grid) an average of neighboring z-values (or electrical potentials) in the box plot. In 3D models that take assumed or actual electrode positions and spacing into account (using, e.g., information from a navigation or imaging system), smoothed electrogram surfaces are generated using 2D biharmonic spline interpolation techniques (embedded in a 2D biharmonic spline engine in the data processing and control unit 15 of system 100) and Green's function. Using the foregoing simple averaging approach, the smoothed electrogram surface of FIG. 5(f) was generated from the data shown in FIG. 5(e). As shown in FIG. 5(f), a spatial wave shape estimate of a rotor appears prominently in the forward center portion of the resulting smoothed surface, which tracks closely the original spiral wave shown in FIG. 5(a).

Described now is one embodiment and illustrative example of the third main step of algorithm 200 (generating a velocity vector map based on the electrogram surfaces). The third main step of algorithm 200 uses the action potential wave shape estimates or electrogram surfaces generated at discrete times or time splices provided by the second main step to calculate a velocity vector map. For each sample interval a spatial wave shape or smoothed surface is calculated according to the second main step described above. Since the wave shapes differ only by a small delta between individual samples, and minimum and maximum values are normalized, shift vectors can be calculated at a spatial resolution that is higher than the spatial resolution of the electrodes (e.g., 30×30 samples). Since individual shifts between samples may differ according to random error, a velocity vector fit can be generated using 40 to 100 samples, where an average of observed shift vectors of the action potential wave shape care calculated. If the angle of a rotating wavefront is shifted by a few degrees per sample, the vector arrows 40 will exhibit a circular pattern and in fact can resolve circles that are much smaller than inter-electrode distances. In one embodiment, the third main step of the algorithm employs a vector pattern equation that best fits the observed movement of the evaluated spatial element or wavefront. In one embodiment that has been discovered to provide excellent results, and as described above, the velocity vector map is calculated using the Horn-Schunck optical flow method described above. That is, in one embodiment the Horn-Schunck optical flow method is used in the third main step of algorithm 200 to estimate the velocity and direction of wavefronts or wave shapes between sampled times. Velocities of 40 to 100 samples are typically averaged to yield the most stable results.

Figure 5G:
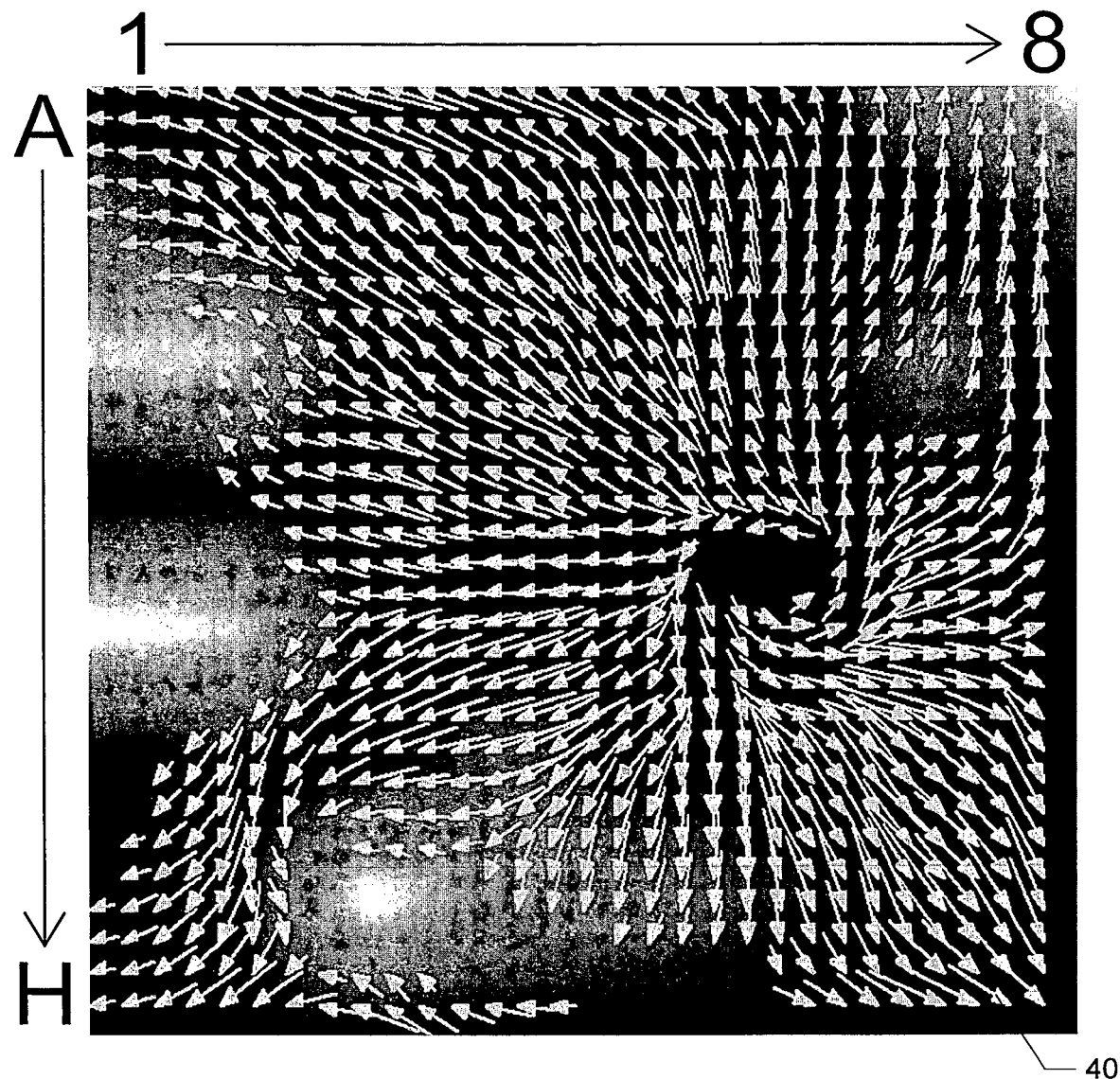
FIG. 5(g) shows wavefront velocity vectors.

FIG. 5(g) shows the resulting wavefront velocity vectors (indicated by arrows 40) calculated from a series of 60 averaged time slices of smoothed surfaces samples corresponding to the data shown in FIG. 5(f). An active rotor is distinctly visible in the right-hand central portion of FIG. 5(g), where vector arrows 40 are flowing tightly in a counterclockwise direction. In FIG. 5(g), action potential wavefronts are seen to be moving outwardly away from the detected active rotor (as would be expected in the case of an active rotor)).

Referring now to FIGS. 6(a), 6(b) and 6(c), and with further reference to FIG. 4, there are shown some of the individual steps corresponding to the three main steps 230, 240 and 250 carried out according to one embodiment of algorithm 200 disclosed and described herein.

FIG. 6(a) shows one embodiment of steps 202 through 212 of main step 210 of FIG. 4 ("normalize/adjust amplitudes, filter electrogram signals). In FIG. 6(a), step 202 is shown as comprising receiving a data file corresponding to the EP recording of electrogram signals from a basket or other type of EP recording catheter positioned in a patient's heart 10. The time interval over which such electrogram signals are recorded inside the patient's heart 10 may, of course, vary according to, among other things, the requirements of the examination that is to be performed, and/or the suspected or known cardiac rhythm disorder from which the patient suffers. Illustrative, but non-limiting, examples of such time intervals range between about a second and one minute or more. Bad or poor fidelity traces or electrograms may be selectively removed or edited at this stage.

At step 204, a high-pass filter is applied to the acquired EP data to remove DC offsets, as well as other undesirable low-frequency noise. In one embodiment, a 5 Hz high-pass filter is applied, although other filters, including band-pass filters, are contemplated, including, but not limited to, 10 Hz high-pass filters, 5-20 Hz band-pass filters, and 5-50 Hz band-pass filters. Notch- and low-pass filtering may also be applied in step 204. Hanning, trapezoidal and other digital filtering and/or Fast Fourier Transform (FFT) filtering techniques may also be applied.

At step 206, an average or adjusted far-field electrogram signal is generated by stacking and averaging all electrogram traces. In the case of atrial EP recordings, the resulting estimate of a far-field ventricular depolarization is subtracted from each trace individually, thereby removing or at least reducing the far-field component therefrom.

Especially, in step 206 the n electrogram signals (or electrogram traces as electrogram signals of a determined length) received from the n mapping electrodes 82 at a determined time slice are averaged in order to generate an average signal for the determined time slice and wherein the averaged signal is subtracted from each of the n electrogram signals to generate n adjusted electrogram signals.

At step 208, the amplitudes of individual filtered electrogram signals are normalized with respect to a given standard deviation occurring over a predetermined time window (e.g., a moving window of 200 samples around a time value "x").

At step 212, a complete filtered sample array from the grid or basket catheter is provided as an output from first main step 210.

Referring now to FIG. 6(*b*), there is shown one embodiment of the second main step 230 of algorithm 200 shown in FIG. 4 (processing amplitude-adjusted electrogram signals across the 2D or 3D representation, map or grid to generate a plurality of three-dimensional electrogram surfaces, one surface being generated for each selected or predetermined discrete time or time slice).

In FIG. 6(*b*), second main step 240 is shown as including steps 241 and 243, which according to one embodiment are performed in parallel or near-parallel. At step 241, digitally sampled and processed electrogram signals from step 212 of FIG. 6(*a*) are provided, and at step 242 an array of 200×200 empty 3D data points are generated, which correspond to the 2D or 3D representation, map or grid which is to be generated (or has already been generated). In one embodiment, such a representation, map or grid is formed by making a cylindrical projection representation, map or grid that corresponds to an approximate estimate or calculated map of the region of the patient's myocardial wall where the electrogram signals were acquired and measured (see step 243) by catheter 110. Positional data from imaging or navigation system 70 can be provided at this stage to improve the positional accuracy of the individual locations within such grid where electrogram signals were acquired. In one embodiment, for each time slice or sampled time, a Z-value or electrical potential corresponding to the normalized, adjusted and/or filtered measured voltage of each individual electrogram is assigned a location in the representation, map or grid.

At step 244, Green's function, or another suitable surface generating algorithm, is used to generate a surface of Z-values for each time slice or sampled time (more about which is said below). In one embodiment, the surface corresponding to the Z-values is smoothed.

At step 245, the calculated surface corresponding to each time slice or sampled time is provided as an output, with, for example, a 200×200 array of smoothed data points corresponding to the smoothed surface being provided for each time slice or sampled time. Note that in some embodiments the intervals at which time slices are selected, or the individual time slices themselves, may be predetermined, or may be selected automatically or by the user.

FIG. 6(*c*) shows step 250 corresponding to one embodiment of the third main step of FIG. 4 (processing the plurality of three-dimensional electrogram surfaces generated across a 2D or 3D map through time to generate a velocity vector map, for example by means of the optical flow analysis and estimation techniques and methods, such those described and disclosed elsewhere herein. In FIG. 6(*c*), third main step 250 is shown as including step 251, which in one embodiment entails sequentially accessing the individual surfaces generated for selected time slices and/or discrete times in step 240. At steps 252 and 253, adjacent time slices are analyzed and processed sequentially. In step 254, a spatial gradient corresponding to each point of the representation, map or grid is calculated say over, for example, the last 100 time slices. At step 255, a continuous graphical output of calculated flow vectors can be provided as a real-time or near-real-time output. At step 256, the most likely flow vector magnitude (or velocity) and direction for each point that minimizes energy is calculated. At step 257, X (or time) is incremented, and the foregoing calculations are repeated and refined, the final output of which is a vector velocity map of the type shown, by way of non-limiting example, in FIGS. 5(*g*), 7(*e*), 7(*i*), 7(*j*), 7(*k*), 7(*l*), 8, 9, 10(*a*), 10(*c*), and 10(*e*).

FIGS. 7(*a*) through 7(*j*) show the results of processing simulated atrial cardiac rhythm disorder data using the methods and techniques described and disclosed above, where the concept of analyzing complex rotor structures was applied to a data set of simulated data. The simulated data shown in FIG. 7(*a*) primarily comprised stable active and passive rotors, as described in Carrick et al. in "Prospectively Quantifying the Propensity for Atrial Fibrillation: A Mechanistic Formulation," R. T. Carrick, P. S. Spector et al.; Mar. 13, 2015, the entirety of which is hereby incorporated by reference herein. From Carrick, et al.'s video corresponding to the foregoing publication, and referring now to FIG. 7(*a*), stable rotor data were recorded for a frame delineated by the indicated blue square, where there are seven rotors. The recording was accomplished using the luminance of the video frame in an 8×8 matrix with an 8-bit signal depth, thereby to simulate electrogram signal data acquired using a conventional 64-electrode 8×8 basket catheter (having n=64 electrodes in a $n_x \times n_y = 8 \times 8$ grid). The overall video comprised 90 frames. All data shown n FIG. 7(*a*) were taken from frame 60. Signal amplitudes from frame 60 are shown in the chess field and box plots of FIGS. 7(*b*) and 7(*c*), respectively.

In FIG. 7(*a*), 7 rotors are shown marked with circles within the rectangle. In FIG. 7(*b*), a box plot of 8×8 matrix amplitudes is shown having amplitudes corresponding to frame 60. FIG. 7(*d*) shows the estimated wavefront or smoothed surface corresponding to frame 60. FIG. 7(*e*) shows the vector velocity map generated from the data corresponding to FIG. 7(*a*) (which was generated on the basis of all 90 frames or times slices). Reference to FIG. 7(*e*) shows that seven active rotors (marked with circles 45) are apparent, as are two passive rotors (marked with stars 46).

Figure 7A:
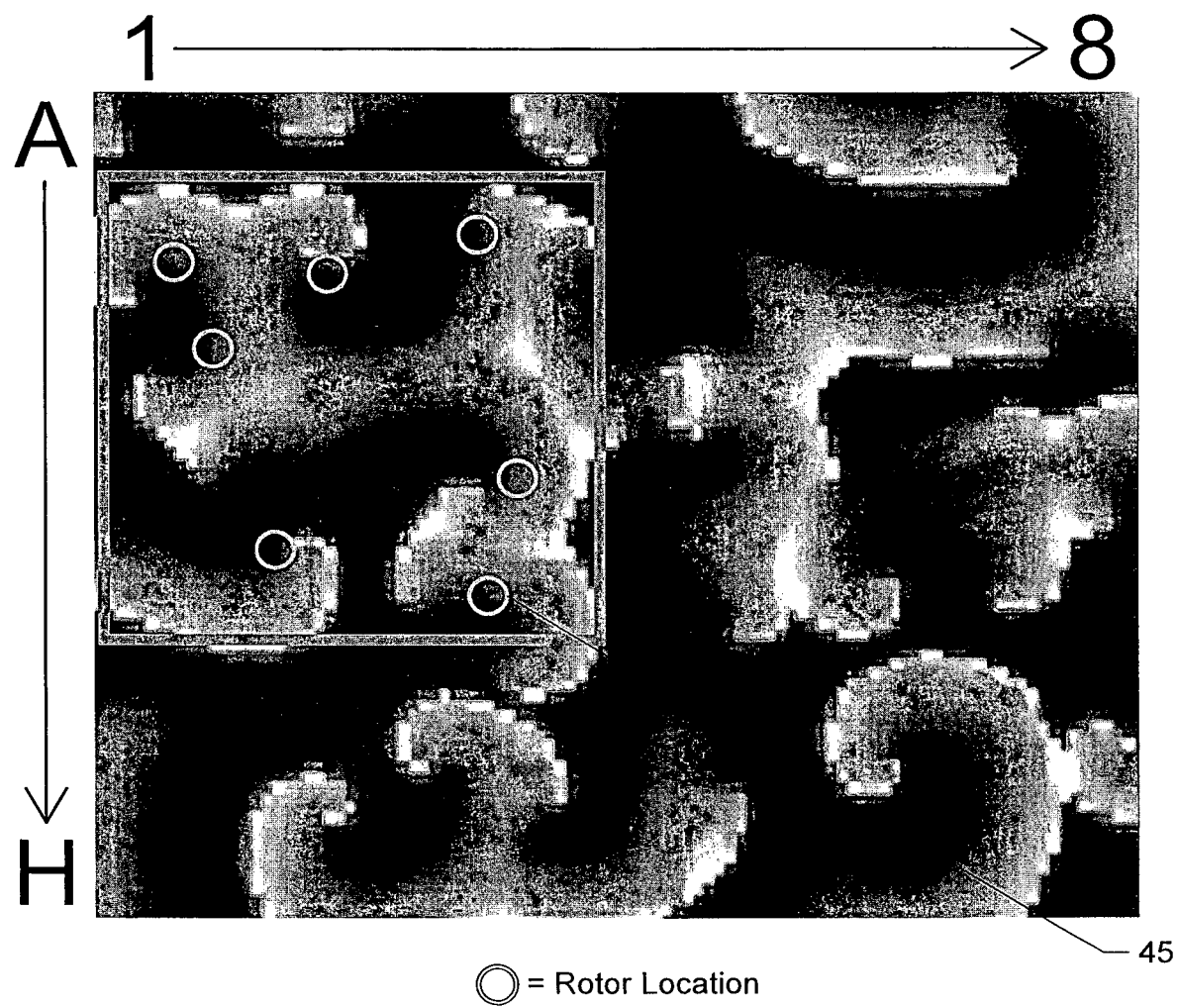

Referring now to FIGS. 7(*b*) and 7(*c*), it will be seen that the 2D and 3D box patterns shown therein provide rough estimates of the spatial wavefronts shown in FIG. 7(a). In FIG. 7(d), however, the original data shown in FIG. 7(a) are reproduced fairly accurately, and also provide a good input to the vector velocity map of FIG. 7(e) (which nicely reveals the 7 active rotors visible in FIG. 7(a)). The vector arrows 40 in FIG. 7(e) not only show the rotational centers of the individual rotors, but also show that active rotors indicated by circles 45 are driving sources of the wave fronts because the calculated vectors of the active rotors always point centrifugally away from the rotor centers. In contrast, the two stars 46 shown in FIG. 7(e) indicate the locations of passive rotors or flow turbulences that, while circular in shape, have centripetal vector directions to at least on one side of the rotor centers associated therewith.

Discrimination between active and passive rotors is critical to making proper therapeutic decisions regarding the delivery of ablation therapy, which should only target structures underlying the drivers of atrial fibrillation (namely, active rotors only, and not passive rotors).

Next, the effects of typical artifact disturbances on the signals of the 64 channels of data shown In FIGS. 7(a) through 7(d) were determined by introducing simulated variable amplitude DC-offset noise and artifacts into the electrogram signals. The objective was to test the extent to which such artifacts and noise might impair or disable the ability of algorithm 200 to detect rotors in the data.

Figure 7B:
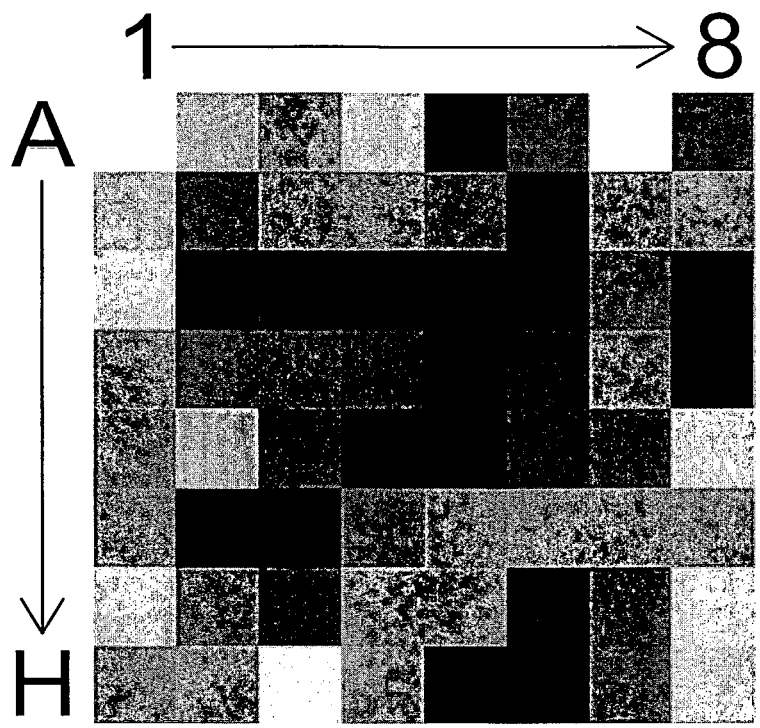
Figure 7C:
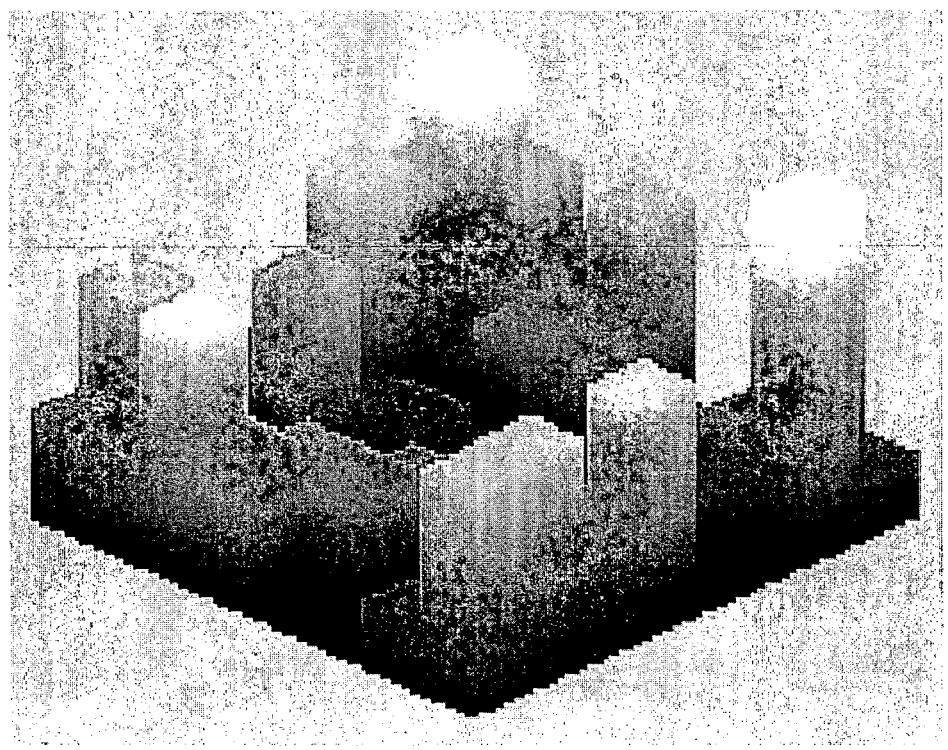
Figure 7D:
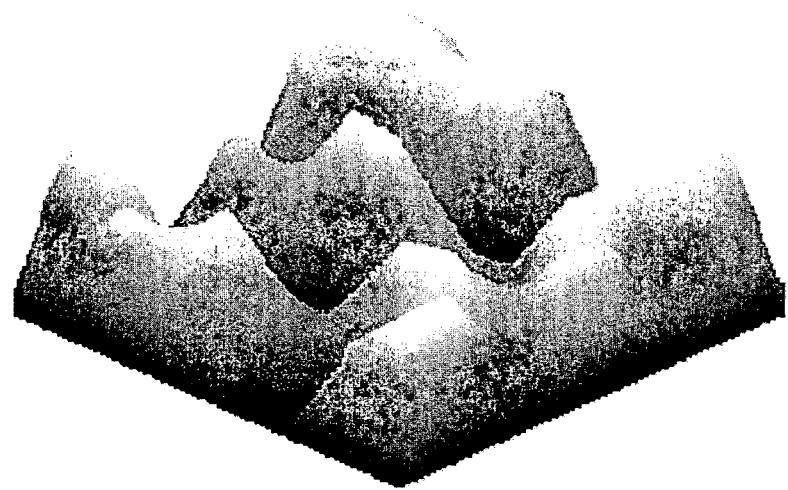
Figure 7E:
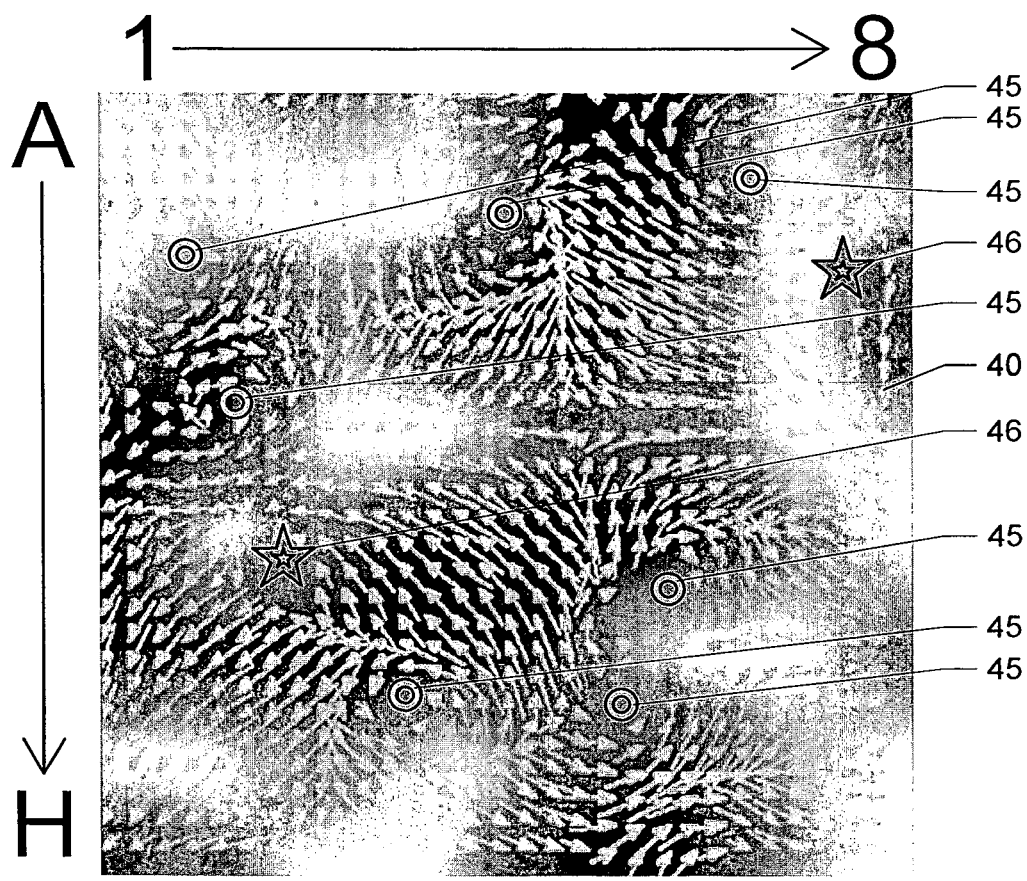
Figure 7F:
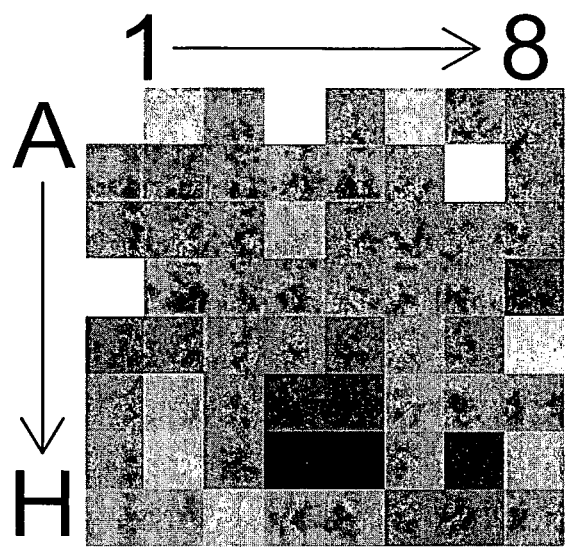
Figure 7G:
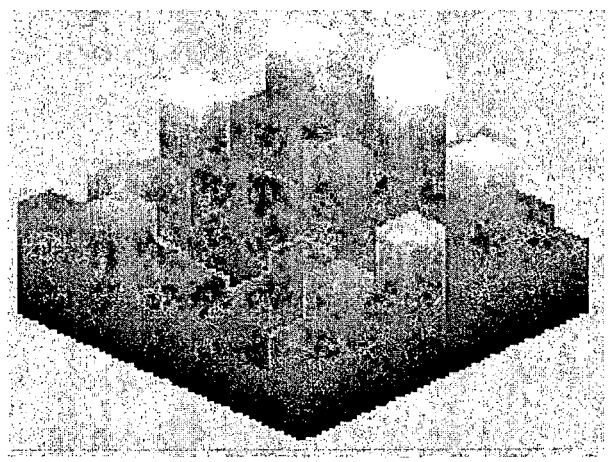
Figure 7H:
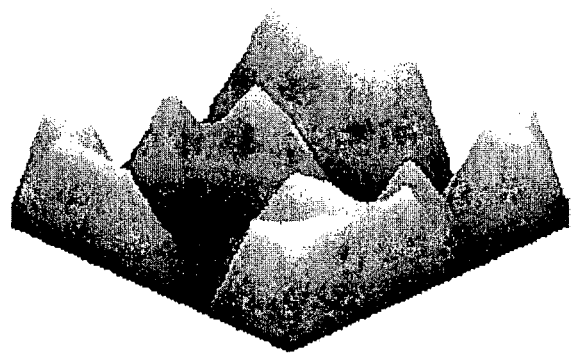

FIGS. 7(f) and 7(g) show the same box plot data as FIGS. 7(b) and 7(c), respectively, but with the foregoing-described superimposed and introduced artifacts. That is, FIGS. 7(f) and 7(g) show the chess field and box plots of the disturbed electrogram signals corresponding to frame 60. After filtering and normalization in step 210, the original rotor structure shown in FIG. 7(a) once again becomes visible in FIG. 7(h) following completion of the main second step 240 of the algorithm.

Figure 7I:
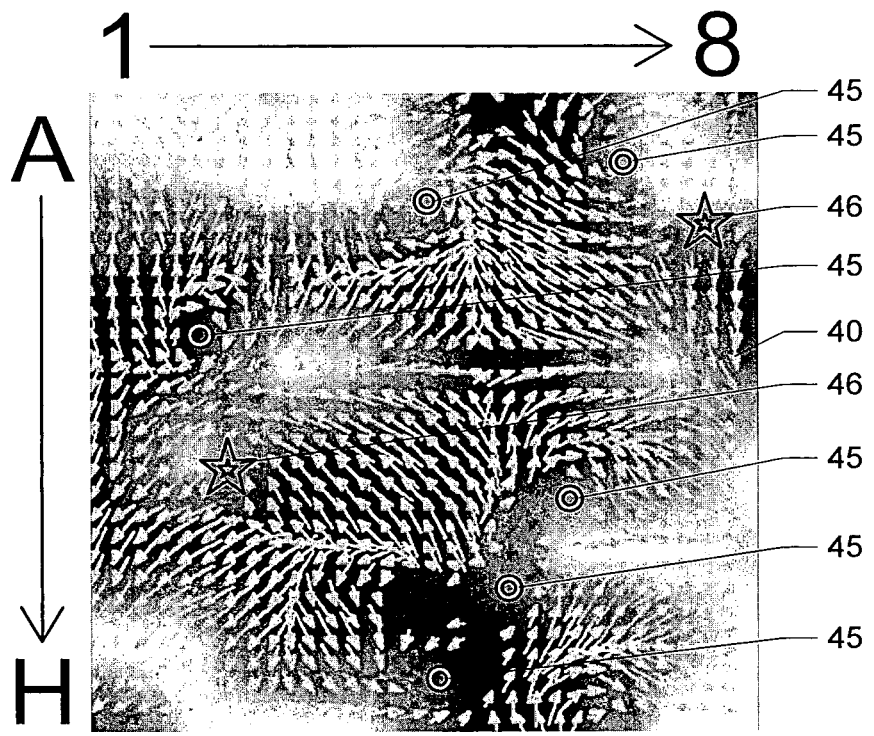

Upon applying smoothed surface calculations and fitting (as shown in FIG. 7(i)), algorithm 200 is seen to detect only five of the seven active rotors shown in FIG. 7(a). One additional active rotor, however, was detected at a different location (see FIG. 7(i)).

Figure 7J:
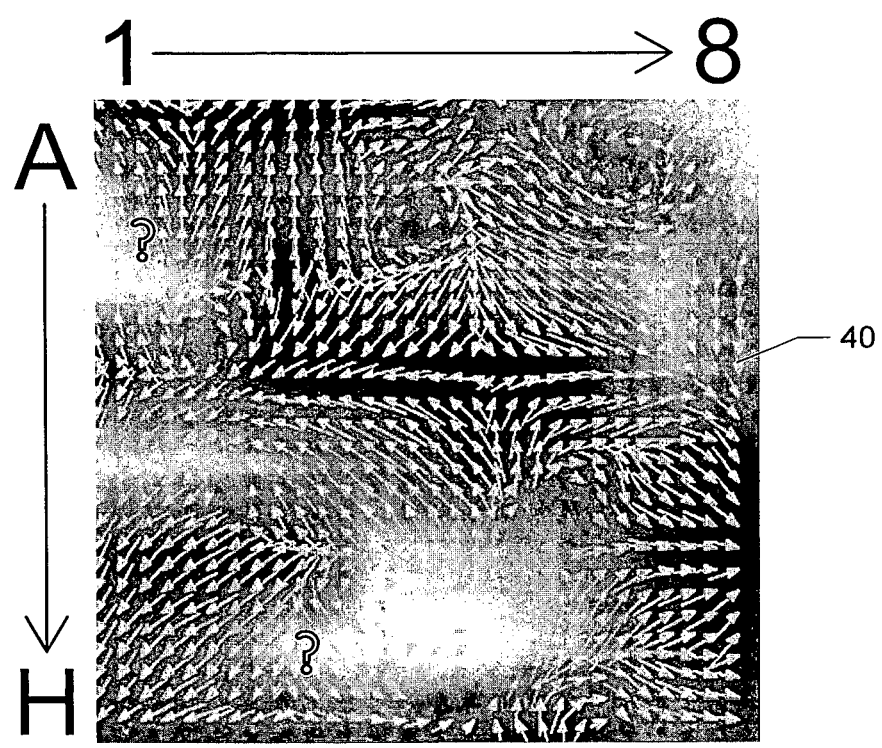

The largest variation in results was seen at positions where the introduction of the artifacts and noise reduced relative amplitude values by the greatest amount, as indicated by the white areas shown in FIG. 7(j). The white areas shown in FIG. 7(j) were generated by using the sliding-window amplitude-adjusted electrogram signal techniques described above, where electrograms processed using sliding-window techniques were used to generate the image background (including the white areas) shown in the velocity vector map of FIG. 7(j). The white areas in FIG. 7(j) thus correspond to low amplitude areas potentially indicative of valve defects or artifacts, loose electrode contact, and/or areas of fibrosis in the patient's myocardium. It is important to point out that the low-amplitude areas shown in white in the various velocity vector maps presented herein are not calculated using Green's function or optical flow data processing techniques. Instead, and as described above, these low-amplitude regions or areas may be detected by assessing the relative amplitudes of electrogram signals in step 210.

In the white areas of FIG. 7(j), the resulting velocity vector map shows that the active rotors indicated therein are slightly moved closer together than in FIG. 7(i), and on the left center side of FIG. 7(j) two rotors appearing in FIG. 7(i) are revealed as a single active rotor n FIG. 7(j). FIGS. 7(a) through 7(j) show that there are limits to the resolution that can be achieved using a conventional 8×8 array of sensing electrodes in a basket catheter having standard inter-electrode spacing. Thus, higher electrode densities and more recording channels could increase the resolution and accuracy of the results obtained using algorithm 200.

After confirming that algorithm 200 was capable of detecting complex rotor structures accurately in a patient's myocardium—even in the presence of strong artifacts and noise—algorithm 200 was applied to different time portions of the actual patient data shown in FIG. 5(b) so as to test further the algorithm's efficacy and accuracy. A velocity vector map corresponding to data acquired between 4,700 milliseconds and 5,100 milliseconds in the original EP recording of FIG. 5(b) is shown in FIG. 8(a).

As shown in FIG. 8(a), four rotors indicated by circles 1, 2 and 3 and a star 4 were detected. Circles 1 and 2 in FIG. 8(a) appear to denote active rotors that are interacting with one another. Circle (3) in FIG. 8(a) may be an active rotor, but exhibits some centripetal components. Star 4 in FIG. 8(a) clearly corresponds to a passive rotor. Next, a velocity vector map corresponding to the same data set for data acquired between samples 0 seconds and 400 milliseconds was generated, the results of which are shown in FIG. 8(b).

Differences between the results shown in FIGS. 8(a) and 8(b) permit a deeper insight into the true rotor structure of this patient's myocardium, as best shown in FIG. 8(b). In the earlier time interval (0 msec. to 400 msec.) of FIG. 8(b), the two associated rotors 1 and 2 shown in FIG. 8(a) are not yet active, while there is only a single active rotor 5 in FIG. 8(b) located between the positions of rotors 1 and 2 shown in FIG. 8(a). Rotors 1 and 2 in FIG. 8(b) show up at slightly different positions, but now appear clearly as passive rotors representing likely turbulences generated at the border of a mitral valve artifact.

Thus, a health care professional can select differing time windows over which to apply algorithm 200 to an EP mapping data set as a means of gaining a better understanding of the behavior of active and passive rotors, fibrotic regions, areas affected by valve defects or artifacts, breakthrough points and areas or defects that are at work in the patient's myocardium. The velocity vector maps generated by algorithm 200 permit a health care professional to identify such cardiac rhythm disorders in a patient's myocardium with a degree of precision and accuracy that has heretofore not been possible using conventional EP mapping and intravascular basket or spline catheter devices and methods.

Referring now to FIG. 9, there is shown another example of a vector velocity map generated from actual patient data using algorithm 200. In FIG. 9, the vector arrows 40 correspond to action potential wavefront velocity vectors, which as illustrated have differing magnitudes and directions associated herewith. As shown in FIG. 9, various cardiac rhythm defects and disorders become apparent as a result of the generated vector velocity map. The defects and disorders revealed by the vector velocity map of FIG. 9 include an active rotor (where the active rotor propagation direction is indicated in the bottom right of FIG. 9 by a circular arrow 43 rotating in a clockwise or centrifugal direction), a breakthrough point in the bottom left of FIG. 9, fibrotic areas indicted by low-amplitude white areas in the lower portion of FIG. 9, and a mitral valve defect indicted by the white area in the upper portion of FIG. 9.

Referring now to FIGS. 10(a) through 10(d), there are shown further results obtained using the actual patient data. The raw data corresponding to FIGS. 10(a) through 10(d) were acquired from a single patient's right atrium using a 64-electrode basket catheter and corresponding EP mapping/recording system. Data were acquired at a 1 millisecond rate over a time period of 60 seconds in all 64 channels. FIGS. 10(*a*) and 10(*b*) correspond to one selected 2 second time window, and FIG. 10(*d*) corresponds to another time window from the same data set. FIG. 10(*c*) shows the greyscale-schemes employed in FIGS. 10(*a*), 10(*b*), and 10(*d*).

The vector velocity map of FIG. 10(*a*) generated using algorithm 200 clearly reveals an active rotor located at chess board position D/E, 2/3. The vector velocity map of FIG. 10(*b*) was also generated using algorithm 200, but using data acquired from only 16 electrodes in grid D-G, 2-5. As shown in FIG. 10(*b*), the active rotor evident in FIG. 10(*a*) is nearly equally evident in FIG. 10(*b*) despite the significantly more sparse data grid employed to produce the velocity vector map. These remarkable results obtained using a sparse electrode grid are due in large part to the robustness, stability and accuracy of algorithm 200, as it has been applied to electrographical flow problems.

FIG. 10(*d*) shows another example of results obtained using algorithm 200 and EP mapping data obtained from the same patient as in FIGS. 10(*a*) and 10(*b*), but over a different time window. Note also that FIG. 10(*d*) shows that algorithm 200 has successfully detected one active rotor (at chess board location F2/3), three active focus points, and one passive rotor (at chess board location F8).

It will now be seen that algorithm 200 provides not only rotational direction information, but also provides high-resolution spatial information regarding the presence and location of rotors despite the use of sparse electrode grid spacing. Rotors can also move over time in a patient's myocardium, even during the time interval over which EP mapping is being carried out. The increased spatial and temporal resolution of algorithm 200 permits such shifts in rotor location to be detected.

In some embodiments, and as described above, multiple or different types of EP mapping and ablation catheters can be used sequentially or at the same time to diagnose and/or treat the patient. For example, a 64-electrode CONSTELLATION basket catheter can be used for EP mapping in conjunction with a PENTARAY16- or 20-electrode EP mapping catheter, where the PENTARAY EP mapping catheter is used to zero in on, and provide fine detail regarding, a particular region of the patient's myocardium that the basket catheter has revealed as the location of a source of a cardiac rhythm disorder or irregularity. In addition, catheter 110 or any other EP mapping catheter used in system 100 may be configured to provide ablation therapy (in addition to EP mapping functionality). The various catheters employed in system 100 may also include navigation elements, coils, markers and/or electrodes so that the precise positions of the sensing, pacing and/or ablation electrodes inside the patient's heart 10 are known. Navigational data can be employed by computer 300 in algorithm 200 to provide enhanced estimates of the locations of the electrodes in the representations, maps or grids generated thereby, which in turn increases the accuracy and efficacy of the resulting velocity vector maps generated in algorithm 200.

In another embodiment, computing device/system 300 is operably connected to a storage medium such as a hard drive or non-volatile memory located in, or operably connected to, data acquisition device 140, where computing device 300 is configured to trigger an external switch operably connected to data acquisition device 140 which permits the upload of conditioned electrogram signal data from data acquisition device 140 to computing device 300. According to such a configuration, computing device 300 and data acquisition device 140 can remain galvanically isolated from one another, and the need to physically swap USB memory sticks between data acquisition device 140 and computing device 300 is eliminated. This, in turn, permits system 100 to operate more efficiently and quickly, and to provide vector velocity maps to the health care professional in near-real-time while the EP mapping procedure is being carried out within the patient's heart 10.

Referring to FIG. 11-13, an alternative combined ablation and mapping catheter 111 is disclosed. The catheter 111 is for use with the inventive system 100 for analyzing electrophysiological data and/or the inventive method of analyzing electrophysiological data. The catheter 111 is e.g. to be used in the curative treatment of Atrial Fibrillation and other hearth rhythm diseases like Atrial Flutter, Accessory Pathways or Ventricular Tachycardia and comprises an elongated body, which is only partly shown in FIG. 11. At a distal portion of the catheter 111 which is shown in FIG. 11, there is a tip electrode 6 arranged at its distal end 112 as can especially be depicted from FIG. 13. Further, at least one further electrode which is an annular ground electrode 8 is arranged at the distal portion of the elongated body. Tip electrode 6 and ground electrode 8 are electrically isolated from each other and are used for electro-ablation of body tissue, e.g. in the left atrium 14 of the heart 10 (see FIGS. 1*a* and 2), where rotors have been detected and tissue has to be treated. Between the two electrodes 6, 8 a flexible tube is disposed which is an isolator.

A proximal portion 115 of the elongated body (see e.g. FIG. 11) is formed as a flexible tube and comprises an outer tube made e.g. of a combination of a woven grid metal-layer and plastic and/or silicone rubber and/or ChronePrene™ and an inner tube e.g. of a combination of a woven grid metal-layer and plastic and/or silicone rubber and/or Chrone-Prene™ in a radial distance of about 0.2 mm-0.4 mm.

The catheter 111 further comprises a fluid supply line, which may be connected to a fluid supply. This fluid supply line is in fluid-guiding connection to at least one fluid opening 118 in the tip electrode 6, through which an irrigation fluid, like e.g. a saline fluid, may flow to the outside of the distal portion of the catheter 111 to irrigate a surrounding portion of the vessel, organ or other body cavity into which the catheter 111 has been introduced. Fluid flow 63 through the fluid supply line and the fluid channel in the catheter 111 to the at least one fluid opening 118 to the outside of the catheter 111 is indicated by arrows 63 in FIG. 13.

The distal portion houses towards its distal end 112 a force sensor assembly 22/force sensor, preferably an optical force sensor such as described in co-pending patent application PCT/EP2015/001097 of the applicant. The force sensor assembly comprises an elastic element 51, which is formed as a helical spring that has a metal core and an outer rim, which is formed by an isolating plastic material. By means of the elastic element 51, a first and a second part of the force sensor are moveably connected with each other, whereby this connection need not be a fixed connection. Radially outwardly of the elastic element 51, the tip 6 and the ring element 21 which carries at least a part of the force sensor 22 are fluid-tightly connected by the flexible tube.

The electrode assembly 80/mapping electrode assembly is located at the distal portion of the catheter 112 and comprises in the embodiment of FIGS. 11-13 eight support arms 81, whereby it has to be mentioned that the invention requires at least two such support arms 81. Each support arm 81 has a proximal part 81*a*, a distal part 81*b* and a central part 81*c* between the proximal part 81*a* and the distal part 81*b*.

The support arms 81 are configured to have a first, unexpanded condition, in which the support arms 81 are arranged in a close fit along a portion of the elongated body.

With reference to FIGS. 11 and 12-12a, the support arms 81 are further configured to have a second, expanded condition EC, in which the central parts 81c of each of the support arms 81 project away from the elongated body 2 and are spirally wound, forming a spiral structure 83 with eight spiral arms 84 and the distal end 112 being located in a center of symmetry C of the spiral structure 83. Spiral arms 84 essentially correspond to the central parts 81c of the support arms. The center of symmetry C of the spiral structure 83 lies in a longitudinal axis A which is defined by the distal portion 3 of the elongated medical device 1. In this second, expanded condition EC of the support arms 81 the steering member 25 located in its second position 70, nearby, or in other words in a minimum distance to the distal end 112. The spiral structure 83 with the spiral arms on the other hand define a plane P which intersects the longitudinal axis A essentially perpendicularly. Further, in this expanded condition EC of the support arms 81 the electrode assembly forms an electrode array of a plurality of electrodes 81 arranged essentially in the plane P. The electrode array in the present embodiment comprises 8 support arms 81 with each support arm carrying 18 electrodes so that the electrode array counts 8 times 18 electrodes summing up to a total of 144 electrodes and has a size of about 4.4 cm in diameter which is about 15.2 cm². The corresponding spatial resolution is about 10 times higher than that of existing electro-mapping technologies.

According to FIG. 12b, two adjacent electrodes 82 on an individual support arm 81 are arranged in a distance x to each other. This distance x is between 2 mm to 9 mm, preferably between 2.5 mm to 4.5 mm. Further, two adjacent electrodes 82 on two adjacent support arms 81 are arranged in a distance y to each other. This distance y is between 2 mm to 9 mm, preferentially between 2.5 mm to 4.5 mm. Distances x and y are correlated with each other in that the distance x and the distance y are equal within a maximum tolerance in a range of +/−0.5 mm.

Referring to FIG. 13, the force sensing assembly 22, the electrode assembly 80 with its electronics unit 90 and with the electronic elements as well as the electrodes 6, 8 are connected via a line with a data processing and control unit 15 (see FIG. 1a), which energizes and controls the force sensor assembly 22 and the electrodes 6, 8. Data processing and control unit 15 processes electrode mapping data from the electrode assembly and sensor data received from the force sensor assembly 22 and outputs mapping data and force sensor data via a data output unit 16 including the display 324.

In addition or alternatively to the setup of System 100 of FIG. 1 a, the data processing and control unit 15 which may also be referred to as data acquisition, control and processing system 15 may be formed as a standard personal computer and the catheter system may have an interface to a standard computer which is connected to all the electronic components.

In a further Example for the mapping of electrophysiological data, the data processing and control unit 15 (FIG. 1 a) is configured to process digitized electrode measurement data and to output data for visualizing circular excitation pattern (rotors) 45 e.g. in the left atrium of a patient's heart on a data output unit 16 which will again be explained in detail with respect to FIGS. 14a and 14b. FIGS. 14a and 14b represent exemplary visual outputs on the screen or a sub-zone 14 of the data output unit 16.

A pre-condition of a meaningful electro-anatomic mapping is that the force sensing assembly 22 of the elongated medical device 1 or catheter has detects a sufficient perpendicular force vector F (see e.g. FIG. 2), indicating that the tip electrode 6 is in sufficient contact with the tissue (not displayed in the Figures) e.g. of the left atrium of the heart.

In electro-anatomical mapping systems the excitation in response to a pacing stimulus is measured while travelling along the walls of the atrium. The path from one side to the other is around 6 cm and the excitation needs 200 ms for this distance. In rotors 45 the "eye of the storm" has a diameter of around 1 cm (circumference of 3 cm). Thus rotor excitation cycles have a period of 200 ms or 300 beats per minute. Since action potentials are about 100 ms in duration excitation clusters have a size of about 1.5 cm.

The data output unit 16 or monitor display shows the tissue e.g. of the left atrium of the heart as a 3D object visualized from outside with the atrial septum on the backside. As mentioned above, the respective excitation pattern map is put on the surface of this object as texture of electro-anatomic data arrows 40 upon a sufficient perpendicular force vector F.

With the present elongated medical device 1 or mapping catheter system the excitation pattern or cluster has a length of about four to five electrode distances x, y. The circular excitation pattern 45 is recorded every 10 ms and visualized on a screen or sub-zone 14 of a screen of the data output unit 16 or monitor display by means of electro-anatomic data arrows 40. The circular excitation pattern (rotor) 45 travels with a speed of about half an electrode per measurement cycle. The amplitude pattern of the AC signal undergoes a software cluster analysis. Each cluster's center of gravity position is determined in each time interval or time slice. Electro-anatomic data arrows 40 are displayed on the sub-zone 14 of the screen of the data output unit 16 indicating the direction of movement of a circular excitation pattern (rotor) 45. The Electro-anatomic data arrows 40 indicate rotors 45 by their circulating behavior which is indicated by circular arrows 41a and 42 in FIG. 14a, where two active rotors 45 may be identified. The high resolution of the electro-anatomic data arrow map will allow to see the excitation path also if the voltage amplitude is changing in case of fibrosis.

FIG. 14b shows the situation after electro-ablation of the rotor 45 indicated by circular arrow 41b has taken place by using the ablation facility (tip electrode 6 and ground electrode 8) of the elongated medical device 1 or catheter. As can be seen in FIG. 14b, rotor 45 of FIG. 14a has vanished completely as indicated by circular arrow 41b.

As mentioned above, data analysis of electrophysiological data, such as action potential data, is performed on the data processing and control unit 15 respectively on a standard computer by a software that comprises an image generator, an optical flow detector or engine that performs an optical flow analysis, and a 3D engine.

When the tip electrode 6/the distal end 112 of the elongated medical device 1 touches the atrial wall the force sensor 22 triggers the integration of images coming from the image generator by the optical flow detector. The optical flow detector determines the movement of the action potentials represented by clusters in the images and integrates this action potential data into an action potential wave map once per second. Those maps are relatively time independent since the action potential speed values do not largely vary with time. Rotors and break-through points are easily visible in those maps (see again FIGS. 14a and 14b).

Once per second the action potential wave maps are handed over to the 3D engine together with the 3D coordinates of the mapping screen position. The 3D engine builds a model of the atrium textured with the action potential wave maps. The average action potential amplitudes are used for displaying structural changes of the atrium like fibrosis and are shown by slight variations of background color. A single touch of the atrial wall of one second creates 19 cm$^2$ of action potential wave map. If a larger atrium has 100 cm$^2$ in endocardial wall surface a complete mapping requires that the elongated medical device 1 touches everywhere for at least one second and with a correct angle and force F vector. The minimum would be about five recordings to cover almost the full surface. There is no harm if the areas of recording are overlapping. After the investigator has obtained a first picture of the situation RF (radio frequency) ablation via electrodes 6, 8 can already be started.

The visualization of the action potential data on the display or data output screen 14 is from inside the atrium and the center of the display is always the tip electrode 6 respectively the distal end 112. Upon an RF ablation series has been performed the generator tells the 3D engine to change the color of the existing action potential wave map to a color indicating the result of ablation, resets the optical flow detector and the mapping screen is prepared to create a new map of the atrium in order to have therapy control. If the resulting action potential wave map has fundamentally changed or atrial fibrillation has stopped the investigator may decide to continue ablation based on the previous rotor map now in pink or to reinvestigate the rotor map after this ablation series eventually after artificially restarting atrial fibrillation through pacing with the coronary sinus catheter.

The system automatically stores every individual map created in between ablation series for documentation purposes.

Action potential wave maps are created by calculating the optical flow in an optical flow analysis. Optical flow is a mathematical concept developed in the 1940s that determines motion of objects, surfaces, and edges in a visual scene. Sequences of ordered images allow the estimation of motion as either instantaneous image velocities or discrete image displacements. The intensity/(x, y, t) will have moved by Δ x, Δ y and Δ t between the two image frames.

Examples of methods to perform optical flow analysis are: Phase correlation methods, (inverse of normalized cross-power spectrum), Block-based methods (minimizing sum of squared differences or sum of absolute differences, or maximizing normalized cross-correlation), discrete optimization methods (the search space is quantized, and then image matching is addressed through label assignment at every pixel, such that the corresponding deformation minimizes the distance between the source and the target image. The optimal solution is often recovered through Max-flow min-cut theorem algorithms, linear programming or belief propagation methods), differential methods of estimating optical flow (based on partial derivatives of the image signal and/or the sought flow field and higher-order partial derivatives), such as: Lucas-Kanade method (regarding image patches and an affine model for the flow field), Horn-Schunck method (optimizing a functional based on residuals from the brightness constancy constraint, and a particular regularization term expressing the expected smoothness of the flow field), Buxton-Buxton method (based on a model of the motion of edges in image sequences), Black-Jepson method (coarse optical flow via correlation) and variations thereof.

In operation of the elongated medical device or catheter 111 will be inserted in the vessel, organ or other body cavity until it reaches the target area, which may e.g. be the left atrium of the heart. Upon arrival in the target area the operator may expand the electrode assembly 80 by moving first handle part 7a in direction of arrow 9, as displayed in FIG. 2. In this expanded condition EC of the electrode assembly 80 and its support arms 81 the medical device 1 will be pushed with its distal end 112 and respectively with its tip electrode 6 against body tissue exerting a force F on the distal end 112. Force F will be measured by the force sensing assembly 22 as has been described before. Upon detecting a sufficient force F, electro-anatomic mapping will be started either automatically or initiated by the operator as has been explained in detail above. Upon detection of circular excitation patterns (rotors) 45 electro ablation using the tip electrode 6 and ground electrode 8 will be initiated by the operator as has been explained in detail above.

Essentially, the catheter 111 is a multipurpose device which combines force detection, electro-anatomic mapping and ablation in one device.

The various systems, devices, components and methods described and disclosed herein may also be adapted and configured for use in electrophysiological mapping applications other than those involving the interior of a patient's heart. These alternative applications include EP mapping and diagnosis of a patient's epicardium, a patient's spinal cord or other nerves, or a patient's brain or portions thereof.

It will now be seen that the various systems, devices, components and methods disclosed and described herein are capable of detecting with considerable accuracy and precision the locations of sources of cardiac rhythm disorders in a patient's heart.

What have been described above are examples and embodiments of the devices and methods described and disclosed herein. It is, of course, not possible to describe every conceivable combination of components or methodologies for purposes of describing the invention, but one of ordinary skill in the art will recognize that many further combinations and permutations of the devices and methods described and disclosed herein are possible. Accordingly, the devices and methods described and disclosed herein are intended to embrace all such alterations, modifications and variations that fall within the scope of the appended claims. In the claims, unless otherwise indicated, the article "a" is to refer to "one or more than one."

The foregoing outlines features of several embodiments so that those skilled in the art may better understand the detailed description set forth herein. Those skilled in the art will now understand that many different permutations, combinations and variations of hearing aid 10 fall within the scope of the various embodiments. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

The invention claimed is:

1. A system for analyzing electrophysiological data including intracardial electrogram data, the system comprising:
   at least one computing device comprising at least one computer readable medium, the computing device being configured to store instructions executable by at least one processor to determine the source and location of at least one cardiac rhythm disorder;

a data output unit comprising a data output screen for displaying results of electrophysiological data analysis, wherein the computing device is configured to receive electrophysiological data obtained from a mapping catheter assembly comprising an electrode assembly having a plurality of n electrodes, each electrode being configured for measuring electrophysiological data in the form of electrogram signals;

and the computing device is configured to:
(a) assign predetermined positions of electrodes 82 on the electrode assembly to their respective corresponding electrogram signals;
(b) provide or generate a two-dimensional (2D) spatial map of the electrode positions;
(c) for each or selected discrete times over which the electrogram signals are being processed, process the electrogram signals to generate a plurality of three-dimensional electrogram surfaces corresponding at least partially to the 2D map, and
(d) process the plurality of three-dimensional electrogram surfaces through time to generate a velocity vector map, the velocity vector map being configured to reveal the location of the source of the at least one cardiac rhythm disorder;
and further wherein the data output unit is configured to display the velocity vector map on a data output screen of the data output unit.

2. The system of claim 1, wherein the computing device is configured to normalize or adjust amplitudes of the electrogram signals.

3. The system of claim 2, wherein the computing device is configured to high-pass-filter the normalized and/or adjusted electrogram signals.

4. to the system of claim 1, wherein computing device is configured to generate the plurality of three-dimensional electrogram surfaces using Green's function.

5. The system of claim 1, wherein the computing device is configured to process the plurality of three-dimensional electrogram surfaces through time to generate the velocity vector map using optical flow analysis techniques.

6. The system of claim 1, wherein at least portions of the electrogram surfaces generated by the computing device are configured to correspond to estimated wave shapes or wavefronts.

7. The system of claim 1, wherein electrogram surfaces are generated by the computing device using a two-dimensional bi-harmonic spline interpolation function.

8. The system of claim 1, wherein the computing device is configured to process sets of electrophysiological data associated with time slices representing electrogram signal amplitude values and to generate a series of vector data representing the average speed and direction of movement of clusters of electrophysiological data.

9. The system of claim 1, wherein the data output unit is configured to display passive and active rotors by means of the vector data that are displayed on the data output screen of the data output unit.

10. The system of claim 1, wherein the data output screen is configured to display vector data in form of vector arrows, the data vector arrows representing action potential wave maps.

11. The system of claim 1, wherein the computing device is configured to process electrophysiological data using at least one data analysis method selected from the group consisting of a phase correlation method, a block-based method, a discrete optimization method, and a differential method of estimating optical flow including the Lucas-Kanade method, the Horn-Schunck method, the Buxton-Buxton method, and the Black-Jepson method, or any variations or combinations thereof.

12. A method of analyzing electrophysiological data, including action potential data, the method comprising the steps of: measuring electrophysiological data with a plurality of mapping electrodes disposed at a distal end of an elongated medical device, receiving, at a computing device, the action potential data from the plurality of mapping electrodes;
assigning, in the computing device predetermined positions of electrodes on the electrode assembly to their respective corresponding electrogram signals;
generating, in the computing device, a two-dimensional (2D) spatial map of the electrode positions;
for each or selected discrete times over which the electrogram signals are being processed in the computing device, processing the electrogram signals to generate a plurality of three-dimensional electrogram surfaces corresponding at least partially to the 2D map; and
processing, in the computing device, the plurality of three-dimensional electrogram surfaces through time to generate a velocity vector map, the velocity vector map being configured to reveal the location of the source of at least one cardiac rhythm disorder, and
displaying the vector data on a data output screen of the data output unit.

13. The method of claim 12, wherein the velocity vector map comprises data arrows representing action potential wave maps.

14. The method of claim 12, wherein the plurality of three-dimensional electrogram surfaces is generated in computing device using Green's function.

15. The method of claim 12, wherein the plurality of three-dimensional electrogram surfaces is processed through time in the computing device to generate the velocity vector map using optical flow analysis techniques.

16. The method of claim 15, wherein the optical flow analysis is performed on sets of electrophysiological data associated with time slices comprising virtual and measured electrogram signals including their respective amplitude values to generate a series of vector data representing the average speed and direction of the movement of clusters of electrophysiological data.

17. The method of claim 12, wherein the electrogram signals are normalized or adjusted before the three-dimensional electrogram surfaces are generated..

18. The method of claim 12, wherein the electrogram signals are band-pass-filtered before the three-dimensional electrogram surfaces are -generated.

19. The method of claim 12, wherein at least portions of the electrogram surfaces generated by the computing device correspond to estimated wave shapes or wavefronts.

20. The method of claim 12, wherein the computing device generates the electrogram surfaces using a two-dimensional bi-harmonic spline interpolation function.

21. The method of claim 12, wherein the computing device is configured to process electrophysiological data using at least one data analysis method selected from the group consisting of a phase correlation method, a block-based method, a discrete optimization method, and a differential method of estimating optical flow, including the Lucas-Kanade method, the Horn-Schunck method, the Buxton-Buxton method and the Black-Jepson method, or any variations or combinations thereof.

* * * * *